(12) United States Patent
Rahat et al.

(10) Patent No.: US 9,688,732 B2
(45) Date of Patent: Jun. 27, 2017

(54) EXTRACELLULAR MATRIX METALLOPROTEINASE INDUCER (EMMPRIN) PEPTIDES AND BINDING ANTIBODIES

(71) Applicants: Rappaport Family Institute for Research in the Medical Sciences, Haifa (IL); Mor-Research Applications Ltd., Tel Aviv (IL)

(72) Inventors: Michal A. Rahat, Haifa (IL); Nitza Lahat, Atlit (IL); Miriam Walter, Nesher (IL); Haim Bitterman, Haifa (IL)

(73) Assignees: MOR—RESEARCH APPLICATIONS LTD., Tel Aviv (IL); RAPPAPORT FAMILY INSTITUTE FOR RESEARCH IN THE MEDICAL SCIENCES, Haifa (IL)

( * ) Notice: Subject to any disclaimer, the term of this patent is extended or adjusted under 35 U.S.C. 154(b) by 96 days.

(21) Appl. No.: 14/502,757

(22) Filed: Sep. 30, 2014

(65) Prior Publication Data
US 2015/0110797 A1 Apr. 23, 2015

Related U.S. Application Data

(63) Continuation of application No. PCT/IL2013/050231, filed on Mar. 13, 2013.

(60) Provisional application No. 61/746,135, filed on Dec. 27, 2012, provisional application No. 61/618,790, filed on Apr. 1, 2012.

(51) Int. Cl.
| | |
|---|---|
| A61K 39/00 | (2006.01) |
| A61K 38/00 | (2006.01) |
| C07K 14/435 | (2006.01) |
| C07K 14/705 | (2006.01) |
| C12N 15/62 | (2006.01) |
| G01N 33/574 | (2006.01) |
| C07K 16/28 | (2006.01) |
| C07K 7/06 | (2006.01) |
| C07K 7/08 | (2006.01) |
| G01N 33/68 | (2006.01) |
| G06F 19/00 | (2011.01) |

(52) U.S. Cl.
CPC ............ *C07K 14/435* (2013.01); *C07K 7/06* (2013.01); *C07K 7/08* (2013.01); *C07K 14/705* (2013.01); *C07K 16/2803* (2013.01); *C12N 15/62* (2013.01); *G01N 33/57484* (2013.01); *G01N 33/68* (2013.01); *G06F 19/3431* (2013.01); *A61K 38/00* (2013.01); *A61K 2039/505* (2013.01); *C07K 2317/34* (2013.01); *C07K 2317/76* (2013.01); *G01N 2333/70596* (2013.01)

(58) Field of Classification Search
None
See application file for complete search history.

(56) References Cited

U.S. PATENT DOCUMENTS

| | | |
|---|---|---|
| 4,539,205 A | 9/1985 | Goodman et al. |
| 4,643,992 A | 2/1987 | Goodman et al. |
| 4,767,842 A | 8/1988 | Stevens |
| 4,816,567 A | 3/1989 | Cabilly et al. |
| 4,946,778 A | 8/1990 | Ladner et al. |
| 5,011,828 A | 4/1991 | Goodman et al. |
| 5,057,540 A | 10/1991 | Kensil et al. |
| 5,091,513 A | 2/1992 | Huston et al. |
| 5,093,318 A | 3/1992 | Goodman et al. |
| 5,096,815 A | 3/1992 | Ladner et al. |
| 5,225,539 A | 7/1993 | Winter |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,709,879 A | 1/1998 | Barchfeld et al. |
| 5,910,573 A | 6/1999 | Pluckthun et al. |
| 5,977,081 A | 11/1999 | Marciani |

(Continued)

FOREIGN PATENT DOCUMENTS

| | | |
|---|---|---|
| EP | 0399843 A2 | 11/1990 |
| EP | 0404097 A2 | 12/1990 |

(Continued)

OTHER PUBLICATIONS

Colman PM. Effects of amino acid sequence changes on antibody-antigen interactions. Res Immunol. 145(1):33-36, 1994.*
Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44.*
Lederman S, et al. A single amino acid substitution in a common African allele of the CD4 molecule ablates binding of the monoclonal antibody, OKT4. Mol Immunol. 28(11):1171-81, 1991.*

(Continued)

*Primary Examiner* — Maher Haddad
(74) *Attorney, Agent, or Firm* — Vorys, Sater Seymour and Pease LLP

(57) ABSTRACT

Isolated peptides from the protein EMMPRIN (CD147/Basigin) and antibodies directed against antigenic determinants within the peptides. Pharmaceutical compositions including the peptides and antibodies and methods of their production and use in vaccination, immunotherapy and diagnosis of proliferative, hyperpermeability, inflammatory, and angiogenesis-related diseases and disorders.

8 Claims, 24 Drawing Sheets

(56) References Cited

U.S. PATENT DOCUMENTS

| | | | |
|---|---|---|---|
| 6,080,725 | A | 6/2000 | Marciani |
| 6,086,901 | A | 7/2000 | O'Hagan et al. |
| 6,113,918 | A | 9/2000 | Johnson et al. |
| 6,303,347 | B1 | 10/2001 | Johnson et al. |
| 6,355,257 | B1 | 3/2002 | Johnson et al. |
| 6,843,781 | B2 | 1/2005 | Alchas et al. |
| 7,005,500 | B2 | 2/2006 | Bejanin et al. |
| 7,250,036 | B2 | 7/2007 | Alchas |
| 7,452,680 | B2 | 11/2008 | Zerangue |
| 7,579,392 | B2 | 8/2009 | Gan et al. |
| 2003/0092643 | A1 | 5/2003 | Johnson et al. |
| 2005/0026841 | A1 | 2/2005 | Chen et al. |
| 2005/0214302 | A1 | 9/2005 | Nakada et al. |
| 2006/0104974 | A1 | 5/2006 | Davis et al. |
| 2007/0048305 | A1 | 3/2007 | Davis et al. |
| 2009/0028862 | A1 | 1/2009 | Arndt et al. |
| 2010/0248974 | A1 | 9/2010 | Chen et al. |
| 2011/0200627 | A1 | 8/2011 | Cunningham et al. |
| 2011/0287008 | A1* | 11/2011 | Yong ............... A61K 31/713 424/135.1 |

FOREIGN PATENT DOCUMENTS

| | | |
|---|---|---|
| EP | 0671948 B1 | 9/1995 |
| EP | 0689454 B1 | 1/1996 |
| GB | 2122204 A | 1/1984 |
| WO | 8601533 A1 | 3/1986 |
| WO | 9007861 A1 | 7/1990 |
| WO | 9222653 A1 | 12/1992 |
| WO | 9311161 A1 | 6/1993 |
| WO | 9315210 A1 | 8/1993 |
| WO | 9517210 A1 | 6/1995 |
| WO | 9602555 A1 | 2/1996 |
| WO | 9613583 A2 | 5/1996 |
| WO | 9633739 A1 | 10/1996 |
| WO | 9637621 A2 | 11/1996 |
| WO | 9702671 A2 | 1/1997 |
| WO | 9912565 A1 | 3/1999 |
| WO | 9952549 A1 | 10/1999 |
| WO | 9956776 A2 | 11/1999 |
| WO | 2010036460 A2 | 4/2010 |

OTHER PUBLICATIONS

Li CH, Yamashiro D, Tseng LF, Chang WC, Ferrara P. beta-Endorphin omission analogs: dissociation of immunoreactivity from other biological activities. Proc Natl Acad Sci U S A. 77(6):3211-3214, 1980.*

Wagner et al. A proteome-wide, quantitative survey of in vivo ubiquitylation sites reveals widespread regulatory roles. Mol Cell Proteomics. Oct. 2011;10(10):M111.013284.*

Kim et al. Systematic and quantitative assessment of the ubiquitin-modified proteome. Mol Cell. Oct. 21, 2011;44(2):325-40.*

Lee et al. Ubiquitin ligase substrate identification through quantitative proteomics at both the protein and peptide levels. J Biol Chem. Dec. 2, 2011;286(48):41530-8.*

Mishra et al REexseparcrhession of extracellular matrix metalloproteinase inducer (EMMPRIN) and its related extracellular matrix degrading enzymes in the endometrium during estrous cycle and early gestation in cattleReproductive Biology and Endocrinology 2010, 8:60.*

CPLM-006515. CPLM 1.0—Compendium of Protein Lysine Modification pp. 1-2, Jul. 27, 2013.*

Schulz-Utermoehl et al. Affinity and Potency of Proinhibitory Antipeptide Antibodies Against CYP2D6 is Enhanced Using Cyclic Peptides as Immunogens. Drug Metabolism and Disposition, vol. 28, No. 5, pp. 544-551.*

Amit-Cohen et al., (2013) Tumor cell-macrophage interactions increase angiogenesis through secretion of EMMPRIN. Front Physiol 4: 178; 16 pages.

Walter et al., (2015) An epitope-specific novel anti-EMMPRIN polyclonal antibody inhibits tumor progression. Oncoimmunology 5(2):e1078056; 13 pages.

Ku et al., (2007) Epitope mapping of series of monoclonal antibodies against the hepatocellular carcinoma-associated antigen HAb18G/CD147. Scand J Immunol 65(5): 435-43.

Langer (1990) New methods of drug delivery. Science 249(4976): 1527-33.

Lee et al., (2010) Differential effects of VEGFR-1 and VEGFR-2 inhibition on tumor metastases based on host organ environment. Cancer Res 70(21): 8357-67.

Lonberg and Huszar (1995) Human antibodies from transgenic mice. Int Rev Immunol 13(1): 65-93.

Lonberg et al., (1994) Antigen-specific human antibodies from mice comprising four distinct genetic modifications. Nature 368(6474): 856-9.

Marks et al., (1991) By-passing immunization. Human antibodies from V-gene libraries displayed on phage. J Mol Biol 222(3): 581-97.

Marks et al., (1992) By-passing immunization: building high affinity human antibodies by chain shuffling. Biotechnology (N Y) 10(7): 779-83.

McCafferty et al., (1990) Phage antibodies: filamentous phage displaying antibody variable domains. Nature 348 (6301): 552-4.

Morimoto and Inouye (1992) Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24(1-2): 107-17.

Morrison (1994) Immunology. Success in specification. Nature 368(6474): 812-3.

Morrison et al., (1984) Chimeric human antibody molecules: mouse antigen-binding domains with human constant region domains. Proc Natl Acad Sci U S A 81(21): 6851-5.

Muramatsu (2012) Basigin: a multifunctional membrane protein with an emerging role in infections by malaria parasites. Expert Opin Ther Targets 16(10): 999-1011.

Müller et al., (1998) The first constant domain (C(H)I and C(L)) of an antibody used as heterodimerization domain for bispecific miniantibodies. FEBS Lett 422(2): 259-64.

Nabeshima et al., (2006) Emmprin (basigin/CD147): matrix metalloproteinase modulator and multifunctional cell recognition molecule that plays a critical role in cancer progression. Pathol Int 56(7): 359-67.

Neuberger (1996) Generating high-avidity human Mabs in mice. Nat Biotechnol 14(7): 826.

Nicolaou et al., (1994) Calicheamicin θ11: A rationally designed molecule with extremely potent and selective DNA cleaving properties and apoptosis inducing acivity. Angew Chem Int Ed Engl 33: 183-186.

O'Hagan et al., (1993) Long-term antibody responses in mice following subcutaneous immunization with ovalbumin entrapped in biodegradable microparticles. Vaccine 11(9): 965-9.

Pini et al., (2008) Branched peptides as therapeutics. Curr Protein Pept Sci 9(5): 468-77.

Presta (1992) Antibody engineering. Current Opinion in Structural Biology 2(4): 593-596.

Presta et al., (1993) Humanization of an antibody directed against IgE. J Immunol 151(5): 2623-32.

R&D Systems, Inc., 614 McKinley Place NE Minneapolis, MN 55413 USA. Quantikine Human EMMPRIN Immunoassay (2010). Catalog No. DEMP00. Retrieved from the Internet : URL: http://www.funakoshi.co.jp/data/data/sheet/RSD/DEMP00.pdf. Dec. 31, 2010 (Dec. 31, 2010).

Renaudet et al., (2010) Linear and branched glyco-lipopeptide vaccines follow distinct cross-presentation pathways and generate different magnitudes of antitumor immunity. PLoS One 5(6): e11216.

Riechmann et al., (1988) Reshaping human antibodies for therapy. Nature 332(6162): 323-7.

Saltz et al., (1999) Weekly irinotecan (CPT-11), leucovorin (LV), and fluorouracil (FU) is superior to daily 5 LV/FU in patients with previously untreated metastatic colorectal cancer (abstract 898). Proc Am Soc Clin Oncol 18: 233a.

Sato et al., (2009) Identification of an active site of EMMPRIN for the augmentation of matrix metalloproteinase-1 and -3 expression in

(56) References Cited

OTHER PUBLICATIONS a co-culture of human uterine cervical carcinoma cells and fibroblasts. Gynecol Oncol 114(2): 337-42.
Shanker et al., (2008) Treating metastatic solid tumors with bortezomib and a tumor necrosis factor-related apoptosis-inducing ligand receptor agonist antibody. J Natl Cancer Inst 100(9): 649-62.
Sheets et al., (1998) Efficient construction of a large nonimmune phage antibody library: the production of high-affinity human single-chain antibodies to protein antigens. Proc Natl Acad Sci U S A 95(11): 6157-62.
Sims et al., (1993) A humanized CD18 antibody can block function without cell destruction. J Immunol 151(4): 2296-308.
Studier et al., (1990) Use of T7 RNA polymerase to direct expression of cloned genes. Methods Enzymol 185: 60-89.
Sweeny et al., (2013) A novel extracellular drug conjugate significantly inhibits head and neck squamous cell carcinoma. Oral Oncology 49(10): 991-997.
Takamatsu et al., (1987) Expression of bacterial chloramphenicol acetyltransferase gene in tobacco plants mediated by TMV-RNA. EMBO J 6(2): 307-11.
Tam (1988) Synthetic peptide vaccine design: synthesis and properties of a high-density multiple antigenic peptide system. Proc Natl Acad Sci U S A 85(15): 5409-13.
Tang et al., (2005) Extracellular matrix metalloproteinase inducer stimulates tumor angiogenesis by elevating vascular endothelial cell growth factor and matrix metalloproteinases. Cancer Res 65(8): 3193-9.
Van Poppel et al., (2009) Vaccine therapy in patients with renal cell carcinoma. Eur Urol 55(6): 1333-44.
Vaughan et al., (1996) Human antibodies with sub-nanomolar affinities isolated from a large non-immunized phage display library. Nat Biotechnol 14(3): 309-14.
Verhoeyen et al., (1988) Reshaping human antibodies: grafting an antilysozyme activity. Science 239(4847): 1534-6.
Wang et al., (2006) Inhibition of CD147 expression reduces tumor cell invasion in human prostate cancer cell line via RNA interference. Cancer Biol Ther 5(6): 608-14.
Ward et al., (1989) Binding activities of a repertoire of single immunoglobulin variable domains secreted from *Escherichia coli*. Nature 341(6242): 544-6.
Weidle et al., (2010) Cancer-related issues of CD147. Cancer Genomics Proteomics 7(3): 157-69.
Weng et al., (2010) Oral administration of resveratrol in suppression of pulmonary metastasis of BALB/c mice challenged with CT26 colorectal adenocarcinoma cells. Mol Nutr Food Res 54(2): 259-67.
Xu et al., (2007) A randomized controlled trial of Licartin for preventing hepatoma recurrence after liver transplantation. Hepatology 45(2): 269-76.
Yan et al., (2005) Roles of the multifunctional glycoprotein, emmprin (basigin; CD147), in tumour progression. Thromb Haemost 93(2): 199-204.
Yurchenko et al., (2010) Cyclophilin-CD147 interactions: a new target for anti-inflammatory therapeutics. Clin Exp Immunol 160(3): 305-17.
Zapata et al., (1995) Engineering linear F(ab')2 fragments for efficient production in *Escherichia coli* and enhanced antiproliferative activity. Protein Eng 8(10): 1057-62.
Agrawal et al., (2012) A novel anti-EMMPRIN function-blocking antibody reduces T cell proliferation and neurotoxicity: relevance to multiple sclerosis. J Neuroinflammation 9: 64.
Belton et al., (2008) Basigin-2 is a cell surface receptor for soluble basigin ligand. J Biol Chem 283(26): 17805-14.
Berge et al., (2010) Therapeutic vaccination against a murine lymphoma by intratumoral injection of a cationic anticancer peptide. Cancer Immunol Immunother 59(8): 1285-94.
Bird et al., (1988) Single-chain antigen-binding proteins. Science 242(4877): 423-6.
Bitter et al., (1987) Expression and secretion vectors for yeast. Methods Enzymol 153: 516-44.
Brennan et al., (1985) Preparation of bispecific antibodies by chemical recombination of monoclonal immunoglobulin G1 fragments. Science 229(4708): 81-3.
Brisson et al., (1984) Expression of a bacterial gene in plants by using a viral vector. Nature 310: 511-514.
Broglie et al., (1984) Light-regulated expression of a pea ribulose-1,5-bisphosphate carboxylase small subunit gene in transformed plant cells. Science 224(4651): 838-43.
Brüggemann et al., (1993) Designer mice: the production of human antibody repertoires in transgenic animals. Year Immunol 7: 33-40.
Carter et al., (1992) High level *Escherichia coli* expression and production of a bivalent humanized antibody fragment. Biotechnology (N Y) 10(2): 163-7.
Carter et al., (1992) Humanization of an anti-p185HER2 antibody for human cancer therapy. Proc Natl Acad Sci U S A 89(10): 4285-9.
Chang et al., (2004) Inhibitory effect of tetrandrine on pulmonary metastases in CT26 colorectal adenocarcinoma-bearing BALB/c mice. Am J Chin Med 32(6): 863-72.
Chothia and Lesk (1987) Canonical structures for the hypervariable regions of immunoglobulins. J Mol Biol 196(4): 901-17.
Clackson et al., (1991) Making antibody fragments using phage display libraries. Nature 352(6336): 624-8.
Coruzzi et al., (1984) Tissue-specific and light-regulated expression of a pea nuclear gene encoding the small subunit of ribulose-1,5-bisphosphate carboxylase. EMBO J 3(8): 1671-9.
Dean et al., (2009) Anti-EMMPRIN monoclonal antibody as a novel agent for therapy of head and neck cancer. Clin Cancer Res 15(12): 4058-65.
Doherty and Cleveland (2013) Targeting lactate metabolism for cancer therapeutics. J Clin Invest 123(9): 3685-92.
Douillard et al., (2000) Irinotecan combined with fluorouracil compared with fluorouracil alone as first-line treatment for metastatic colorectal cancer: a multicentre randomised trial. Lancet 355(9209): 1041-7.
Duchosal et al., (1992) Immunization of hu-PBL-SCID mice and the rescue of human monoclonal Fab fragments through combinatorial libraries. Nature 355(6357): 258-62.
Fishwild et al., (1996) High-avidity human IgG kappa monoclonal antibodies from a novel strain of minilocus transgenic mice. Nat Biotechnol 14(7): 845-51.
Genebank: "Human collagenase stimulatory factor (EMMPRIN) mRNA, complete cds", Jun. 28, 1995 (Jun. 28, 1995). Database accession No. L10240.1. Retrieved from the Internet: URL: http://www.ncbi.nlm.nih.gov/nuccore/L10240?report=GeneBank. Jun. 28, 1995 (Jun. 28, 1995).
Gonzalez et al., (2011) Chronic vaccination with a therapeutic EGF-based cancer vaccine: a review of patients receiving long lasting treatment Curr Cancer Drug Targets 11(1): 103-10.
Gurley et al., (1986) Upstream sequences required for efficient expression of a soybean heat shock gene. Mol Cell Biol 6(2): 559-65.
Hao et al., (2010) CD147/EMMPRIN and CD44 are potential therapeutic targets for metastatic prostate cancer. Curr Cancer Drug Targets 10(3): 287-306.
He et al., (2000) Calcium phosphate nanoparticle adjuvant. Clin Diagn Lab Immunol 7(6): 899-903.
He et al., (2013) Epitope mapping of metuximab on CD147 using phage display and molecular docking. Comput Math Methods Med 2013: 983829.
Hollborn et al., (2007) Positive feedback regulation between MMP-9 and VEGF in human RPE cells. Invest Ophthalmol Vis Sci 48(9): 4360-7.
Holliger et al., (1993) "Diabodies": small bivalent and bispecific antibody fragments. Proc Natl Acad Sci U S A 90(14): 6444-8.
Hoogenboom and Winter (1992) By-passing immunisation. Human antibodies from synthetic repertoires of germline VH gene segments rearranged in vitro. J Mol Biol 227(2): 381-8.
Hu et al., (2007) Redirecting adaptive immunity against foreign antigens to tumors for cancer therapy. Cancer Biol Ther 6(11): 1773-9.

(56) References Cited

OTHER PUBLICATIONS

Huston et al., (1988) Protein engineering of antibody binding sites: recovery of specific activity in an anti-digoxin single-chain Fv analogue produced in *Escherichia coli*. Proc Natl Acad Sci U S A 85(16): 5879-83.
Jakobovits et al., (1993) Analysis of homozygous mutant chimeric mice: deletion of the immunoglobulin heavy-chain joining region blocks B-cell development and antibody production. Proc Natl Acad Sci U S A 90(6): 2551-5.
Jakobovits et al., (1993) Germ-line transmission and expression of a human-derived yeast artificial chromosome. Nature 362(6417): 255-8.
Jones et al., (1986) Replacing the complementarity-determining regions in a human antibody with those from a mouse. Nature 321(6069): 522-5.
Kanekura and Chen (2010) CD147/basigin promotes progression of malignant melanoma and other cancers. J Dermatol Sci 57(3): 149-54.
Kawakami et al., (2011) Synthetic emmprin peptides with chitobiose substitution stimulate MMP-2 production by fibroblasts. BMC Cancer 11: 300.
Koga et al., (2011) Synthetic emmprin peptides inhibit tumor cell-fibroblast interaction-stimulated upregulation of MMP-2 and tumor cell invasion. Int J Oncol 39(3): 657-64.
Köhler and Milstein (1975) Continuous cultures of fused cells secreting antibody of predefined specificity. Nature 256 (5517): 495-7.
Kozbor and Roder (1983) The production of monoclonal antibodies from human lymphocytes. Immunology Today 4(3): 72-79.

\* cited by examiner

SEQUENCE LISTING

```
<160> NUMBER OF SEQ ID NOS: 44

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Gly His Arg Trp Met Arg Gly Gly Lys Val Leu Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide

<400> SEQUENCE: 2

Gly His Arg Trp Leu Lys Gly Gly Val Val Leu Cys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is Met or Leu
<220> FEATURE:
<221> NAME/KEY: MISC_FEATURE
```

```
<222> LOCATION: (6)..(6)
<223> OTHER INFORMATION: Xaa is Arg or Lys

<400> SEQUENCE: 3

Gly His Arg Trp Xaa Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is Met or Leu
<220> FEATURE:
<221> NAME/KEY: MISC_FEATURE
<222> LOCATION: (5)..(5)
<223> OTHER INFORMATION: Xaa is Arg or Lys

<400> SEQUENCE: 4

His Arg Trp Xaa Xaa Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Met or Leu
<220> FEATURE:
<221> NAME/KEY: MISC_FEATURE
<222> LOCATION: (4)..(4)
<223> OTHER INFORMATION: Xaa is Arg or Lys

<400> SEQUENCE: 5

Arg Trp Xaa Xaa Gly Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Met or Leu
<220> FEATURE:
<221> NAME/KEY: MISC_FEATURE
<222> LOCATION: (3)..(3)
<223> OTHER INFORMATION: Xaa is Arg or Lys
<220> FEATURE:
<221> NAME/KEY: MISC_FEATURE
<222> LOCATION: (6)..(6)
<223> OTHER INFORMATION: Xaa is Lys or Val

<400> SEQUENCE: 6

Trp Xaa Xaa Gly Gly Xaa
1               5

<210> SEQ ID NO 7
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Met or Leu
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (5)..(5)
<223> OTHER INFORMATION: Xaa is Lys or Val

<400> SEQUENCE: 7

Xaa Xaa Gly Gly Xaa Val
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Arg or Lys
<220> FEATURE:
<221> NAME/KEY: MISC_FEATURE
<222> LOCATION: (4)..(4)
<223> OTHER INFORMATION: Xaa is Lys or Val

<400> SEQUENCE: 8

Xaa Gly Gly Xaa Val Leu
1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is Met or Leu
<220> FEATURE:
<221> NAME/KEY: MISC_FEATURE
<222> LOCATION: (6)..(6)
<223> OTHER INFORMATION: Xaa is Arg or Lys
<220> FEATURE:
<221> NAME/KEY: MISC_FEATURE
<222> LOCATION: (9)..(9)
<223> OTHER INFORMATION: Xaa is Lys or Val

<400> SEQUENCE: 9

Gly His Arg Trp Xaa Xaa Gly Gly Xaa Val Leu
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Gly His Arg Trp Met Arg Gly Gly Lys Val Leu
1               5                   10
```

```
<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Gly His Arg Trp Leu Lys Gly Gly Val Val Leu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is Met or Leu
<220> FEATURE:
<221> NAME/KEY: MISC_FEATURE
<222> LOCATION: (6)..(6)
<223> OTHER INFORMATION: Xaa is Arg or Lys
<220> FEATURE:
<221> NAME/KEY: MISC_FEATURE
<222> LOCATION: (9)..(9)
<223> OTHER INFORMATION: Xaa is Lys or Val

<400> SEQUENCE: 12

Gly His Arg Trp Xaa Xaa Gly Gly Xaa Val Leu Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is Met or Leu
<220> FEATURE:
<221> NAME/KEY: MISC_FEATURE
<222> LOCATION: (6)..(6)
<223> OTHER INFORMATION: Xaa is Arg or Lys
<220> FEATURE:
<221> NAME/KEY: MISC_FEATURE
<222> LOCATION: (9)..(9)
<223> OTHER INFORMATION: Xaa is Lys or Val
<220> FEATURE:
<221> NAME/KEY: MISC_FEATURE
<222> LOCATION: (12)..(12)
<223> OTHER INFORMATION: Xaa is Cys or Lys

<400> SEQUENCE: 13

Gly His Arg Trp Xaa Xaa Gly Gly Xaa Val Leu Xaa
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: Xaa is Cys or Lys
```

<400> SEQUENCE: 14

Gly His Arg Trp Met Arg Gly Gly Lys Val Leu Xaa
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: Xaa is Cys or Lys

<400> SEQUENCE: 15

Gly His Arg Trp Leu Lys Gly Gly Val Val Leu Xaa
1               5                   10

<210> SEQ ID NO 16
<211> LENGTH: 24
<212> TYPE: PRT
<213> ORGANISM: Artificial Sequence
<220> FEATURE:
<223> OTHER INFORMATION: Synthetic peptide

<400> SEQUENCE: 16

Thr Cys Ser Leu Asn Ser Ser Gly Val Asp Ile Val Gly His Arg Trp
1               5                   10                  15

Met Arg Gly Gly Lys Val Leu Gln
            20

<210> SEQ ID NO 17
<211> LENGTH: 24
<212> TYPE: PRT
<213> ORGANISM: Artificial Sequence
<220> FEATURE:
<223> OTHER INFORMATION: Synthetic peptide

<400> SEQUENCE: 17

Thr Cys Ser Leu Asn Asp Ser Ala Thr Glu Val Thr Gly His Arg Trp
1               5                   10                  15

Leu Lys Gly Gly Val Val Leu Lys
            20

<210> SEQ ID NO 18
<211> LENGTH: 18
<212> TYPE: PRT
<213> ORGANISM: Artificial Sequence
<220> FEATURE:
<223> OTHER INFORMATION: Synthetic peptide

<400> SEQUENCE: 18

Ser Gly Val Asp Ile Val Gly His Arg Trp Met Arg Gly Gly Lys Val
1               5                   10                  15

Leu Gln

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Ser Ala Thr Glu Val Thr Gly His Arg Trp Leu Lys Gly Val Val
1               5                   10                  15

Leu Lys

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

Gly His Arg Phe Met Arg Gly Gly Lys Val Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Gly His Arg Phe Leu Lys Gly Gly Val Val Leu
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide

<400> SEQUENCE: 22

Gly Leu Arg Trp Met Arg Gly Gly Lys Val Leu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide

<400> SEQUENCE: 23

Gly Leu Arg Trp Leu Lys Gly Gly Val Val Leu
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide

<400> SEQUENCE: 24

Gly His Arg Trp Leu Arg Gly Gly Lys Val Leu
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

```
<400> SEQUENCE: 25

Gly His Arg Trp Leu Arg Gly Gly Val Val Leu
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Gly His Arg Trp Met Lys Gly Gly Lys Val Leu
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Gly His Arg Trp Met Lys Gly Gly Val Val Leu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide

<400> SEQUENCE: 28

Gly His Arg Trp Met Arg Cys Gly Lys Val Leu
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide

<400> SEQUENCE: 29

Gly His Arg Trp Leu Lys Cys Gly Val Val Leu
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide

<400> SEQUENCE: 30

Gly His Arg Trp Met Arg Gly Ala Lys Val Leu
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide

<400> SEQUENCE: 31
```

Gly His Arg Trp Leu Lys Gly Ala Val Val Leu
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide

<400> SEQUENCE: 32

Gly His Arg Trp Met Arg Gly Gly Val Val Leu
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide

<400> SEQUENCE: 33

Gly His Arg Trp Leu Lys Gly Gly Lys Val Leu
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Gly His Arg Trp Met Arg Gly
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide

<400> SEQUENCE: 35

Gly His Arg Trp Leu Lys Gly
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

His Arg Trp Met Arg Gly Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

```
His Arg Trp Leu Lys Gly Gly
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Arg Trp Met Arg Gly Gly Lys
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Arg Trp Leu Lys Gly Gly Val
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Trp Met Arg Gly Gly Lys Val
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Trp Leu Lys Gly Gly Val Val
1               5

<210> SEQ ID NO 42
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Cys or Lys
<220> FEATURE:
<221> NAME/KEY: MISC_FEATURE
<222> LOCATION: (6)..(6)
<223> OTHER INFORMATION: Xaa is Met or Leu
<220> FEATURE:
<221> NAME/KEY: MISC_FEATURE
<222> LOCATION: (7)..(7)
<223> OTHER INFORMATION: Xaa is Arg or Lys
<220> FEATURE:
<221> NAME/KEY: MISC_FEATURE
<222> LOCATION: (10)..(10)
<223> OTHER INFORMATION: Xaa is Lys or Val
<220> FEATURE:
```

```
<221> NAME/KEY: MISC_FEATURE
<222> LOCATION: (13)..(13)
<223> OTHER INFORMATION: Xaa is Cys or Lys

<400> SEQUENCE: 42

Xaa Gly His Arg Trp Xaa Xaa Gly Gly Xaa Val Leu Xaa
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Cys or Lys
<220> FEATURE:
<221> NAME/KEY: MISC_FEATURE
<222> LOCATION: (6)..(6)
<223> OTHER INFORMATION: Xaa is Met or Leu
<220> FEATURE:
<221> NAME/KEY: MISC_FEATURE
<222> LOCATION: (7)..(7)
<223> OTHER INFORMATION: Xaa is Arg or Lys
<220> FEATURE:
<221> NAME/KEY: MISC_FEATURE
<222> LOCATION: (10)..(10)
<223> OTHER INFORMATION: Xaa is Lys or Val

<400> SEQUENCE: 43

Xaa Gly His Arg Trp Xaa Xaa Gly Gly Xaa Val Leu
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Cys or Lys or represent's the peptide's
      N-terminal
<220> FEATURE:
<221> NAME/KEY: MISC_FEATURE
<222> LOCATION: (6)..(6)
<223> OTHER INFORMATION: Xaa is Met or Leu
<220> FEATURE:
<221> NAME/KEY: MISC_FEATURE
<222> LOCATION: (7)..(7)
<223> OTHER INFORMATION: Xaa is Arg or Lys
<220> FEATURE:
<221> NAME/KEY: MISC_FEATURE
<222> LOCATION: (10)..(10)
<223> OTHER INFORMATION: Xaa is Lys or Val
<220> FEATURE:
<221> NAME/KEY: MISC_FEATURE
<222> LOCATION: (13)..(13)
<223> OTHER INFORMATION: Xaa is Cys or Lys or represents the peptide's
      C-terminal selected from carboxy acid, amide or alcohol group

<400> SEQUENCE: 44

Xaa Gly His Arg Trp Xaa Xaa Gly Gly Xaa Val Leu Xaa
1               5                   10
```

EXTRACELLULAR MATRIX METALLOPROTEINASE INDUCER (EMMPRIN) PEPTIDES AND BINDING ANTIBODIES

The Sequence Listing submitted in text format (.txt) filed on Jun. 7, 2016, named "SequenceListing.txt", created on Jun. 7, 2016, 12.2 KB), is incorporated herein by reference.

FIELD OF THE INVENTION

The present invention relates to peptides from a specific antigenic determinant of the protein extracellular matrix metalloproteinase inducer (EMMPRIN), to antibodies which specifically recognize these peptides, and to use of the peptides and/or antibodies in diagnosis, prevention and immunotherapy of diseases involving angiogenesis, including cancer, retinal disorders and inflammatory diseases.

BACKGROUND OF THE INVENTION

Extracellular matrix metalloproteinase inducer (EMMPRIN, also known as CD147, basigin, neurothelin, OK blood group antigen, Leukocyte activation antigen M6, and Tumor cell-derived collagenase stimulatory factor TCS), is a tumor-promoting protein expressed by both tumor and stromal cells that has been shown to induce both the pro-angiogenic vascular endothelial growth factor (VEGF) and the extracellular matrix (ECM) degrading matrix metalloproteinases (MMPs), including MMP-9. In addition, EMMPRIN is involved in tumor metabolism via its interactions with the lactate transporters MCT-1 and MCT-4, in tumor drug resistance via its interactions with cyclophilins and the MDR1 protein (P-gp), and in leukocyte chemotaxis via its interactions with the extracellular cyclophilin A. Clinical trials that used a wide range of MMPs inhibitors failed to show the inhibition of tumor progression, probably due to the redundancy of MMPs in tumor tissues, and anti-VEGF antibodies provide only temporary inhibition of tumor progression. EMMPRIN, with its multiple functions in tumor survival and growth, may serve as an attractive target in cancer immunotherapy, so that immunizing against this one molecule may simultaneously affect many of its functions in promoting disease.

Both tumor cells and the infiltrating leukocytes, particularly macrophages, secrete high levels of tumor-promoting factors, such as the pro-angiogenic vascular endothelial cell growth factor (VEGF) and the ECM-degrading MMPs, both crucial for tumor progression, invasiveness, metastasis and angiogenesis. High levels of MMPs, particularly MMP-9, release and activate VEGF that is trapped by the ECM, and allow migration of leukocytes, metastatic tumor cells and endothelial cells. VEGF is a chemoattractant for macrophages, and a regulator of MMP-9. Thus, a positive feedback loop exists whereby MMP-9 and VEGF enhance each other (Hollborn et al., Invest Ophthalmol Vis Sci. 2007; 48:4360-4367).

EMMPRIN has a critical role in spermatogenesis, female fertilization, and retinal development (Weidle et al., 2010; 7:157-169). In the tumor context, EMMPRIN is expressed by both tumor and stromal cells, including macrophages (Nabeshima et al., Pathol Int. 2006; 56:359-367., Yan et al., Thromb Haemost. 2005; 93:199-204), and functions to enhance the expression of VEGF and MMPs, including MMP-9, in solid tumors. Over-expression of EMMPRIN increases invasiveness of tumor cells, and neutralizing antibody against EMMPRIN reduces the level of cellular MMP-9 and VEGF expression. Additional functions of EMMPRIN are also important for tumor survival and progression, such as its ability to chaperone the monocarboxylate transporters MCT-1 and MCT-4 that transport lactate out of the cells, its involvement in the multidrug resistance (MDR) phenotype through its interactions with cyclophilin A and P-gp (Kanekura T, Chen X. J Dermatol Sci. 2010; 57:149-154), and its ability to recruit leukocytes into the tumor through its interactions with cyclophilin A (Yurchenko V et al., Clin Exp Immunol. 2010; 160:305-317). Thus, targeting this single molecule may have many beneficial effects in cancer immunotherapy.

The regulation of EMMPRIN expression is generally unknown, although EGFR and angiotensin II were implicated in EMMPRIN expression in fibroblasts and macrophages, respectively. Equally unknown is the signaling pathway(s) that EMMPRIN initiates to induce MMP-9 and VEGF, although homophilic EMMPRIN:EMMPRIN binding, surface-anchored or soluble (Belton et al., J Biol. Chem. 2008; 283:17805-17814), was shown to elevate them and promote tumor growth and angiogenesis (Tang et al. Cancer Res. 2005; 65:3193-3199). The ability to elevate MMP-9 was mapped to the first of two heavily glycosylated extracellular domains (EC-I, EC-II or D-I and D-II, Belton R J, at el, ibid), but the precise epitopes are not known, nor is the region that regulates VEGF induction. In addition, EMMPRIN has a longer isoform that has an additional membrane-distal Ig-like domain (EC-0 or D-0, Muramatsu T, Expert Opin. Ther. Targets, 2012, 16(10):999-1011), which is expressed mostly in the retina, and is presumed to function in the complex transporting lactate.

Several attempts have been made to target EMMPRIN. Knockdown of EMMPRIN by small interfering RNA (siRNA) decreased MMP-9 and diminished invasiveness of a prostate cancer cell line in vitro (Wang et al. Cancer Biol Ther. 2006; 5:608-614). Monoclonal antibodies (mAbs) against the extracellular fragment of EMMPRIN reduced or elevated MMP-2 in human fibroblasts co-cultured with hepatocellular carcinoma cells (HCC) in vitro, suggesting that different EMMPRIN epitopes may be involved in MMPs induction. Another anti-EMMPRIN mAb reduced MMPs and VEGF secretion in co-culture of head and neck cancer cell line with fibroblasts (Dean et al. Clin Cancer Res. 2009; 15:4058-4065). Licartin, the F(ab)$_2$ fragment of an anti-EMMPRIN antibody, delayed recurrence of hepatoma after transplantation in human patients (Xu et al. Hepatology. 2007; 45:269-276), suggesting the possibility of adding passive immunization with anti-EMMPRIN to the already existing immunotherapy approaches (e.g. anti-Her/neu in breast cancer). However, anti-EMMPRIN antibodies were raised against the entire extracellular fragment, so that the epitopes responsible for the different activities of EMMPRIN remain unidentified. This may be important when designing anti-EMMPRIN immunotherapy, as targeting different epitopes may have different effects on physiological or on tumor activities of the protein. Experimental active immunization protocols exist, such as administration of whole tumor lysates, tumor antigen peptides, antigen-pulsed dendritic cells or naked-DNA plasmids, but active immunization to EMMPRIN has not yet been reported.

Angiogenesis

Angiogenesis is an important cellular event in which vascular endothelial cells proliferate, prune and reorganize to form new vessels from preexisting vascular networks. There is compelling evidence that the development of a vascular supply is essential for normal and pathological proliferative processes and inflammation. The vascular compartment is necessary not only for organ development and differentiation during embryogenesis, but also for wound healing, tissue repair and reproductive functions in the adult.

Angiogenesis is also implicated in the pathogenesis of a variety of disorders, including but not limited to, tumors, proliferative retinopathies, age-related macular degeneration, rheumatoid arthritis, and psoriasis. Angiogenesis is essential for the growth of most primary tumors and their subsequent metastasis. Tumors can absorb sufficient nutrients and oxygen by simple diffusion up to a size of 1-2 mm, at which point their further growth requires the elaboration of a vascular supply. This process is thought to involve recruitment of the neighboring host mature vasculature to begin sprouting new blood vessel capillaries, which grow toward, and subsequently infiltrate, the tumor mass. In addition, tumor angiogenesis involves the recruitment of circulating endothelial precursor cells from the bone marrow to promote neovascularization. It is suggested that the angiogenesis process is regulated by a balance between pro- and anti-angiogenic molecules, and is derailed in various diseases, especially cancer.

Angiogenesis (which involves secretion of pro-angiogenic factors such as VEGF) is initiated in many inflammatory diseases, especially in chronic inflammatory diseases.

VEGF, the most prevalent form of which is VEGF-A or vascular permeability factor (VPF), has been reported as a pivotal regulator of both normal and abnormal angiogenesis. Human VEGF is a 32-42 kilodalton (kDa) dimeric glycoprotein that mediates vasodilatation, increased vascular permeability and endothelial cell proliferation.

VEGF mRNA is overexpressed by the majority of human tumors examined. Given its central role in promoting tumor growth, VEGF is a very attractive target for therapeutic intervention. Indeed, a variety of therapeutic strategies aimed at blocking VEGF or its receptor signaling system are being developed for the treatment of neoplastic diseases.

MMPs are a family of highly homologous protein-degrading zinc-dependent endopeptidases. This family includes more than 25 members that can be divided into collagenases (MMP-1, -8, and -13), gelatinases (MMP-2 and -9), stromelysins (MMP-3 and -10), matrilysins (MMP-7 and -26), and membrane-type MMPs (MMP-14 to −17 and -24). MMPs are important in many normal biological processes including embryonic development, ovulation and implantation, bone growth, angiogenesis, inflammation, and wound healing, as well as in pathological processes such as cancer, autoimmune diseases, atherosclerosis and ischemic diseases, Alzheimer's disease and tissue destruction. MMPs collectively cleave most, if not all, of the constituents of the ECM and are involved in the breakdown and remodeling of many tissues and organ.

All inflammatory diseases require cell movement through the ECM. In particular, leukocytes must migrate from the blood vessels through the basement membrane (BM) and the ECM in order to reach the inflammatory site. This requires degradation or remodeling of the ECM and BM, which employs MMPs, including MMP-9. Additionally, many inflammatory diseases require new or additional blood supply to the inflammatory site, because the increased number of cells in the leukocyte infiltrate has higher metabolic demands that demand more oxygen and nutrients.

EMMPRIN and Anti-EMMPRIN Strategies:

Ku et al (Scandinavian Journal of Immunology 2007, 65, 435-443) describes epitope mapping of several mAbs against EMMPRIN and suggest that the fragment having the sequence AAGTVFTTVEDLGSKILLTCSLNDSATEV plays a critical role in the functions of this protein on MMP secretion and tumor invasion.

Kawakami et al. (MBC cancer 2011, 11:300, http://www.biomedcentral.com/1471-2407/11/300) demonstrated, using a polypeptide of 61 amino acids corresponding to the EC-I domain of EMMPRIN that this domain can mimic EMMPRIN activity in term of stimulating MMP-2 production by fibroblasts, when substituted with chitobiose, the disaccharide with which N-glycosylation starts.

U.S. Pat. No. 7,452,680 discloses a fusion protein between the entire sequence of rodent CD147 and human MCT1 transporter.

U.S. Pat. No. 7,005,500 discloses a polymorphic variant of human basigin which contains two immunoglobulin domains, one of which is a domain of 56 amino acids. The new variant, named BASI2, displays similar biological activities as basigin, but displays enhanced kinetic parameters during protein-protein interactions.

None of the publications disclose the specific antigenic determinant of EMMPRIN disclosed in the present invention, peptides therefrom, and specific antibodies that bind to said antigenic determinant. There is an unmet need to provide isolated immunogenic and immunotherapeutic peptides and antibodies directed against them that can be used to diagnose, prevent and treat medical conditions such as proliferative and inflammatory diseases associated with expression of the protein EMMPRIN and with regulation of VEGF and MMP levels.

SUMMARY OF THE INVENTION

The present invention provides novel short peptide sequences, from a particular epitope of the protein Extracellular matrix metalloproteinase inducer (EMMPRIN), which can be used in prevention and immunotherapy and as antigenic determinants for raising specific antibodies against EMMPRIN. These peptides and antibodies may be used in diagnosis, prevention and treatment of medical conditions associated with expression of EMMPRIN and regulation of VEGF expression. It was unexpectedly found that antibodies against these peptide determinants are capable of inhibiting VEGF and MMP-9 in vitro and tumor growth in vivo. It was also unexpectedly found that these novel peptides used for immunizing mice inhibit tumor growth and even cause regression of some of the tumors and inhibit the development of new tumor when re-challenged by tumor cell injection. It is further shown herein that peptide-based therapeutic vaccination not only reduces tumor progression but also regresses and cures tumors and evokes immune memory that is effective in preventing tumor remission. Even more unexpectedly, it is shown that such therapeutic vaccination results in reduction of metastatic development.

The present invention is based on the central role of EMMPRIN in tumor progression, and provides methods of immunization with a newly identified antigenic determinant located at the EC-I domain of EMMPRIN for the prevention and immunotherapy of proliferative and inflammatory diseases, and methods of immunization and immunotherapy with peptides from said antigenic determinant, which may support existing treatments and prevent tumor recurrence and development of metastasis. EMMPRIN, according to the present invention, encompasses any mammalian variant of the protein. According to particular embodiments, EMMPRIN protein is from human. According to other embodiments, the EMMPRIN protein is from a rodent species. According to some specific embodiments, the EMMPRIN sequence is set forth in a sequence selected from the group consisting of: human accession numbers: NM_001728.2, NM_198589.1, NM_198591.1; mouse accession numbers: NM_009768.2, NM_001077184.1; rat accession numbers: NM_012783.3, NM_001109882.1; Bos taurus accession numbers: BC151413.1, BC103059.1, NM_001075371.1; equus caballus accession number NM_001098795.1; Sus scrofa accession number: NM_001123086.1; rabbit accession number; NM_001082374.1; chimpanzee (Pan troglodytes) accession number: AK304941.1. Each possibility represents a separate embodiment of the present invention.

According to particular embodiments, the antigenic determinant is located within amino acid residues 168-178 of the human long EMMPRIN isoform having Accession number NM_001728.2 or within amino acid residues 52-62 of the human short EMMPRIN isoform having Accession number: NM_198589.1 According to other embodiments, the antigenic determinant is located within amino acid residues 168-178 of the murine long EMMPRIN isoform having Accession number NM_009768.2, or within amino acid residues 52-62 of the murine short EMMPRIN isoform having Accession number: NM_001077184.1. Each possibility represents a separate embodiment of the present invention.

According to one aspect, the present invention provides an isolated peptide of 7-25 amino acids, or an analog thereof, comprising at least six contiguous amino acids from a sequence set forth in Formula I:

(Formula I)
$X_5GHRWX_1X_2GGX_3VLX_4$ wherein $X_1$ is selected from Met and Leu, $X_2$ is selected from Arg and Lys, $X_3$ is selected from Lys and Val, $X_4$ is Cys, Lys or represents the peptide's C-terminal selected from carboxy acid, amide or alcohol group, and $X_5$ is Cys, Lys or represents the peptide's N-terminal which may be acylated. Each possibility represents a separate embodiment of the present invention.

According to some embodiments, the isolated peptide comprises a sequence selected from the group consisting of:

$X_5GHRWX_1X_2GGX_3VLX_4$; (SEQ ID NO.: 42)

$X_5GHRWX_1X_2GGX_3VL$; (SEQ ID NO.: 43)

$GHRWX_1X_2GGX_3VLX_4$ and (SEQ ID NO.: 13)

$GHRWX_1X_2GGX_3VL$; (SEQ ID NO.: 9)

and wherein $X_1$ is selected from Met and Leu, $X_2$ is selected from Arg and Lys, $X_3$ is selected from Lys and Val and $X_5$ and $X_4$ are each independently Cys or Lys.

According to some embodiments the isolated peptide or peptide analog consists of 7-15 amino acids.

According to other embodiments the isolated peptide or peptide analog consists of 8-14, 9-13, or 10-12 amino acids. Each possibility represents a separate embodiment of the present invention.

According to yet other embodiments, the isolated peptide or peptide analog consists of 8, 9, 10, 11, 12, 13 or 14 amino acids. Each possibility represents a separate embodiment of the present invention.

According to some embodiments, the peptide of 7-25 amino acids or an analog thereof, comprises at least six contiguous amino acids from a sequence selected from the group consisting of:

GHRWMRGGKVLC; (SEQ ID NO.: 1)
and

GHRWLKGGVVLC (SEQ ID NO.: 2)

According to other embodiments, the peptide of 7-25 amino acids or an analog thereof, comprises a sequence selected from the group consisting of:

$GHRWX_1X_2$; (SEQ ID NO.: 3)

$HRWX_1X_2G$; (SEQ ID NO.: 4)

$RWX_1X_2GG$; (SEQ ID NO.: 5)

$WX_1X_2GGX_3$; (SEQ ID NO.: 6)

$X_1X_2GGX_3V$; (SEQ ID NO.: 7)
and $X_2GGX_3VL$; (SEQ ID NO.: 8)

wherein $X_1$ is selected from Met and Leu, $X_2$ is selected from Arg and Lys, and $X_3$ is selected from Lys and Val. Each possibility represents a separate embodiment of the present invention.

According to some embodiments the isolated peptide or peptide analog consists of 7-15 amino acids.

According to particular embodiments, the peptide or analog thereof, consists of 11-25 amino acids comprising a sequence selected from the group consisting of:

$GHRWX_1X_2GGX_3VL$; (SEQ ID NO.: 9)

GHRWMRGGKVL; (SEQ ID NO.: 10)

GHRWLKGGVVL; (SEQ ID NO.: 11)
and $GHRWX_1X_2GGX_3VLC$; (SEQ ID NO.: 12)

wherein $X_1$ is selected from Met and Leu, $X_2$ is selected from Arg and Lys, and $X_3$ is selected from Lys and Val. According to some embodiments, the C terminus can be modified by introducing an amide or alcohol group. Each possibility represents a separate embodiment of the present invention.

According to yet other particular embodiments, the peptide consists of a sequence selected from the group consisting of:

$GHRWX_1X_2GGX_3VLX_4$; (SEQ ID NO.: 13)

GHRWMRGGKVLX₄; (SEQ ID NO.: 14)
and

GHRWLKGGVVLX₄ (SEQ ID NO.: 15)

wherein $X_1$ is selected from Met and Leu, $X_2$ is selected from Arg and Lys, $X_3$ is selected from Lys and Val and $X_4$ is Cys or Lys. Each possibility represents a separate embodiment of the present invention.

Analogs and derivatives of the peptides are also within the scope of the present application. These include but are not limited to conservative and non-conservative substitutions of amino acids, modification of the peptide's terminal (e.g. acylation of N-terminus, amidation of C-terminus etc.), insertion and deletion of amino acids within the sequence, cyclization, modification of a peptide bond, and combination of two or more such modification. Such modification and the resultant peptide analog or derivative are within the scope of the present invention as long as they confer, or even improve the immunogenicity or activity of the peptide.

The present invention further provides peptide multimers, peptide conjugates, fusion proteins comprising peptides, analogs and derivatives according to the invention.

According to some embodiments, a fusion protein according to the invention comprises an immunogenic protein carrier, such as an immunoglobulin molecule.

According to some embodiments, a peptide multimer comprising a plurality of identical or different peptides defined above is provided According to some embodiments, a peptide multimer comprising at least two identical or different peptides defined above is provided.

According to some embodiments, the at least two peptides or peptide analogs are covalently linked, directly or through a spacer or a linker.

According to some embodiments, the peptide multimer comprises a linker. According to particular embodiments, the linker comprises plurality of Lysine residues. According to some specific embodiments, the linker comprises 3-12 Lysine residues. Each possibility represents a separate embodiment of the present invention.

According to some embodiments the peptide multimer comprises a plurality of peptides arranged in an alternating sequential polymeric structure $B(X_1X_2X_3 \ldots X_m)_nB$ or in a block copolymer structure $B(X_1)_{nZ}(X_2)_{nZ}(X_3)_nZ \ldots (X_m)_n$, wherein B is an optional sequence of 1-10 amino acid residues; n is at each occurrence independently an integer of 2-50; m is an integer of 3-50; each of $X_1, X_2 \ldots X_m$ is an identical or different EMMPRIN peptide consisting of 7-25 amino acid residues as defined above; Z at each occurrence is a bond or a spacer of 1-4 amino acid residues. According to particular embodiments, n is at each occurrence independently an integer of 2-10; m is an integer of 3-10; each of $X_1$, $X_2 \ldots X_m$ is an identical or different EMMPRIN peptide consisting of 7-15 amino acid residues as defined above; Z at each occurrence is a bond or a spacer of 1-4 amino acid residues. Each possibility represents a separate embodiment of the present invention.

According to some embodiments the peptide multimer comprises 2-16 different or identical peptides. According to a particular embodiment the peptide multimer comprises 4-10 copies of a single peptide sequence. According to yet other embodiments, the peptide multimer consists of 2-16, 4-10 or 4-8 different or identical peptides. Each possibility represents a separate embodiment of the present invention.

According to a particular embodiment, the peptide multimer is a molecule according to Formula II or III:

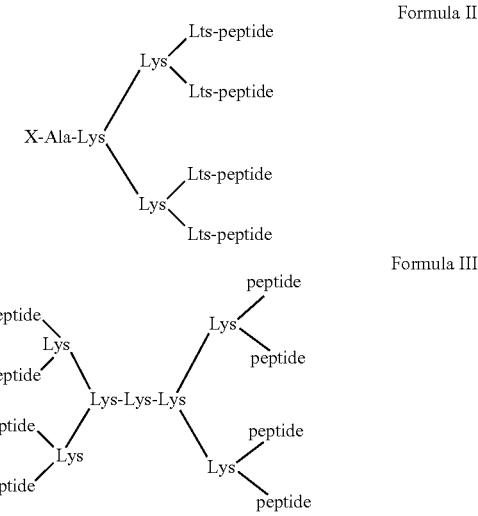

wherein X represents the peptide's C-terminal selected from carboxy acid, amide or alcohol group, "peptide" denotes a stretch of 7-25 amino acids comprising at least six contiguous amino acids derived from Formula I: $X_5$-G-H-R-W-$X_1$-$X_2$-G-G-$X_3$-V-L-$X_4$, wherein $X_1$ is selected from Met and Leu, $X_2$ is selected from Arg and Lys, $X_3$ is selected from Lys and Val; $X_4$ is Cys, Lys or represents the peptide's C-terminal selected from carboxy acid, amide or alcohol group, and $X_5$ is Cys, Lys or represents the peptide's N-terminal which may be acylated. Each possibility represents a separate embodiment of the present invention.

According to some embodiments the "peptide" is selected from a sequence set forth in any one of SEQ ID NOs: 1-15.

A peptide conjugate according to the present invention comprises any peptide, peptide analog or peptide multimer defined above, conjugated to a carrier protein or moiety which improves the peptide's antigenicity, solubility, stability or permeability. A fusion protein comprising at least one peptide according to the invention is also within this scope.

According to some embodiments the at least one peptide of the conjugate or of the fusion protein is selected from a sequence set forth in any one of SEQ ID NOs: 1-15.

The peptide of present invention may be produced by any method known in the art, including recombinant and synthetic methods. According to some embodiments a synthetic peptide, peptide multimer or peptide conjugate is provided. According to other embodiments a recombinantly produced peptide, peptide multimer, peptide fusion protein or peptide conjugate with a carrier protein is provided.

According to some embodiments, the fusion protein comprises an immunogenic carrier, such as an immunoglobulin molecule.

Isolated polynucleotide sequences comprising at least one sequence encoding a peptide, peptide analog, conjugate or fusion protein are also included in the scope of the present invention. According to some embodiments, a polynucleotide sequence encoding a peptide or peptide analog is translationally linked to another polynucleotide sequence such as an RNA or DNA molecule and is recombinantly expressed within target cells. According to other embodiments, said polynucleotide sequence is part of a recombinant viral or bacterial vector. According to some embodiments a peptide encoded by said polynucleotide sequence is selected from a sequence set forth in any one of SEQ ID NOs: 1-15.

According to another aspect, the present invention provides a pharmaceutical composition comprising at least one peptide, analog, peptide multimer, fusion protein or peptide conjugate as defined above, and a pharmaceutically acceptable carrier or diluent.

According to some embodiments the pharmaceutical composition is formulated as a vaccine.

According to some particular embodiments, the vaccine composition comprises an adjuvant or a delivery system. According to other embodiments, the vaccine formulation does not comprise an adjuvant or delivery system. According to yet other particular embodiments, the vaccine formulation comprises at least one peptide multimer, fusion protein or peptide conjugate.

Pharmaceutically acceptable adjuvants include, but are not limited to water in oil emulsions, lipid emulsions, and liposomes. According to some embodiments the adjuvant is selected from the group consisting of: Montanide®, alum, muramyl dipeptide, Gelvac®, chitin microparticles, chitosan, cholera toxin subunit B, labile toxin, AS21A, Intralipid®, and Lipofundin®.

In some embodiments the vaccine is formulated for intramuscular, intranasal, oral, intraperitoneal, subcutaneous, topical, intradermal and transdermal delivery. In some embodiments the vaccine is formulated for intramuscular administration. In yet other embodiments the vaccine is formulated for intranasal administration.

The present invention provides according to further embodiments methods for inducing an immune response against EMMPRIN in a subject, comprising administering a vaccine composition comprising at least one synthetic or recombinant peptide, peptide analog, conjugate, multimer or fusion protein according to the invention.

A vaccine composition, comprising at least one synthetic or recombinant peptide, peptide analog, conjugate, multimer or fusion protein according to the invention for inducing an immune response against EMMPRIN in a subject is also provided.

The present invention further provides methods and uses of the peptides, peptide multimers and peptide conjugates for production of antibodies specific to EMMPRIN. According to some embodiments the antibodies are polyclonal antibodies. According to other embodiments, the antibodies are monoclonal antibodies. Any method known in the art for production of monoclonal or polyclonal antibodies may be used.

According to another aspect, an antibody to EMMPRIN, or an antibody fragment thereof comprising at least an antigen-binding portion, is provides wherein said antibody recognizes an epitope of at least six contiguous amino acids from a sequence set forth in Formula I:

$$X_5\text{-}G\text{-}H\text{-}R\text{-}W\text{-}X_1\text{-}X_2\text{-}G\text{-}G\text{-}X_3\text{-}V\text{-}L\text{-}X_4 \quad \text{(Formula I)}$$

wherein $X_1$ is selected from Met and Leu, $X_2$ is selected from Arg and Lys, $X_3$ is selected from Lys and Val; $X_5$ is Cys, Lys or represents the peptide's N-terminal which may be acylated, and $X_4$ is Cys, Lys or represents the peptide's C-terminal selected from carboxy acid, amide or alcohol group. Each possibility represents a separate embodiment of the present invention.

According to some embodiments, the antibody recognizes an antigenic determinant within the sequence:

$$G\text{-}H\text{-}R\text{-}W\text{-}X_1\text{-}X_2\text{-}G\text{-}G\text{-}X_3\text{-}V\text{-}L) \quad (\text{SEQ ID NO.: 9})$$

wherein $X_1$ is selected from Met and Leu, $X_2$ is selected from Arg and Lys, and $X_3$ is selected from Lys and Val. Each possibility represents a separate embodiment of the present invention. According to some embodiments, the antibody recognizes an antigenic determinant within a sequence selected from the group consisting of:

$$G\text{-}H\text{-}R\text{-}W\text{-}M\text{-}R\text{-}G\text{-}G\text{-}K\text{-}V\text{-}L\text{-}C; \quad (\text{SEQ ID NO.: 1})$$

$$G\text{-}H\text{-}R\text{-}W\text{-}M\text{-}R\text{-}G\text{-}G\text{-}K\text{-}V\text{-}L; \quad (\text{SEQ ID NO.: 10})$$
and $$G\text{-}H\text{-}R\text{-}W\text{-}L\text{-}K\text{-}G\text{-}G\text{-}V\text{-}V\text{-}L \quad (\text{SEQ ID NO.: 11})$$

According to specific embodiments the antibody recognizes an antigenic determinant comprising a sequence selected from the group consisting of:

$$G\text{-}H\text{-}R\text{-}W\text{-}X_1\text{-}X_2; \quad (\text{SEQ ID NO.: 3})$$

$$H\text{-}R\text{-}W\text{-}X_1\text{-}X_2\text{-}G; \quad (\text{SEQ ID NO.: 4})$$

$$R\text{-}W\text{-}X_1\text{-}X_2\text{-}G\text{-}G; \quad (\text{SEQ ID NO.: 5})$$

$$W\text{-}X_1\text{-}X_2\text{-}G\text{-}G\text{-}X_3; \quad (\text{SEQ ID NO.: 6})$$

$$X_1\text{-}X_2\text{-}G\text{-}G\text{-}X_3\text{-}V; \quad (\text{SEQ ID NO.: 7})$$

$$X_2\text{-}G\text{-}G\text{-}X_3\text{-}V\text{-}L; \quad (\text{SEQ ID NO.: 8})$$

wherein $X_1$ is selected from Met and Leu, $X_2$ is selected from Arg and Lys, and $X_3$ is selected from Lys and Val. Each possibility represents a separate embodiment of the present invention.

According to one embodiment of the present invention, the antibody is a mAb. According to a specific embodiment, the mAb is selected from the group consisting of: humanized antibody, human antibody, chimeric antibody, and an antibody fragment comprising at least the antigen-binding portion of an antibody. According to a specific embodiment, the antibody fragment is selected from the group consisting of: Fab, Fab', F(ab')$_2$, Fd, Fd', Fv, dAb, isolated CDR region, single chain antibody, "diabodies", and "linear antibodies".

According to another embodiment polyclonal antibodies to EMMPRIN which recognize an epitope within a sequence set forth in Formula I or in any one of SEQ ID NOs: 1-15 are provided.

According to some embodiments, monoclonal antibodies to EMMPRIN which recognize an epitope within a sequence set forth in Formula I or in any one of SEQ ID NOs: 1-15 are provided.

According to another embodiment, the antibodies are bispecific antibodies.

Within the scope of the present invention are also nucleic acid molecules encoding an antibody or antibody fragment or monoclonal or bispecific antibody, according to the invention, having affinity and specificity for EMMPRIN.

An antibody or antibody fragment according to the invention may be translationally linked to another protein as part of a polynucleotide molecule such as RNA or DNA. The polynucleotide sequence may be part of a recombinant viral or bacterial vector comprising said RNA or DNA molecule encoding said antibody or antibody fragment sequence.

According to this aspect, an isolated polynucleotide encoding an antibody of the invention specific to EMMPRIN, an antibody fragment thereof or a conjugate or fusion protein comprising it, is disclosed. According to a specific embodiment, the antibody specific to EMMPRIN or the antibody fragment thereof comprising at least an antigen-binding portion, recognizes an antigenic determinant comprising an epitope selected from the group consisting of:

G-H-R-W-$X_1$-$X_2$;  (SEQ ID NO.: 3)

H-R-W-$X_1$-$X_2$-G;  (SEQ ID NO.: 4)

R-W-$X_1$-$X_2$-G-G;  (SEQ ID NO.: 5)

W-$X_1$-$X_2$-G-G-$X_3$;  (SEQ ID NO.: 6)

$X_1$-$X_2$-G-G-$X_3$-V;  (SEQ ID NO.: 7)

$X_2$-G-G-$X_3$-V-L;  (SEQ ID NO.: 8)

wherein $X_1$ is selected from Met and Leu, $X_2$ is selected from Arg and Lys, and $X_3$ is selected from Lys and Val. Each possibility represents a separate embodiment of the present invention.

Vectors comprising the above polynucleotide sequences, as well as host cells, including hybridoma cells, comprising said vectors, are also within the scope of the present invention.

In another aspect the present invention is related to a pharmaceutical composition useful for preventing, attenuating or treating a disease or disorder associated with EMMPRIN expression. According to some embodiments, the pharmaceutical composition comprises a therapeutically effective amount of a peptide, a peptide multimer, fusion protein or conjugate, or encoding nucleic acid sequence or viral or bacterial vector comprising them, or an antibody or antibody fragment which specifically binds to said peptide or peptide analog; and a pharmaceutically acceptable carrier or diluent.

According to one embodiment, the pharmaceutical composition comprises a therapeutically effective amount of an antibody specific to EMMPRIN or an antibody fragment thereof comprising at least an antigen-binding portion, which recognizes an epitope selected from the group consisting of:

G-H-R-W-$X_1$-$X_2$;  (SEQ ID NO.: 3)

H-R-W-$X_1$-$X_2$-G;  (SEQ ID NO.: 4)

R-W-$X_1$-$X_2$-G-G;  (SEQ ID NO.: 5)

W-$X_1$-$X_2$-G-G-$X_3$;  (SEQ ID NO.: 6)

$X_1$-$X_2$-G-G-$X_3$-V;  (SEQ ID NO.: 7)

$X_2$-G-G-$X_3$-V-L;  (SEQ ID NO.: 8)

wherein $X_1$ is selected from Met and Leu, $X_2$ is selected from Arg and Lys, and $X_3$ is selected from Lys and Val. Each possibility represents a separate embodiment of the present invention.

According to some particular embodiments, a composition for passive immunization comprising at least one antibody or fragment thereof according to the invention is disclosed.

According to certain embodiments, the disease or disorder associated with EMMPRIN expression or activation is a cell proliferative, a hyperpermeability, an inflammatory, or an angiogenesis-related disease or disorder (including but not limited to nephrotic syndrome and acute respiratory distressed syndrome (ARDS). According to other embodiments, the cell proliferative disease or disorder is selected from the group including but not limited to: cancer, cell proliferative diseases of the eye (ocular diseases), and retinal disorders.

Retinal disorders include for example, Choroidal Neovascular Membrane (CNVM), diabetic retinopathy, macular oedema, vascular occlusion, age-related macular degeneration (AMD), and retinopathy of prematurity (ROP).

According to some embodiments, the disease or disorder associated with EMMPRIN expression or activation is a chronic inflammatory disease or an autoimmune disease, including but not limited to rheumatoid arthritis, multiple sclerosis, type-1 diabetes, type-2 diabetes, Crohn's disease, ulcerative colitis, and psoriasis. According to other embodiments, the disease is an acute inflammatory disease including but not limited to acute lung injury and sepsis. According to yet other embodiments, the disease is a heart disease (e.g., heart failure).

In yet another aspect the present invention is related to a method of preventing, attenuating or treating a disease or disorder associated with expression of EMMPRIN comprising administering to a subject in need thereof a pharmaceutical composition comprising a therapeutically effective amount of a peptide of 7-25 amino acids from the EC-I domain of EMMPRIN, a peptide analog, multimer, conjugate, fusion protein, encoding nucleic acid sequence or viral or bacterial vector thereof, or an antibody which recognizes an antigenic determinant comprising said peptide. According to some particular embodiments, the peptide, analog, multimer, conjugate or fusion protein, or the antigenic determinant recognized by said antibody is according to Formula I or comprises a sequence set forth in any one of SEQ ID NOs: 1-15.

According to some embodiments, the method comprises a combined treatment regimen of an antibody to EMMPRIN according to the invention and a peptide, analog, peptide conjugate, or fusion protein according to the invention. Such administration may be performed in a combined composition or in separate compositions administered together or at separate times.

According to some embodiments, the disease or disorder associated with expression of EMMPRIN is cell proliferative, a hyperpermeability, an inflammatory, tissue regenerative, or an angiogenesis-related disease or disorder.

According to some particular embodiments, the disease or disorder is selected from the group consisting of: cancer, cell proliferative diseases of the eye (ocular diseases), retinal disorders, and rheumatoid arthritis.

According to some embodiments, the cancer is a metastatic cancer.

According to other embodiments, the cancer is a solid cancer.

According to particular embodiments, the solid cancer is selected from the group consisting of: renal cancer, colon cancer.

According to yet another aspect, the present invention provides a method of preventing or treatment tumor metastasis comprising administering to a subject in need thereof a pharmaceutical composition comprising at least one peptide, peptide multimer, peptide conjugate, fusion protein, antibody, or antibody fragment disclosed above.

According to some embodiments the metastasis is decreased. According to other embodiments, the metastasis is prevented. According to yet other embodiments, the spread of tumors to the lungs of said subject is inhibited.

The pharmaceutical composition according to the present invention may be administered as a stand-alone treatment or in combination with a treatment with any anti-angiogenic agent. According to a specific embodiment, antibodies according to the present invention are administered to a subject in need thereof as part of a treatment regimen in conjunction with at least one anti-angiogenic agent. The pharmaceutical composition according to the present invention may be administered together with the anti-angiogenic agent or separately.

The pharmaceutical composition according to the present invention may be administered together with an anti-neoplastic composition. According to a specific embodiment, the anti-neoplastic composition comprises at least one chemotherapeutic agent. The chemotherapeutic agent, which could be administered separately or together with the antibody according to the present invention, may comprise any such agent known in the art exhibiting anti-cancer activity, including but not limited to: mitoxantrone, topoisomerase inhibitors, spindle poison vincas: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabin; podophyllotoxins: etoposide, irinotecan, topotecan, dacarbazin; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate. According to a specific embodiment, the chemotherapeutic agent is selected from the group consisting of alkylating agents, antimetabolites, folic acid analogs, pyrimidine analogs, purine analogs and related inhibitors, vinca alkaloids, epipodopyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irenotecan, oxaliplatin, capecitabine, paclitaxel and doxetaxel. Two or more chemotherapeutic agents can be used in a cocktail to be administered in combination with administration of the antibody or fragment thereof.

According to a specific embodiment, the invention provides a method of treating cancer in a subject, comprising administering to the subject effective amounts of a peptide of 7-25 amino acids from the EC-I domain of EMMPRIN, a peptide analog, multimer, fusion protein, conjugate, encoding nucleic acid sequence or viral or bacterial vector thereof or an antibody or antibody fragment which recognizes an antigenic determinant comprising said peptide. According to some embodiments the method comprises administration, in a combined treatment regimen, of a peptide according to the invention, or an analog, conjugate or fusion protein, and an antibody or fragment thereof in a combined treatment regimen. According to some particular embodiments, the peptide, analog, multimer, conjugate or fusion protein, or the antigenic determinant recognized by said antibody is according to Formula I or comprises a sequence set forth in any one of SEQ ID NOs: 1-15.

The cancer amendable for treatment by the present invention includes, but is not limited to: carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high-grade immunoblastic NHL; high-grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amendable for treatment of the invention include metastatic cancers. The method of the present invention is particularly suitable for the treatment of vascularized tumors.

In another aspect, the present invention provides a method for increasing the duration of survival of a subject having cancer, comprising administering to the subject effective amounts of a composition comprising a peptide of 7-25 amino acids from the EC-I domain of EMMPRIN, a peptide analog, multimer, fusion protein, conjugate, encoding nucleic acid sequence or viral or bacterial vector thereof, or an antibody or antibody fragment which recognizes an antigenic determinant comprising said peptide, and optionally an anti-neoplastic composition whereby the administration of the EMMPRIN peptide or antibody effectively increases the duration of survival. According to some embodiments the method comprises administration, in a combined treatment regimen, of a peptide according to the invention, or an analog, conjugate or fusion protein, and an antibody or fragment thereof. According to some particular embodiments, the peptide, analog, multimer, conjugate or fusion protein, or the antigenic determinant recognized by said antibody is according to Formula I or comprises a sequence set forth in any one of SEQ ID NOs: 1-15.

In yet another aspect, the present invention provides a method for increasing the progression free survival of a subject having cancer, comprising administering to the subject effective amounts of a composition comprising a peptide of 7-25 amino acids from the EC-I domain of EMMPRIN, a peptide analog, multimer, fusion protein, conjugate, nucleic acid sequence or viral or bacterial vector thereof or an antibody, or antibody fragment which recognizes an antigenic determinant comprising said peptide, and optionally an anti-neoplastic composition, whereby administration of the EMMPRIN peptide or antibody effectively increases the duration of progression free survival. According to some embodiments the method comprises administration, in a combined treatment regimen, of a peptide according to the invention, or an analog, conjugate or fusion protein, and an antibody or fragment thereof. According to some particular embodiments, the peptide, analog, multimer, conjugate or fusion protein, or the antigenic determinant recognized by said antibody is according to Formula I or comprises a sequence set forth in any one of SEQ ID NOs: 1-15.

Furthermore, the present invention provides a method for treating a subject having cancer, comprising administering to the subject effective amounts of a composition comprising a peptide of 7-25 amino acids from the EC-I domain of EMMPRIN, a peptide analog, multimer, fusion protein, conjugate or encoding nucleic acid sequence or viral or bacterial vector thereof or an antibody or antibody fragment which recognizes an antigenic determinant comprising said peptide an optionally anti-neoplastic composition whereby administration of the EMMPRIN peptide or antibody effectively increases the response incidence in the group of subjects. According to some embodiments the method comprises administration, in a combined treatment regimen, of a peptide according to the invention, or an analog, conjugate or fusion protein, and an antibody or fragment thereof. According to some particular embodiments, the peptide, analog, multimer, conjugate or fusion protein, or the antigenic determinant recognized by said antibody is according to Formula I or comprises a sequence set forth in any one of SEQ ID NOs: 1-15.

In yet another aspect, the present invention provides a method for increasing the duration of response of a subject having cancer, comprising administering to the subject effective amounts of a composition comprising a peptide of 7-25 amino acids from the EC-I domain of EMMPRIN, a peptide analog, multimer, fusion protein, conjugate or encoding nucleic acid sequence or viral or bacterial vector thereof or an antibody or antibody fragment which recognizes an antigenic determinant comprising said peptide and optionally an anti-neoplastic composition, wherein said anti-neoplastic composition comprises at least one chemotherapeutic agent, whereby administration of the EMMPRIN peptide or antibody effectively increases the duration of response. According to some embodiments the method comprises administration, in a combined treatment regimen, of a peptide according to the invention, or an analog, conjugate or fusion protein, and an antibody or fragment thereof. According to some particular embodiments, the peptide, analog, multimer, conjugate or fusion protein, or the antigenic determinant recognized by said antibody is according to Formula I or comprises a sequence set forth in any one of SEQ ID NOs: 1-15.

In another aspect, the invention provides a method of preventing or inhibiting development of metastasis in a patient having cancer, comprising administering to the subject effective amounts of a composition comprising a peptide of 7-25 amino acids from the EC-I domain of EMMPRIN, a peptide analog, multimer, fusion protein, conjugate or encoding nucleic acid sequence or viral or bacterial vector thereof or an antibody or antibody fragment which recognizes an antigenic determinant comprising said peptide and optionally an anti-neoplastic composition, whereby administration of the EMMPRIN peptide or antibody effectively increases the duration of response. According to some embodiments the method comprises administration, in a combined treatment regimen, of a peptide according to the invention, or an analog, conjugate or fusion protein, and an antibody or fragment thereof. According to some particular embodiments, the peptide, analog, multimer, conjugate or fusion protein, or the antigenic determinant recognized by said antibody is according to Formula I or comprises a sequence set forth in any one of SEQ ID NOs: 1-15.

In certain embodiments, various steps of the method are performed via a processor or via software executing on a computer memory or on a non-transitory computer readable medium.

Another aspect of the present invention relates to the use of an antibody specific to EMMPRIN or an antibody fragment thereof, for the manufacture of a therapeutic composition for the treatment of a cell proliferative, angiogenesis-related, or inflammatory disease or disorder.

According to another aspect, the present invention provides a pharmaceutical composition comprising a peptide of 7-25 amino acids from the EC-I domain of EMMPRIN, a peptide analog, multimer, fusion protein, conjugate or encoding nucleic acid sequence or viral or bacterial vector thereof, or an antibody or antibody fragment which recognizes an antigenic determinant comprising said peptide for treating a disorder or disease associated with expression of EMMPRIN. According to one embodiment, the disease or disorder is angiogenesis, inflammatory disease or disorder or a cell proliferative disease or disorder. According to some embodiments the pharmaceutical composition is for use in combined treatment regimen, of a peptide according to the invention, or an analog, conjugate or fusion protein, and an antibody or fragment thereof. According to some particular embodiments, the peptide, analog, multimer, conjugate or fusion protein, or the antigenic determinant recognized by said antibody is according to Formula I or comprises a sequence set forth in any one of SEQ ID NOs: 1-15.

According to some embodiments, the disease is cancer. According to particular embodiments, the cancer is a metastatic cancer.

According to another aspect, the present invention provides a method of preventing tumor recurrence comprising administering to a subject in need thereof, a peptide, peptide analog, multimer, fusion protein, conjugate, encoding nucleic acid sequence or antibody or antibody fragment or monoclonal or bispecific antibody which recognizes an antigenic determinant comprising said peptide in conjugation with surgery, radio- or chemotherapy.

According to another aspect of present invention, a method for detecting or quantifying the presence of EMMPRIN is provided. Thus, the present invention also provides methods for diagnosing conditions associated with elevated levels or upregulated expression of EMMPRIN using specific antibodies against this protein, which bind peptides comprising the newly-identified antigenic determinant. According to some embodiments, the condition associated with elevated levels or upregulated expression of EMMPRIN is a human malignant tumor selected from the group consisting of: breast, lung and bladder carcinoma, malignant melanoma, glioma and lymphoma. Diagnostic methods may be performed in-vitro or ex-vivo according to some embodiments. The antibodies according to the present invention may be also used to configure screening methods. For example, an enzyme-linked immunosorbent assay (ELISA) can be constructed for measuring levels of secreted or cell-associated polypeptide using monoclonal and polyclonal antibodies by standard methods known in the art.

According to one embodiment a method is provided for detecting or quantifying the presence of EMMPRIN, comprising the steps of:

incubating a sample with an antibody specific to EMMPRIN or an antibody fragment thereof comprising at least an antigen-binding portion;

detecting the bound EMMPRIN using a detectable probe.

According to some embodiments, the method further comprises the steps of:

comparing the amount of (ii) to a standard curve obtained from a reference sample containing a known amount of EMMPRIN via a processor; and calculating the amount of the EMMPRIN in the sample from the standard curve via a processor.

In certain embodiments, various steps of the method are performed via a processor or via software executing on a computer memory or on a non-transitory computer readable medium.

According to some particular embodiments the sample is a body fluid.

According to another embodiment, a method for diagnosing a disease or disorder associated with EMMPRIN expression is provided comprising the steps of:

incubating a biological sample with an antibody specific to EMMPRIN or an antibody fragment thereof comprising at least an antigen-binding portion;

detecting the bound EMMPRIN using a detectable probe.

According to some embodiments, the method further comprises the steps of:

comparing the amount of (ii) to a standard curve obtained from a reference sample containing a known amount of EMMPRIN;

calculating the amount of the EMMPRIN in the body fluid sample from the standard curve; and comparing the amount of (iv) to a normal EMMPRIN amount.

According to some particular embodiments the biological sample is a body fluid.

According to some particular embodiments, the antigenic determinant recognized by said antibody is contained in a sequence according to Formula I or in a sequence set forth in any one of SEQ ID NOs: 1-15.

Further embodiments and the full scope of applicability of the present invention will become apparent from the detailed description given hereinafter.

BRIEF DESCRIPTION OF THE FIGURES

FIG. 5B) or TRAMP-C2 tumor cells ($0.5 \times 10^6$ each, n=10, FIG. 5A) were incubated in co-culture for 48 h with five-fold serial dilutions of either immune or pre-immune serum. VEGF and MMP-9 concentrations in the supernatants were determined by ELISA. *, $p<0.05$, **, $p<0.01$ relative to co-culture without addition of sera.

FIG. 10 161-MAP injections raise immunological memory. Mice that had fully regressed tumors after MAP treatment (as described in FIG. 8) were re-challenged with an additional s.c. injection of $2\times10^6$ CT26 cells 3 weeks after the conclusion of the previous experiment. The adjuvant group received three boost injections of CFA and IFA to their footpad every 7 days before receiving the CT26 tumor cell injection. ***, $p<0.001$ relative to all MAP-treated mice.

FIGS. 11A-11B 161-MAP raise immunological memory that prevents metastases. Mice that were s.c. re-challenged with CT26 cells injected to their flanks and did not develop any tumors (10 months old) were i.v. injected in their tail vein with $10^6$ CT26 cells in 200 µl PBS. As control groups young mice (8 weeks old) or old mice (10 months old) were injected with three boost injections of 50 µg of the scrambled-MAP in 30 µl of CFA and then IFA to their footpad every 7 days, and after an additional 7 days were injected with $10^6$ CT26 cells in 200 µl PBS to their tail vein. After 15 days the mice were euthanized. FIG. 11A) lungs were removed and the number of metastases was counted under a dissecting microscope. FIG. 11B) lungs were dried on a blotting paper and weighed.

FIG. 12A) a representative image of lungs from mice injected with CT26 cells and receiving 50 µg of the scrambled MAP or 75 µg of 161-MAP; FIG. 12B) the number of metastatic foci in mice injected with CT26 cells; FIG. 12C) lung weight of mice injected with CT26 cells. FIG. 12D) a representative image of lungs from mice injected with RENCA cells and receiving either 50 µg of the scrambled MAP or 50 µg of 161-MAP; FIG. 12E) the number of metastatic foci in mice injected with RENCA cells; FIG. 12F) Lung weight of mice injected with RENCA cells.

DETAILED DESCRIPTION OF THE INVENTION

Figure 1:
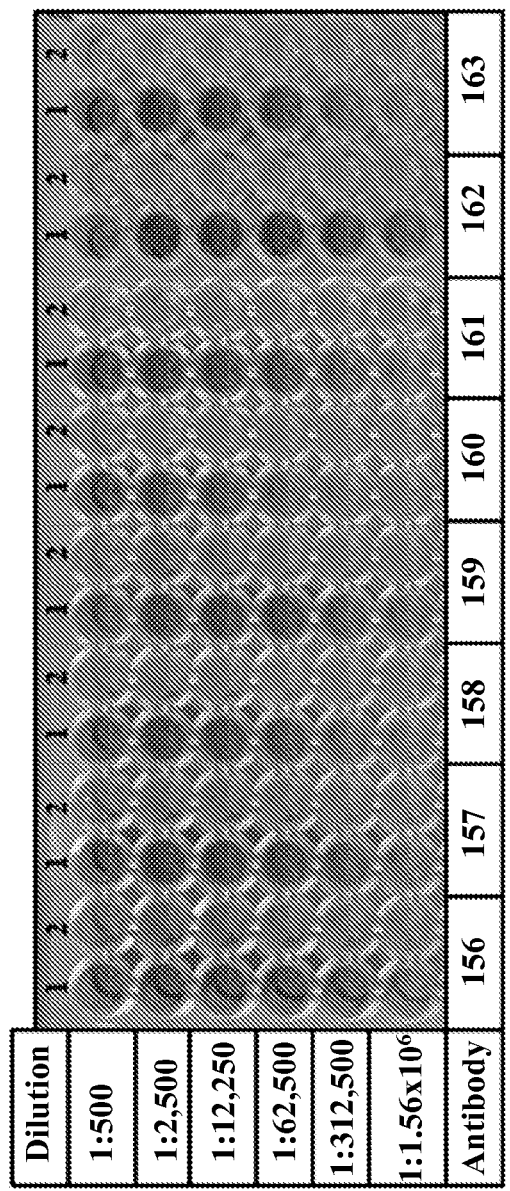
FIG. 1 Determination of titer and specificity of the polyclonal antibodies in sera obtained from immunized rabbits. The plates were coated either with the different peptides conjugated to BSA (strips marked 1), or with BSA alone (strips marked 2). Sera were serially diluted for assay as indicated.

The present invention provides EMMPRIN peptides and EMMPRIN-binding antibodies which reduce levels of MMP-9 and VEGF in vitro and inhibit tumor growth in vivo. The results support the important role of EMMPRIN in mediating tumor cell—macrophage interactions that shape the tumor microenvironment and lead to increased angiogenesis and metastasis through the secretion of MMP-9 and VEGF. Moreover, the results suggest that both the antibody and the branched peptide used to exemplify the invention could be used for immunotherapy strategies designed to inhibit tumor growth. Immunization with EMMPRIN peptide results in total tumor regression and metastasis spread, and the generation of immunological memory may be used in conjugation with surgery, radio- or chemotherapy to prevent tumor recurrence.

The EMMPRIN peptide-based vaccination demonstrated herein can be considered as a therapeutic vaccination, as it both reduced tumor progression and also regressed and cured tumors. The vaccination also evoked persistent immune memory that was effective in preventing tumor remission up to 11 months after the initial immunization was delivered. An exemplary rabbit anti-mouse polyclonal antibody directed against a specific antigenic determinant located in the extracellular domain (EC-I or D-I) region of EMMPRIN has been produced and used to demonstrate that:

EMMPRIN is up-regulated in macrophage-tumor cell co-cultures in vitro, leading to increased MMP-9 and VEGF;

The polyclonal anti-EMMPRIN antibody inhibits VEGF and MMP-9 in vitro, and inhibits tumor growth in vivo when administered to mice with palpable tumors;

The same peptide used for immunization, synthesized as a branched multi-antigenic peptide (MAP), stimulates an immune response that inhibits tumor growth when administered to the footpad of mice bearing tumors, and even causes regression of some of the tumors;

The active immunization response to the MAP peptide construct triggers immunological memory, as mice with regressed tumors do not develop new tumors when re-challenged with tumor cell injection.

Since the ability to induce VEGF was not yet associated with any domain or sequence of EMMPRIN, and since the EC-I domain and the extent of its glycosylation of EMMPRIN were associated with induction of MMP-9 (Ku et al., Ibid), these domains were selected for epitope mapping using antibodies. The antibodies were generated against the distal domain (EC-0, antibodies #156-160), which is unique to the long EMMPRIN isoform, to the EC-I domain (antibodies #161 and #163), and to the EC-II domain (antibody #162). The inability of all antibodies, except antibody #161, to inhibit secretion either MMP-9 or VEGF rules out the involvement of these epitopes in the induction of these two mediator proteins. Only antibody #161 inhibited secretion both MMP-9 and VEGF in TRAMP-C2 and CT26 co-cultures with RAW 264.7 macrophages.

Additionally, the same antibody #161 inhibited MMP-9 and VEGF secretion in the human tumor cell-macrophage co-cultures in vitro, suggesting that the antibody can cross-react with the human epitope of EMMPRIN, even though the short sequence is not fully homologous to the human species and differs by 3 amino acids. A recent study (Ku et al., ibid.) showed that a stretch of 28 amino acids (residues 22-50 of the short isoform) was responsible for MMP production and invasiveness of EMMPRIN-transfected COS-7 cells. However, antibody #161 is raised against a short 11-amino-acid epitope in the EC-I domain just downstream of the sequence mentioned, and only seven amino acids downstream of the N-linked glycosylation site that is considered crucial for the MMP-stimulating activity. Additionally, the importance of glycosylation was recently demonstrated by the ability of synthesized EC-I peptide conjugated to a chitobiose unit which starts N-glycosylation, but not the EC-I peptide alone, to stimulate MMP-2 production in fibroblasts (Kawakami et al. ibid). Synthetic EMMPRIN peptides with chitobiose substitution stimulate MMP-2 production by fibroblasts. The sequence of peptide #161 was therefore identified as the antigenic determinant and epitope responsible for both VEGF and MMP-9 induction. Without wishing to be bound to any theory or mechanism of action, it is proposed that binding of antibody #161 confers a steric interference with the glycosylated asparagine residue located 7 amino acid upstream of this epitope and that the ability of antibody #161 to inhibit both MMP-9 and VEGF induction may reflect the binding of EMMPRIN to a single receptor that is responsible for initiating a signaling pathway culminating in the induction of both proteins.

In conclusion, the results identify EMMPRIN as a key molecule that is crucial to tumor progression and to the interaction of tumor cells with stromal cells, particularly macrophages. It is shown that the antibody according to the present invention inhibited MMP-9 and VEGF secretion in vitro, and that injection of either the antibody or the branched peptide inhibited tumor progression in vivo.

Inflammatory Diseases

All inflammatory diseases require cell movement through the ECM. In particular, leukocytes must migrate from the blood vessels through the basement membrane (BM) and the ECM to get to the inflammatory site. This requires degradation or remodeling of the ECM and BM, which involves MMPs, including MMP-9. Additionally, many inflammatory diseases require new or additional blood supply to the inflammatory site, because the increased number of cells in the leukocyte infiltrate have higher metabolic demands that require more oxygen and nutrients. Thus, angiogenesis (which is a process that involves secretion of pro-angiogenic factors such as VEGF) is initiated in many inflammatory diseases, especially in chronic inflammatory diseases.

EMMPRIN peptides and binding antibodies according to the invention are disclosed for use in the diagnosis, immunotherapy and vaccination of inflammatory diseases, especially those where increased levels of EMMPRIN, MMPs or VEGF were detected. For example, chronic inflammatory diseases, autoimmune diseases (e.g. rheumatoid arthritis, multiple sclerosis, type-1 diabetes, Crohn's disease); cancerous diseases (e.g., breast, colon, prostate, gastric, etc.); Heart diseases (e.g., heart failure); acute inflammatory diseases (e.g., acute lung injury, sepsis).

Definitions

"Derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it, and do not adversely affect the immunogenic properties thereof.

These derivatives may include, for example, aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups), or O-acyl derivatives of free hydroxyl group (e.g., that of seryl or threonyl residues) formed by reaction with acyl moieties.

The term "analog" further indicates a molecule which has the amino acid sequence according to the invention except for one or more amino acid changes. Analogs according to the present invention may comprise also peptidomimetics. "Peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with another covalent bond. A peptidomimetic according to the present invention may optionally comprise at least one bond which is an amide-replacement bond such as urea bond, carbamate bond, sulfonamide bond, hydrazine bond, or any other covalent bond. The design of appropriate "analogs" may be computer assisted. Analogs are included in the invention as long as they remain pharmaceutically acceptable.

Reference to a particular peptide or "analog" includes the naturally occurring peptide sequence or a peptide that has the substantially the same activity as the naturally occurring sequence. "Peptides" of the invention also include modified peptides (with amino acid substitutions, both conservative and non-conservative as described below) that have the same or improved activity as a wild-type or unmodified peptide. "Salts" of the peptides of the invention contemplated by the invention are physiologically and pharmaceutically acceptable organic and inorganic salts.

The amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation.

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. These substitutions may enhance oral bioavailability, penetration into the islets, targeting to specific beta cell populations, immunogenicity, and the like. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The peptide of present invention may be produced by any method known in the art, including recombinant and synthetic methods. Synthetic methods include exclusive solid phase synthesis, partial solid phase synthesis, fragment condensation, or classical solution synthesis. Solid phase peptide synthesis procedures are well known to one skilled in the art and described, for example by John Morrow Stewart and Janis Dillaha Young, Solid Phase Polypeptide Syntheses (2nd Ed., Pierce Chemical Company, 1984). In some embodiments, synthetic peptides are purified by preparative high performance liquid chromatography (Creighton T. (1983) Proteins, structures and molecular principles. WH Freeman and Co. N.Y.) and the peptide sequence is confirmed via amino acid sequencing by methods known to one skilled in the art.

In some embodiments, recombinant protein techniques are used to generate the peptide of the present invention. In some embodiments, recombinant protein techniques are used for generation of relatively long polypeptides (typically longer than 18 amino acids) or nucleic acid sequences or viral or bacterial vectors for vaccine formulation. Recombinant techniques are described for example by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

An "antigen" is a molecule or a portion of a molecule capable of eliciting antibody formation and being bound by an antibody. An antigen may have one or more than one epitope. The specific reaction referred to above is meant to indicate that the antigen will react, in a highly specific manner, with its corresponding antibody and not with the multitude of other antibodies which may be evoked by other antigens. An antigen according to the present invention is an agonistic form of VEGF or a fragment thereof.

The term "antigenic determinant" or "epitope" according to the invention refers to the region of an antigen molecule that specifically reacts with a particular antibody.

The term "viral vector" or "bacterial vector" refers to a virus or bacteria, respectively, which can be administered to a human host without causing any disease or pathology and which encodes a protein or peptide or epitope not present in the native virus of bacteria. Such viral and bacterial vectors can be readily produced by recombinant methods well known in the art. Non-limiting examples include poxviruses, adenoviruses, alphaviruses, lentiviruses, *Listeria monocytogenes, Salmonella typhi, Vibrio cholerae, Shigella sonnei, Mycobacterium bovis*, and *Bacillus anthracis*.

The term "nucleic acid" in the context of vaccine refers to the injection of DNA to the host, whereby DNA is taken up by cells, transcribed and translated to protein or peptide that is presented to the immune system and thus elicit antibody- and cell-based immune responses specific to the peptide of interest. Non-limiting examples of such nucleic acid vaccines are purified nucleic acid administered alone, DNA-liposome complexes, DNA-coated polymers, and metal-coated DNA.

Antibodies, or immunoglobulins, comprise two heavy (H) chains linked together by disulfide bonds and two light (L) chains, each L chain being linked to a respective H chain by disulfide bonds in a "Y" shaped configuration. Proteolytic digestion of an antibody yields Fv (Fragment variable) and Fc (fragment crystalline) domains. The antigen binding domains, Fab's, include regions where the polypeptide sequence varies. The term $F(ab')_2$ represents two Fab' arms linked together by disulfide bonds. The central axis of the antibody is termed the Fc fragment. Each H chain has at its N-terminal end a variable (V) domain ($V_H$) followed by a number of constant (C) domains ($C_H$). Each L chain has a V domain ($V_L$) at one end and a C domain ($C_L$) at its other end, the $V_L$ domain being aligned with the $V_H$ domain and the $C_L$ domain being aligned with the first $C_H$ domain ($C_H1$). The V domains of each pair of L and H chains form the antigen-binding site. The domains on the L and H chains have the same general structure, and each domain comprises four framework regions (FRs), whose sequences are relatively conserved, joined by three hypervariable domains known as complementarity determining regions (CDR1-3). These domains contribute specificity and affinity of the antigen-binding site. The isotype of the H chain (gamma-γ, alpha-α, delta-δ, epsilon-ϵ or mu-μ) determines immunoglobulin class (IgG, IgA, IgD, IgE or IgM, respectively). There are several subtypes of IgG (IgG1, IgG2, IgG3, and IgG4). The L chain is either of two isotypes (kappa, κ or lambda, λ) found in all antibody classes.

The term "antibody" is used in the broadest sense and includes mAbs (including full-length or intact mAbs), polyclonal antibodies, multivalent antibodies, multi-specific antibodies (e.g., bispecific antibodies), and antibody fragments so long as they exhibit the desired biological activity.

The antibody according to the present invention is a molecule comprising at least the antigen-binding portion of an antibody. Antibody or antibodies according to the invention include intact antibodies, such as polyclonal antibodies or mAbs, as well as proteolytic fragments thereof such as Fab or $F(ab')_2$ fragments. Further included within the scope of the invention are chimeric antibodies; human and humanized antibodies; recombinant and engineered antibodies, bi-specific antibodies, and fragments thereof. Furthermore, the DNA encoding the V region of the antibody can be inserted into the DNA encoding the C regions of other antibodies to produce chimeric antibodies. Single chain antibodies also fall within the scope of the present invention.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the $C_H1$ domain; (v) the Fv fragment having the $V_L$ and $V_H$ domains of a single arm of an antibody; (vi) the dAb fragment (Ward et al., Nature 1989, 341, 544-546) which consists of a $V_H$ domain; (vii) isolated CDR regions; (viii) $F(ab')_2$ fragments, a bivalent fragment including two Fab' fragments linked by a disulfide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a $V_H$ domain connected to a $V_L$ domain in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments ($V_H$-$C_H1$-$V_H$-$C_H1$) which, together with complementary L chain polypeptides, form a pair of antigen binding regions (Zapata et al. Protein Eng., 1995, 8, 1057-1062; and U.S. Pat. No. 5,641,870).

Single-chain antibodies can be single-chain composite polypeptides having antigen binding capabilities and comprising amino acid sequences homologous or analogous to $V_H$ and $V_L$, i.e., linked $V_H$-$V_L$ or single-chain Fv (scFv).

A "neutralizing antibody" as used herein refers to a molecule having an antigen-binding site to a specific receptor or ligand target capable of reducing or inhibiting (blocking) activity or signaling through a receptor, as determined by in vivo or in vitro assays, as per the specification.

The term "monoclonal antibody" as used herein refers to an antibody obtained from a population of substantially homogeneous antibodies, i.e., the individual antibodies comprising the population are identical except for possible naturally occurring mutations that may be present in minor amounts. MAbs are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method. mAbs may be obtained by methods known to those skilled in the art. For example, the mAbs to be used in accordance with the present invention may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example. The mAbs may be isolated from a library from human lymphocytes and selected according to their specificity.

The mAbs of the present invention may be of any immunoglobulin class including IgG, IgM, IgE, IgA, and any subclass thereof. A hybridoma producing a mAb may be cultivated in vitro or in vivo. High titers of mAbs can be obtained by production in recombinant mammalian cells that contain the nucleic acids encoding the H and L chains of the mAb under the control of a cell-specific promoter. Such recombinant expresser cells are cultivated in large volumes in bioreactors. mAbs of any isotype are purified from culture supernatants, using filtration and column chromatography methods well known to those of skill in the art.

The mAbs herein specifically include "chimeric" antibodies in which a portion of the H and/or L chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). In addition, CDR grafting may be performed to alter certain properties of the antibody molecule including affinity or specificity. A non-limiting example of CDR grafting is disclosed in U.S. Pat. No. 5,225,539.

Chimeric antibodies are molecules, the different portions of which are derived from different animal species, such as those having a variable region derived from a murine mAb and a human C region. Antibodies which have V region FR residues substantially from human antibody (termed an acceptor antibody) and CDRs substantially from a mouse antibody (termed a donor antibody) are also referred to as humanized antibodies. Chimeric antibodies are primarily used to reduce immunogenicity in application and to increase yields in production, for example, where murine mAbs have higher immunogenicity in humans (HAMA, which is human anti-mouse antibody response), such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from CDRs of the recipient are replaced by residues from CDRs of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in either the recipient antibody or in the donor antibody. These modifications are made to further refine antibody performance, specificity, affinity and reduced immunogenicity. In general, the humanized antibody will comprise substantially all of at least one, and typically two, V domains, in which all or substantially all of the CDR loops correspond to those of a non-human immunoglobulin and all or substantially all of the FRs are those of a human immunoglobulin sequence. The humanized antibody optionally will also comprise at least a portion of an immunoglobulin C region (Fc), typically that of a human immunoglobulin in order to provide for a full mAb and appropriate effector functions as desired. For further details, see Jones et al., Nature 1986, 321, 522-525; Riechmann et al., Nature 1988, 332, 323-329; and Presta, Curr. Op. Struct. Biol., 1992 2, 593-596.

A "human antibody" is one which possesses an amino acid sequence which corresponds to that of an antibody produced by a human and/or encoded by the human genome and/or has been made using any of the techniques for making human antibodies as disclosed herein. This definition of a human antibody specifically excludes a humanized antibody comprising non-human CDR residues. Human antibodies can be produced using various techniques known in the art. In one embodiment, the human antibody is selected from a phage library, where that phage library expresses human antibodies (Vaughan et al. Nature Biotechnology 1996 14,309-314; Sheets et al. PNAS (USA), 1998, 95, 6157-6162); Hoogenboom and Winter, J. Mol. Biol., 1991, 227, 381; Marks et al., J. Mol. Biol., 1991, 222, 581). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B lymphocytes producing an antibody directed against a target antigen (such B lymphocytes may be recovered from an individual or may have been immunized in vitro) followed by screening with the antigen of interest for a specific antibody.

By the term "single-chain variable fragment (scFv)" is meant a fusion of the $V_H$ and $V_L$ regions, linked together with a short (usually serine, glycine) linker. Single-chain antibodies can be single chain composite polypeptides having antigen binding capabilities and comprising amino acid sequences homologous or analogous to $V_H$ and $V_L$ VL (linked $V_H$-$V_L$ or single chain Fv (scFv)). Both $V_H$ and $V_L$ may copy natural mAb sequences or one or both of the chains may comprise a CDR-FR construct of the type described in U.S. Pat. No. 5,091,513, the entire contents of which are incorporated herein by reference. The separate polypeptides analogous to the $V_H$ and $V_L$ regions are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are incorporated herein by reference.

A "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific mini-antibodies (see Muller et al., 1998) and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

Antibodies according to the invention can be obtained by administering the EMMPRIN peptides, analogs, or cells expressing these, to an animal, preferably a nonhuman, using routine protocols. For preparation of mAbs, any technique known in the art that provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in Monoclonal Antibodies And Cancer Therapy, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant mAbs one can use various methods all based on display libraries to generate a large pool of antibodies with different antigen recognition sites. Such a library can be made in several ways: One can generate a synthetic repertoire by cloning synthetic CDR regions in a pool of H chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human CDRs are inserted into a human antibody or consensus antibody FR sequence. Further changes can then be introduced into the antibody framework to modulate affinity or immunogenicity.

For example, U.S. Pat. No. 5,585,089 of Queen et al. discloses a humanized immunoglobulin and methods of preparing same, wherein the humanized immunoglobulin comprises CDRs from a donor immunoglobulin and $V_H$ and $V_L$ region FRs from human acceptor immunoglobulin H and L chains, wherein said humanized immunoglobulin comprises amino acids from the donor immunoglobulin FR outside the Kabat and Chothia CDRs, wherein the donor amino acids replace corresponding amino acids in the acceptor immunoglobulin H or L chain frameworks.

U.S. Pat. No. 5,225,539, of Winter, also discloses an altered antibody or antigen-binding fragment thereof and methods of preparing same, wherein a V domain of the antibody or antigen-binding fragment has the FRs of a first immunoglobulin H or L chain V domain and the CDRs of a second immunoglobulin $V_H$ or $V_L$ domain, wherein said second immunoglobulin $V_H$ or $V_L$ domain is different from said first immunoglobulin $V_H$ or $V_L$ domain in antigen binding specificity, antigen binding affinity, stability, species, class or subclass.

Anti-idiotype antibodies specifically immunoreactive with an antibody of the invention are also comprehended.

Techniques for the production of single-chain antibodies (U.S. Pat. No. 4,946,778) can be adapted to produce single-chain antibodies to polypeptides or polynucleotides of this invention. Also, transgenic mice, or other organisms such as other mammals, can be used to express humanized antibodies specific to the polypeptides or polynucleotides of the invention.

Alternatively, phage display technology can be utilized to select antibody genes with binding activities towards a polypeptide of the invention either from repertoires of PCR amplified v-genes of lymphocytes from humans screened for possessing anti-VEGF or from libraries (McCafferty, et al., (1990), Nature 348, 552-554; Marks, et al., (1992) Biotechnology 10, 779-783). The affinity of these antibodies can also be improved by, for example, chain shuffling (Clackson et al., (1991) Nature 352:628).

The above-described antibodies can be employed to isolate or to identify clones expressing the polypeptides to purify the polypeptides by, for example, affinity chromatography.

The invention also provides conservative amino acid variants of the peptides and antibody molecules according to the invention. Variants according to the invention also may be made that conserve the overall molecular structure of the encoded proteins or peptides. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Humanized and Human Antibodies

A humanized antibody, typically has a human FR grafted with non-human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human V domain has been substituted by the corresponding sequence from a non-human species. In practice, humanized antibodies are typically human antibodies in which some CDR residues and possibly some FR residues are substituted by residues from analogous sites in rodent antibodies.

The choice of human $V_H$ and $V_L$ domains to be used in making the humanized antibodies is very important for reducing immunogenicity. According to the so-called "best-fit" method, the sequence of the V domain of a rodent antibody is screened against the entire library of known human-domain sequences. The human sequence which is closest to that of the rodent is then accepted as the human FR for the humanized antibody (Sims et al., J. Immunol., 151:2296 (1993); Chothia et al., J. Mol. Biol., 196:901 (1987)). Another method uses a particular FR derived from the consensus sequence of all human antibodies of a particular subgroup of H or L chains. The same FR may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high specificity and affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992). Human antibodies can also be derived from phage-display libraries (Hoogenboom et al., J. Mol. Biol., 227:381 (1991); Marks et al., J. Mol. Biol., 222:581-597 (1991); Vaughan et al. Nature Biotech 14:309 (1996)).

Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv).

A "disorder" is any condition that would benefit from treatment with a peptide or an antibody according to the invention. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic, immunologic disorders or hyperpermeability states.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) local cancer cell growth, inhibit cancer cell infiltration into peripheral organs; inhibit tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

"Treatment" refers to both therapeutic treatment and prophylactic or preventative measures. Those in need of treatment include those already with the disorder as well as those in which the disorder is to be prevented.

Therapeutic Vaccination or Immunotherapy:

Several options exist in cancer immunotherapies. The prevalent one is the use of repeated boost injections of antibodies directed against tumor antigens or proteins that play a major role in tumor promotion. Examples of such treatments are the use of anti-VEGF (Avastin™) or anti-Her2/neu (Herceptin™). This passive immunization strategy employs the effector functions of antibodies that may target tumor cells and tag them for destruction (e.g. complement, macrophages, ADCC), or inhibit protein activity (e.g. blocking of angiogenesis). However, it circumvents the full activation of the immune response and the generation of immune memory.

In contrast, active vaccination strategies rely on presentation of the antigenic determinant to T cells, activating both the innate and adaptive arms of the immune response, and generating immune memory. Today, vaccinations against tumor antigens use injections of tumor cell lysates, genetically modified tumor cells, dendritic cells loaded with the antigen, purified proteins or other macromolecules, or the recently developed peptide-based vaccinations. Most such vaccination strategies also employ an adjuvant to enhance the potency of the immune response.

Vaccines are most commonly used as prophylactic agents, to prevent or dampen the deleterious effect of a future infection with the desire to maintain prolonged protection. However, vaccines may also be used therapeutically, to treat an existing disease, and since they evoke an immune response, they may also provide lasting protection. Thus, the term therapeutic vaccination was coined. Several examples of cancer therapeutic vaccination can be found (Gonzalez G et al. Curr. Cancer Drug targets 2011 Jan.; 11(1):103-10; Van Poppel H et al., Eur. Urol. 2009 Jun.; 55(6):1333-42; Berge G, et al. Cancer Immunol. Immunother. 2010 Aug.; 59(8): 1285-94). Therapeutic vaccination may prevent the progression of an existing disease, or may reverse the disease.

Therapeutic vaccination and passive immunization may be combined to a single treatment regimen.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" refers to a composition useful in treating cancer comprising at least one active therapeutic agent capable of inhibiting or preventing tumor growth or function or metastasis, and/or causing destruction of tumor cells. Therapeutic agents suitable in an anti-neoplastic composition for treating cancer include, but not limited to, chemotherapeutic agents, radioactive isotopes, toxins, cytokines such as interferons, and antagonistic agents targeting cytokines, cytokine receptors or antigens associated with tumor cells. For example, therapeutic agents useful in the present invention can be antibodies such as anti-HER2 antibody and anti-CD20 antibody, or small molecule tyrosine kinase inhibitors such as VEGF receptor inhibitors and EGF receptor inhibitors. Preferably the therapeutic agent is a chemotherapeutic agent.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy DNA-based vaccines, for example, ALLOVECTIN® vaccine, LEUVECTIN™ vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Pharmacology

The present invention also contemplates pharmaceutical formulations or compositions for human medical use. According to some embodiments the pharmaceutical compositions are vaccine compositions, which comprise as the active agent at least one EMMPRIN peptide, peptide analog, multimer or conjugate.

Vaccine Formulations

Vaccine compositions according to the present invention comprise at least one peptide, peptide analog or conjugate or fusion protein comprising it, and optionally, an adjuvant. Formulation can contain a variety of additives, such as adjuvant, excipient, stabilizers, buffers, or preservatives. The vaccine can be formulated for administration in one of many different modes.

In some embodiments, the vaccine is formulated for parenteral administration, for example intramuscular or subcutaneous administration. According to yet another embodiment the administration is intradermal. Needles specifically designed to deposit the vaccine intradermally are known in the art as disclosed for example in U.S. Pat. Nos. 6,843,781 and 7,250,036 among others. According to other embodiments the administration is performed with a needleless injector.

According to one embodiment of the invention, the vaccine is administered intranasally. The vaccine formulation may be applied to the lymphatic tissue of the nose in any convenient manner. However, it is preferred to apply it as a liquid stream or liquid droplets to the walls of the nasal passage. The intranasal composition can be formulated, for example, in liquid form as nose drops, spray, or suitable for inhalation, as powder, as cream, or as emulsion.

The formulation of these modalities is general knowledge to those with skill in the art.

Liposomes provide another delivery system for antigen delivery and presentation. Liposomes are bilayered vesicles composed of phospholipids and other sterols surrounding a typically aqueous center where antigens or other products can be encapsulated. The liposome structure is highly versatile with many types range in nanometer to micrometer sizes, from about 25 nm to about 500 µm. Liposomes have been found to be effective in delivering therapeutic agents to dermal and mucosal surfaces. Liposomes can be further modified for targeted delivery by for example, incorporating specific antibodies into the surface membrane, or altered to encapsulate bacteria, viruses or parasites. The average survival time or half-life of the intact liposome structure can be extended with the inclusion of certain polymers, for example polyethylene glycol, allowing for prolonged release in vivo. Liposomes may be unilamellar or multilamellar. Method for encapsulation of antigens in liposomes are well known in the art.

Microparticles and nanoparticles employ small biodegradable spheres which act as depots for vaccine delivery and can be also used to deliver the vaccine formulations of the present invention. The major advantage that polymer microspheres possess over other depot-effecting adjuvants is that they are extremely safe and have been approved by the Food and Drug Administration in the US for use in human medicine as suitable sutures and for use as a biodegradable drug delivery system (Langer R. Science. 1990; 249(4976): 1527-33). The rates of copolymer hydrolysis are very well characterized, which in turn allows for the manufacture of microparticles with sustained antigen release over prolonged periods of time (O'Hagen, et al., Vaccine. 1993; 11(9):965-9).

Parenteral administration of microparticles elicits long-lasting immunity, especially if they incorporate prolonged release characteristics. The rate of release can be modulated by the mixture of polymers and their relative molecular weights, which will hydrolyze over varying periods of time. Without wishing to be bound to theory, the formulation of different sized particles (1 µm to 200 µm) may also contribute to long-lasting immunological responses since large particles must be broken down into smaller particles before being available for macrophage uptake. In this manner a single-injection vaccine could be developed by integrating various particle sizes, thereby prolonging antigen presentation and greatly benefiting livestock producers.

In some applications an adjuvant or excipient may be included in the vaccine formulation. Montanide™ (Incomplete Freund's adjuvant) and alum for example, are preferred adjuvants for human use. The choice of the adjuvant will be determined in part by the mode of administration of the vaccine. A preferred mode of administration is intramuscular administration. Another preferred mode of administration is intranasal administration. Non-limiting examples of intranasal adjuvants include chitosan powder, PLA and PLG microspheres, QS-21, AS02A, calcium phosphate nanoparticles (CAP); mCTA/LTB (mutant cholera toxin E112K with pentameric B subunit of heat labile enterotoxin), and detoxified E. Coli derived labile toxin.

The adjuvant used may also be, theoretically, any of the adjuvants known for peptide- or protein-based vaccines. For example: inorganic adjuvants in gel form (aluminium hydroxide/aluminium phosphate); bacterial adjuvants such as monophosphoryl lipid A and muramyl peptides; particulate adjuvants such as the so-called ISCOMS ("immunostimulatory complexes"), liposomes and biodegradable microspheres; adjuvants based on oil emulsions and emulsifiers such as IFA ("Incomplete Freund's adjuvant"), SAF, saponines (such as QS-21), squalene/squalane; synthetic adjuvants such as non-ionic block copolymers, muramyl peptide analogs, synthetic lipid A, synthetic polynucleotides and polycationic adjuvants.

Adjuvants for use with immunogens of the present invention include aluminum or calcium salts (for example hydroxide or phosphate salts). A particularly preferred adjuvant for use herein is an aluminum hydroxide gel such as Alhydrogel™. Calcium phosphate nanoparticles (CAP) is an adjuvant being developed by Biosante, Inc (Lincolnshire, Ill.). The immunogen of interest can be either coated to the outside of particles, or encapsulated inside on the inside (He et al 2000, Clin. Diagn. Lab. Immunol., 7(6):899-903).

Another adjuvant for use with an immunogen of the present invention is an emulsion. A contemplated emulsion can be an oil-in-water emulsion or a water-in-oil emulsion. In addition to the immunogenic chimer protein particles, such emulsions comprise an oil phase of squalene, squalane, peanut oil or the like as are well known, and a dispersing agent. Non-ionic dispersing agents are preferred and such materials include mono- and di-$C_{12}$-$C_{24}$-fatty acid esters of sorbitan and mannide such as sorbitan mono-stearate, sorbitan mono-oleate and mannide mono-oleate.

Such emulsions are for example water-in-oil emulsions that comprise squalene, glycerol and a surfactant such as mannide mono-oleate (Arlacel™ A), optionally with squalane, emulsified with the chimer protein particles in an aqueous phase. Alternative components of the oil-phase include alpha-tocopherol, mixed-chain di- and tri-glycerides, and sorbitan esters. Well-known examples of such emulsions include Montanide™ ISA-720, and Montanide™ ISA 703 (Seppic, Castres, France. Other oil-in-water emulsion adjuvants include those disclosed in WO 95/17210 and EP 0 399 843.

The use of small molecule adjuvants is also contemplated herein. One type of small molecule adjuvant useful herein is a 7-substituted-8-oxo- or 8-sulfo-guanosine derivative described in U.S. Pat. Nos. 4,539,205, 4,643,992, 5,011,828 and 5,093,318. 7-allyl-8-oxoguanosine(loxoribine) has been shown to be particularly effective in inducing an antigen-(immunogen-) specific response.

A useful adjuvant includes monophosphoryl lipid A (MPL®), 3-deacyl monophosphoryl lipid A (3D-MPL®), a well-known adjuvant manufactured by Corixa Corp. of Seattle, formerly Ribi Immunochem, Hamilton, Mont. The adjuvant contains three components extracted from bacteria: monophosphoryl lipid (MPL) A, trehalose dimycolate (TDM) and cell wall skeleton (CWS) (MPL+TDM+CWS) in a 2% squalene/Tween™ 80 emulsion. This adjuvant can be prepared by the methods taught in GB 2122204B.

Other compounds are structurally related to MPL® adjuvant called aminoalkyl glucosamide phosphates (AGPs) such as those available from Corixa Corp under the designation RC-529™ adjuvant {2-[(R)-3-tetra-decanoyloxytetradecanoylamino]-ethyl-2-deoxy-4-O-phosphon-o-3-O-[(R)-3-tetradecanoyloxytetra-decanoyl]-2-[(R)-3-tetradecanoyloxytet-radecanoyl-amino]-p-D-glucopyranoside triethylammonium salt}. An RC-529 adjuvant is available in a squalene emulsion sold as RC-529SE and in an aqueous formulation as RC-529AF available from Corixa Corp. (see, U.S. Pat. Nos. 6,355,257 and 6,303,347; 6,113,918; and U.S. Publication No. 03-0092643).

Further contemplated adjuvants include synthetic oligonucleotide adjuvants containing the CpG nucleotide motif one or more times (plus flanking sequences) available from Coley Pharmaceutical Group. The adjuvant designated QS21, available from Aquila Biopharmaceuticals, Inc., is an immunologically active saponin fractions having adjuvant activity derived from the bark of the South American tree Quillaja Saponaria Molina (e.g. Quil™ A), and the method of its production is disclosed in U.S. Pat. No. 5,057,540. Derivatives of Quil™ A, for example QS21 (an HPLC purified fraction derivative of Quil™ A also known as QA21), and other fractions such as QA17 are also disclosed. Semi-synthetic and synthetic derivatives of Quillaja Saponaria Molina saponins are also useful, such as those described in U.S. Pat. Nos. 5,977,081 and 6,080,725. The adjuvant denominated MF59 available from Chiron Corp. is described in U.S. Pat. Nos. 5,709,879 and 6,086,901.

Muramyl dipeptide adjuvants are also contemplated and include N-acetyl-muramyl-L-threonyl-D-isoglutamine (thur-MDP), N-acetyl-nor-muramyl-L-alanyl-D-isoglutamine [CGP 11637, referred to as nor-MDP], and N-acetyl-muramyl-L-alanyl-D-isoglutaminyl-L-alanine-2-(1'-2'-dipalmityol-s-n-glycero-3-hydroxyphosphoryloxy)ethylamine [(CGP) 1983A, referred to as MTP-PE]. The so-called muramyl dipeptide analogues are described in U.S. Pat. No. 4,767,842.

Other adjuvant mixtures include combinations of 3D-MPL and QS21 (EP 0 671 948 B1), oil-in-water emulsions comprising 3D-MPL and QS21 (WO 95/17210, PCT/EP98/05714), 3D-MPL formulated with other carriers (EP 0 689 454 B1), QS21 formulated in cholesterol-containing liposomes (WO 96/33739), or immunostimulatory oligonucleotides (WO 96/02555). Adjuvant SBAS2 (now AS02) contains QS21 and MPL in an oil-in-water emulsion is also useful. Alternative adjuvants include those described in WO 99/52549 and non-particulate suspensions of polyoxyethylene ether (UK Patent Application No. 9807805.8).

The use of an adjuvant that contains one or more agonists for toll-like receptor-4 (TLR-4) such as an MPL® adjuvant or a structurally related compound such as an RC-529® adjuvant or a Lipid A mimetic, alone or along with an agonist for TLR-9 such as a non-methylated oligo deoxynucleotide-containing the CpG motif is also optional.

Another type of adjuvant mixture comprises a stable water-in-oil emulsion further containing aminoalkyl glucosamine phosphates such as described in U.S. Pat. No. 6,113,918. Of the aminoalkyl glucosamine phosphates the molecule known as RC-529 {(2-[(R)-3-tetradecanoyloxytetradecanoylamino]ethyl 2-deoxy-4-O-phosphono-3-O-[(R)-3-tetradecanoyloxy-tetradecanoyl]-2-[(R)-3-tetradecanoyloxytetra-decanoylamino]-p-D-glucopyranoside triethylammonium salt.)} is the most preferred. A preferred water-in-oil emulsion is described in WO 99/56776.

Adjuvants are utilized in an adjuvant amount, which can vary with the adjuvant, host animal and immunogen. Typical amounts can vary from about 1 µg to about 1 mg per immunization. Those skilled in the art know that appropriate concentrations or amounts can be readily determined.

According to several embodiments, the vaccine compositions according to the present invention may contain one or more adjuvants, characterized in that it is present as a solution or emulsion which is substantially free from inorganic salt ions, wherein said solution or emulsion contains one or more water soluble or water-emulsifiable substances which is capable of making the vaccine isotonic or hypotonic. The water soluble or water-emulsifiable substances may be, for example, selected from the group consisting of: maltose; fructose; galactose; saccharose; sugar alcohol; lipid; and combinations thereof.

The compositions of the present invention comprise according to several specific embodiments a proteosome adjuvant. The proteosome adjuvant comprises a purified preparation of outer membrane proteins of meningococci and similar preparations from other bacteria. These proteins are highly hydrophobic, reflecting their role as transmembrane proteins and porins. Due to their hydrophobic protein-protein interactions, when appropriately isolated, the proteins form multi-molecular structures consisting of about 60-100 nm diameter whole or fragmented membrane vesicles. This liposome-like physical state allows the proteosome adjuvant to act as a protein carrier and also to act as an adjuvant.

Vaccine compositions according to the present invention may include, for example, influenza polypeptides or peptide epitopes, conjugated with or coupled to at least one EMMPRIN-derived peptide or peptide analog according to the invention.

A typical dose for a peptide-based vaccine is in the range of 10 µg-10 mg, and administration is typically 3 monthly priming doses followed by boosters at an interval of 1-4 months. Other doses and vaccination regiments are possible. The exact dosing and regiment will be determined for each specific antigen and formulation using methods well known in the art.

According to other embodiments, a pharmaceutical composition according to the invention comprises at least one antibody or antibody fragment which recognizes a peptide antigenic determinant disclosed in the present invention. Pharmaceutical compositions comprising such antibody or antibody fragment are used according to some embodiments for passive immunization or for treatment of an existing disease or disorder.

In such pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Typically, the molecules of the present invention comprising the antigen-binding portion of an antibody or comprising a peptide, peptide analog, peptide multimer or peptide conjugate will be suspended in a sterile saline solution for therapeutic uses. The pharmaceutical compositions alternatively may be formulated to control release of active ingredient (molecule comprising the antigen-binding portion of an antibody) or to prolong its presence in a patient's body. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.), intraarticular, topical or parenteral administration will be preferred.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule (polypeptide, polynucleotide, organic molecule etc.) age, body weight, sex, or conditions of the patient, it will be determined by the physician in the end. In the case of parenteral administration, the daily dosage can generally be between about 1 mg to about 100 mg, preferably about 1 mg to about 10 mg, more preferably about 0.1 mg to about 1 mg, per kg body weight. The dosage can be administered, for example, in weekly, biweekly, monthly or bimonthly regimens. Other preferred methods of administration include intra-arterial administration of about 0.01 mg to about 100 mg per kg body weight. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

Suitable dosing regimens of combination chemotherapies are known in the art and described in, for example, Saltz et al. Proc ASCO 1999, 18, 233a and Douillard et al., Lancet 2000, 355, 1041-7.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Means for preparing and characterizing isolated peptides, peptide analogs, peptide multimers, fusion proteins and binding antibodies are well known in the art. A description follows as to exemplify techniques for the production and use of EMMPRIN peptides and molecules comprising them and EMMPRIN-binding antibodies in accordance with the present invention.

Materials and Methods

Cells: The tumorigenic renal carcinoma RENCA, and colon carcinoma CT26 as well as the macrophage-like RAW 264.7 (ATCC TIB-71) cell lines, are all derived from BALB/c mice. The tumorigenic prostate cancer TRAMP-C2 cell line is derived from C57BL/6 mice, All cell lines were cultured in Dulbeco's Modified Eagle's medium (DMEM) with 10% fetal calf serum (FCS), 1% L-glutamine, and antibiotics, and split twice a week at a ratio of 1:4. All cell lines were regularly tested for morphological changes and presence of mycoplasma.

For the experiments, $10^6$ tumor cells/0.5 ml were seeded in a 24-well plate in serum-free medium, in order to avoid possible masking of signals initiated by the exogenous stimuli. In co-cultures, $0.5 \times 10^6$ tumor cells and $0.5 \times 10^6$ RAW 264.7 macrophages were seeded in 0.5 ml serum-free medium. In some experiments, instead of RAW 264.7 cells, primary peritoneal Thioglycollate (TG)-elicited macrophages were used that were harvested from the peritoneum of BALB/c mice by peritoneal lavage 4 days after the i.p. injection of thioglycollate (3 ml of 24 mg/ml). The macrophages were first adhered to plastic for 2 h in a medium with 20% FCS, and after extensive washing to get rid of non-adhered cells, were scraped off the plate, counted and brought to a concentration of $1 \times 10^6$ cells/ml in serum-free medium. All cells were incubated for 48 hours without any additional stimulation, and cell viability was determined using the XTT assay (Biological Industries, Beit-Ha'emek, Israel).

Flow cytometry: To determine the expression of surface EMMPRIN, cells were harvested at the end of the experiment, centrifuged and resuspended in 100 μl medium containing 1% FCS with 2 μl of Fluorescein isothiocyanate (FITC)-conjugated anti-EMMPRIN. After 30 minutes of incubation in the dark at 4° C., the cells were centrifuged and resuspended with 500 μl containing 0.5% formaldehyde. The percentage of positive cells that expressed surface EMMPRIN and the mean fluorescent intensity (MF) were measured using the BD LSR-II flow cytometer.

Immunoblot Analyses: Mouse recombinant EMMPRIN (200 ng/lane) was loaded onto a 10% sodium dodecyl sulfate polyacrylamide gel electrophoresis (SDS-PAGE), electrophoretically separated, and transferred onto a nitrocellulose membrane. The membrane was incubated overnight at 4° C. in blocking buffer and then was cut into strips. Each strip was probed for 1 hour at room temperature with diluted (1:1,000 in phosphate buffered saline—PBS) immune or pre-immune serum. Strips were washed three times in 1×Tris-Buffered Saline with Tween 20 (TBST), and then incubated with horse-reddish peroxidase (HRP)-conjugated goat anti-rat IgG (diluted 1:1,000) for additional 1 hour at room temperature, followed by additional four washes in 1×TBST. The enhanced chemiluminescence (ECL) system, which contains the substrate of the HRP enzyme, was used for protein detection. One strip was probed with the commercial rat anti-mouse EMMPRIN and donkey anti-mouse IgG, and served as positive control (P.C).

ELISA: MMP-9 and VEGF were quantified using the DuoSet commercial ELISA kits according to the manufacturer's instructions (R&D Systems, Minneapolis, Minn.), using a standard curve. Samples from culture supernatants were diluted 1:10 for MMP-9 and 1:100 for VEGF.

Indirect ELISA: This assay was developed to determine the specificity of the polyclonal antibodies for the EMMPRIN protein. Mouse recombinant EMMPRIN (mrEMMPRIN, 200 ng/ml in PBS, R&D Systems) or the Fc portion of the human IgG were applied on wells of a 96-well plate and incubated at 4° C. overnight to coat the wells. Excess antigens were removed by washing three times with wash buffer (0.05% Tween-20 in PBS), followed by blocking of the remaining free protein-binding sites with blocking buffer (1% BSA in PBS) for 2 hours at room temperature. After additional washes, strips of mouse recombinant EMMPRIN or Fc were coated with each of the primary antibodies (immune or pre-immune sera) diluted 1:500 and 1:5000 in PBS, and incubated for 2 hours at room temperature. After additional washes, the HRP-conjugated donkey anti-rabbit diluted 1:10,000 (80 ng/ml) was added and incubated for additional 2 hours at room temperature, followed by four washes and incubation with TMB solution for 5 minutes. The positive control wells were incubated with the commercial rat anti-mouse EMMPRIN (0.5 μg/ml), then), then with the HRP-conjugated secondary antibody goat anti-rat diluted 1:1000 (0.4 μg/ml). The reaction was stopped with stop solution (0.25M HCL), and the absorbance of each well was measured at 450 nm and at a reference of 540 nm. OD values of Fc binding were subtracted from the OD values of the mouse recombinant EMMRPIN binding values.

Peptide Conjugation, Immunization and Affinity Purification of Polyclonal Antibodies: The designed peptides were synthesized (Adar Biotech, LTD, Rehovot, Israel) and conjugated to the Keyhole Limpet Hemocyanin (KLH) carrier protein, then used to immunize two rabbits with each peptide, which were bled before (pre-immune sera) and after each immunization. To detect an antibody response, an ELISA was designed and used, where the titer of the antibodies was determined according to their level of binding to each peptide. The sera were collected after each boost injection, and the polyclonal anti-peptide antibodies were purified on a peptide affinity chromatography.

Polyclonal antibodies are preferably raised in animals by multiple subcutaneous (sc) or intraperitoneal (ip) injections of the relevant antigen and an adjuvant. It may be useful to conjugate the relevant peptide antigen to a protein with T-cell epitopes in the species to be immunized, e.g., keyhole limpet hemocyanin (KLH), serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the peptide antigen, immunogenic conjugates, or derivatives by combining, e.g., 100 μg or 5 μg of the protein or conjugate (for rabbits or mice, respectively) with 3 volumes of CFA and injecting the solution intradermally at multiple sites. One month later the animals are boosted with ⅕ to ⅒ the original amount of peptide or conjugate in IFA by subcutaneous injection at multiple sites. Seven to 14 days later the animals are bled and the serum is assayed for antibody titer. Animals are boosted in the same way until the titer plateaus. The animal also may be boosted with a conjugate of the same antigen but conjugated to a different carrier protein and/or through a different cross-linking reagent. Conjugates also can be made in recombinant cell culture as protein fusions. Also, adsorbing and depoting agents such as alum are suitably used to enhance the immune response.

Branched peptide synthesis: Peptide sequences that were used to generate the polyclonal antibodies were synthesized as a branched peptide using the Multiple Antigenic Peptides (MAP) technique (Tam J P. Proc Natl Acad Sci USA. 1988; 85:5409-5413.). In this technique the peptide sequence is conjugated to a core matrix of lysine (Lys) residues, thus forming a branched peptide (for example, octa-branced peptide using 8 Lys residues). The highly charged peptide backbone increases the immunogenicity of the peptide, so that conjugation to a carrier protein is no longer needed to elicit high titers of polyclonal antibodies.

In Vivo Tumor Models and Vaccination:

Mice: BALB/c mice (female, 8 weeks old) were kept with a 12-hour light/dark cycle and access to food and water ad libitum. Mice were cared for in accordance with the procedures approved by Technion Committee for Care and Use of Laboratory Animals and outlined in the National Institutes of Health Guidelines for the Care and Use of Laboratory Animals. Tumors were generated by s.c. injecting $2 \times 10^6$ tumorigenic cells suspended in 200 μl of Matrigel™ into the flank of BALB/c mice (for RENCA and CT26 cells). Tumors were then measured every 3-4 days, and their volumes were calculated (length×width×0.5 $cm^3$). Mice were euthanized at the end of the experiment or when tumors grew larger than 1.0-1.5 $cm^3$. For the metastatic models, tumor lung metastases were generated by injecting $1 \times 10^6$ tumorigenic cells in 200 μl PBS into the tail vein. After 14-16 days (for the CT26 model) or after 21-23 days (for the RENCA model), mice were euthanized and the lungs were removed. The number of metastases was counted under a dissecting microscope.

Passive immunization: Female BALB/c mice (8 weeks old, 20-25 gr) were injected with RENCA or CT26 cells, and when tumors became palpable (day 13 for RENCA tumors, and at day 15 for CT26 tumors), mice were randomly assigned to five groups. The control group was i.p. injected three times with 2 ml saline, and the other groups were i.p. injected with different concentrations of the 161 antibody (100 μg/2 ml, 50 μg/2 ml, and 25 μg/2 ml) or with another, non-inhibitory anti-EMMPRIN antibody (the 162 antibody, 100 μg/2 ml), in three boosts, every 6 days. Tumor dimensions were measured and their volumes were calculated.

Active immunization: Female BALB/c mice (8 weeks old, 20-25 gr) were injected with RENCA or CT26 cells as described before. At day 7, 14 and 21 after the first injection, mice were mildly anesthetized (3% isofluoran) and increasing amounts of the peptide (10 μg/30 μl, 25 μg/30 μl and 50 μg/30 μl) dissolved in CFA (first boost) or IFA (second and third boost injections) were injected into the footpad of each mouse. The fourth group received injections of CFA or IFA only. Tumor dimensions were measured, and their volumes were calculated.

Statistical Analyses: All values are presented as means±SE (standard error). The data were analyzed using one-way analysis of variance (ANOVA). The Student Newman-Keuls multiple comparison test was used to evaluate the significance between experimental groups, and p values >0.05 were not considered statistically significant. For the in vivo tumor model experiments, two-way ANOVA was used to determine the effects of the time and antibody/peptide concentrations on tumor growth rate.

Example 1

Peptide Design and Specificity of the Antibodies

In contrast to previous experiments, which used the entire extracellular portion of the EMMPRIN protein to raise polyclonal and monoclonal antibodies, the aim of this study was to map the precise peptide epitope(s) that is(are) responsible for the induction of VEGF and/or MMP-9. When designing and choosing the peptides to be used in raising polyclonal antibodies, all the domains of the known extracellular portion of EMMPRIN were examined. Hydrophilic peptides that are located on the exterior part of the protein and are therefore more antigenic, where chosen based on the algorithms used. Specific peptides that were predicted to be most antigenic according to both the EMBOSS and Open Biosystems algorithms were selected, and were also proven to be specific to EMMPRIN by using Blast homology searches (indicating the quality of the match between two sequences). In addition, peptides that were as homologous to the human sequence as possible were used; however, due to the low homology between mouse and human sequences (about 65%), every peptide synthesized had at least 3 amino acids that were different. These peptides were also not homologous to any mouse protein including the other two EMMPRIN-family members Neuoplastin or Embigin. Based on all these considerations, it was almost impossible to find peptide sequences within the EC-II domain, and only two such sequences could be located within the EC-I domain, whereas the rest of the peptides were located in the distal domain that is unique to the long EMMPRIN isoform. The eight different peptides spread along the extracellular domains of EMMPRIN, EC-0, EC-I and EC-II, also termed D-0, D-I and D-II as disclosed in Belton R J, at el., Ibid, which were selected for syntheses are detailed in Table 1.

TABLE 1

Peptides used to raise polyclonal antibodies.

| # Peptide | Length | Extra Extracellular Region | Blast Score |
|---|---|---|---|
| 156 | 14aa | EC-0 | 43.5 |
| 157 | 15aa | EC-0 | 50.3 |
| 158 | 13aa | EC-0 | 39.7 |
| 159 | 20aa | EC-0 | 59.2 |
| 160 | 21aa | EC-I | 76.8 |
| 161 | 12aa | EC-I | 50.5 |
| 162 | 11aa | EC-II | 40.1 |
| 163 | 16aa | EC-I | 51.1 |

Figure 2:
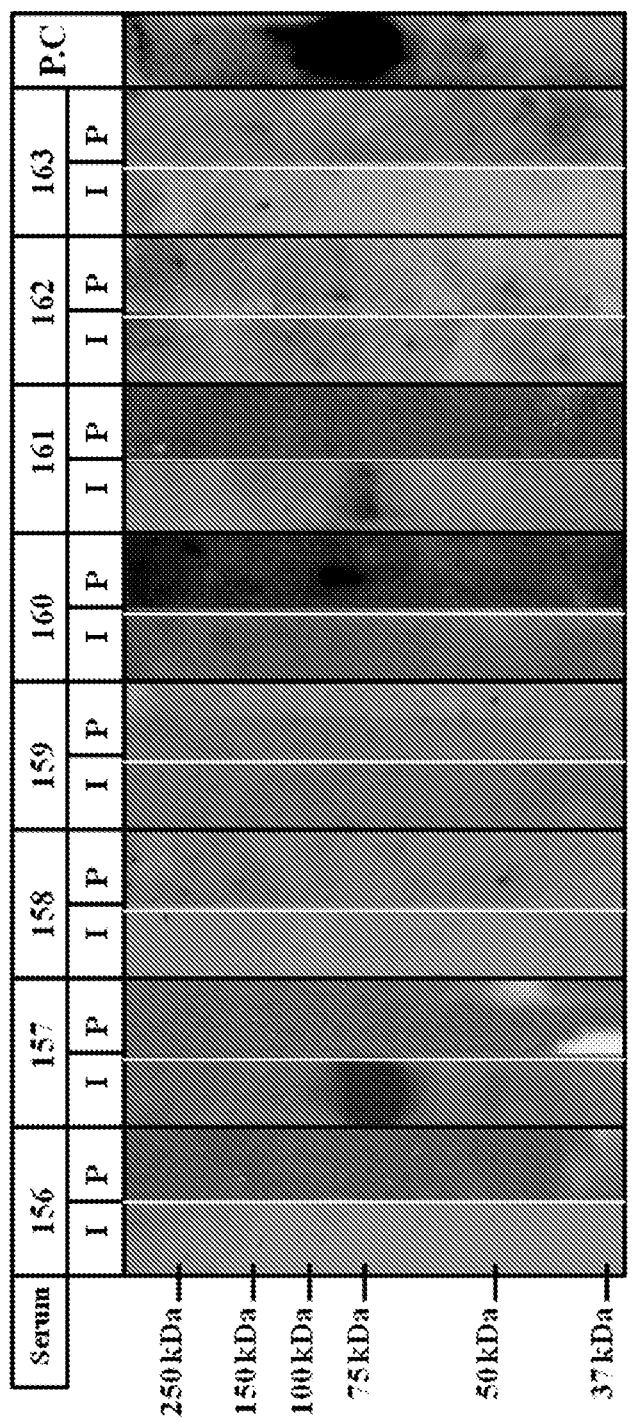
FIG. 2 Recognition of mouse recombinant EMMPRIN by polyclonal antibodies. Mouse recombinant EMMPRIN (200 ng/lane) was loaded onto a 10% SDS-PAGE, electrophoretically separated, and transferred onto a nitrocellulose membrane. The membrane was cut into strips and each strip was probed with diluted (1:1,000) immune (I) or pre-immune (P) serum. One strip was probed with the commercial rat anti-mouse EMMPRIN and served as positive control (P.C).

Peptides were synthesized, using conventional solid-phase methods, conjugated to the carrier KLH, and each conjugate was injected into two rabbits. Pre-immune and immune sera were collected, and the titer of each antibody was determined qualitatively by ELISA (FIG. 1). The high titers observed for all antibodies and the lack of response to BSA indicate that the generated antibodies were specific for their respective immunizing peptides and that the immune sera contained antibodies in relatively high concentrations. However, as the antibodies could recognize either linear epitopes based on their primary sequence or conformational epitopes based on their spatial structure, they did not necessarily recognize the full-length EMMPRIN protein. The ability of each of the eight immune sera to bind to EMMPRIN was evaluated by immunoblot analysis and indirect ELISA. The immunoblots used denatured mrEMMPRIN as the antigen, and each of the 8 antibodies (or their pre-immune sera) was tested by adding it as a primary antibody, followed by incubation with a secondary HRP-conjugated anti-rabbit IgG. Only two antibodies, designated #157 and #161, specifically recognized mrEMMPRIN using the immune, but not the pre-immune serum (FIG. 2), indicating that these antibodies can recognize the primary sequence of the denatured EMMPRIN protein.

The specificity and ability of the antibodies to recognize mrEMMPRIN in its native structure were also tested by indirect ELISA, using mrEMMPRIN (200 ng/ml) or human IgG Fc protein (hFC, 200 ng/ml) to coat 96-well plates. Each well was probed with immune or pre-immune serum of each of the polyclonal antibodies in duplicate (n=4), and OD values were subtracted from the background of the response to Fc protein. P values were calculated by the Mann-Whitney T test. **, $p<0.01$, relative to pre-immune sera. The results are summarized in Table 2.

TABLE 2

Specificity of the antibodies to EMMPRIN, determined by indirect ELISA

| # Antibody | Immune sera | Pre-Immune sera | P value |
|---|---|---|---|
| 156 | 0.0052 ± 0.0082 | 0.040 ± 0.034 | 0.3053 (ns) |
| 157 | 0.033 ± 0.02 | 0.048 ± 0.016 | 0.8857 (ns) |
| 158 | 0.0013 ± 0.004 | 0.028 ± 0.02 | 0.2683 (ns) |
| 159 | 0.004 ± 0.01 | 0.007 ± 0.05 | 0.981 (ns) |
| 160 | 0.004 ± 0.005 | 0.008 ± 0.003 | 0.8000 (ns) |
| 161 | 0.052 ± 0.026 | 0.008 ± 0.0087 | 0.0260 ** |
| 162 | 0.0030 ± 0.0085 | 0.0040 ± 0.0030 | 0.5333 (ns) |
| 163 | 0.0015 ± 0.019 | 0.050 ± 0.029 | 0.2454 (ns) |

Since mrEMMPRIN is a chimeric protein composed of the extracellular portion of EMMPRIN fused to the Fc portion of human IgG, the human Fc protein was used as a negative control for subtraction for subtraction of its OD value. Antibody #161, raised against a peptide having the sequence GHRWMRGGKVLC (SEQ ID NO.: 1) from the EC-I domain of mouse EMMPRIN, was the only one to show specificity of the antibody serum to mrEMMPRIN (by 4.9 fold relative to pre-immune sera, $p<0.01$). It recognizes mrEMMPRIN in both the denatured and native conformations, and it is likely to actually recognize the protein in both in vitro and in vivo systems.

Example 2

An in vitro Screening Platform Using Tumor Cell-macrophage Co-cultures for Screening Antibodies for the Ability to Inhibit Secretion of VEGF and MMP-9

Among the many activities of EMMPRIN, the ability to induce MMP-9 and VEGF, which are crucial mediators of angiogenesis and tumor growth, was chosen as a parameter of activity. To establish an in vitro platform for screening for inhibitory effects of antibodies, a search for conditions that trigger high secretion of MMP-9 and VEGF was performed.

First, in vitro conditions were established where the expression of EMMPRIN, MMP-9 and VEGF was maximal, or at least markedly stimulated. Preliminary experiments indicated that cells had to be incubated for at least 48 h in order to observe changes in the levels of accumulation of secreted MMP-9 and VEGF, and therefore this time point was used in the following experiments. Single cultures of tumor cells or macrophages or both cell types were incubated in co-cultures for 48 h, supernatants were collected for determination of the concentrations of secreted VEGF and MMP-9, and the cells were harvested for determination of surface EMMPRIN expression. Cell viability was routinely monitored in all cultures, but remained unchanged for the duration of the experiment.

Expression of membrane-associated EMMPRIN, estimated by flow cytometry (FIGS. 3 and 4), was increased in both co-cultures of CT26 or RENCA cells with RAW 264.7 macrophages relative to each of the single cultures (by about 2 fold, respectively, $p<0.05$). However, co-cultures did not significantly affect the amount of EMMPRIN expressed on the cell surface (as indicated by no change in the mean fluorescence), and only a minor increase or decrease in the overall expression of surface EMMPRIN on both cell types was observed. When TG-elicited macrophages were used, co-cultures showed a 2-fold reduction in surface EMMPRIN expression relative to each single culture ($p<0.05$). TRAMP-C2 cells expressed relatively high amounts of surface EMMPRIN, and incubation in co-culture with RAW 264.7 or TG-elicited macrophages reduced it by 1.4- and 1.8-fold, respectively ($p<0.01$).

Figure 3A:
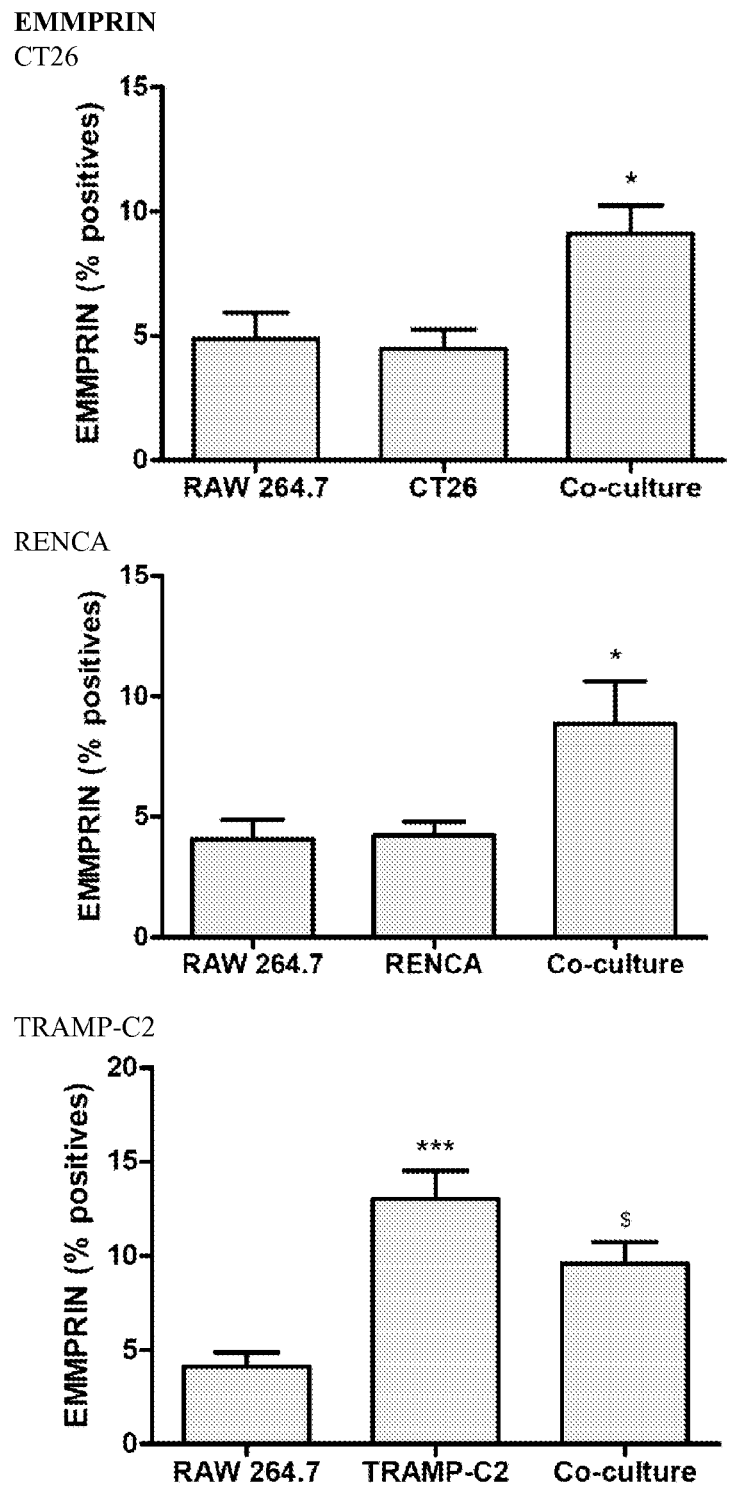
FIGS. 3A-3C Effect of co-culture of tumor cells and RAW 246.7 macrophages on the secretion of EMMPRIN (FIG. 3A), MMP-9 (FIG. 3B), and VEGF (FIG. 3C). Each of the tumor cell lines ($0.5 \times 10^6$ cells of RENCA, CT26, or TRAMP-C2) were incubated alone or in co-culture with $0.5 \times 10^6$ RAW 264.7 cells (n=14) for 48 h. Supernatants were collected and the concentrations of secreted MMP-9 and VEGF were determined by ELISA. Surface EMMPRIN expression was determined by flow cytometry. *, $p<0.05$, ***, $p<0.001$ relative to each of the single cultures. $, $p<0.05$ relative to TRAMP-C2 single culture.
Figure 3B:
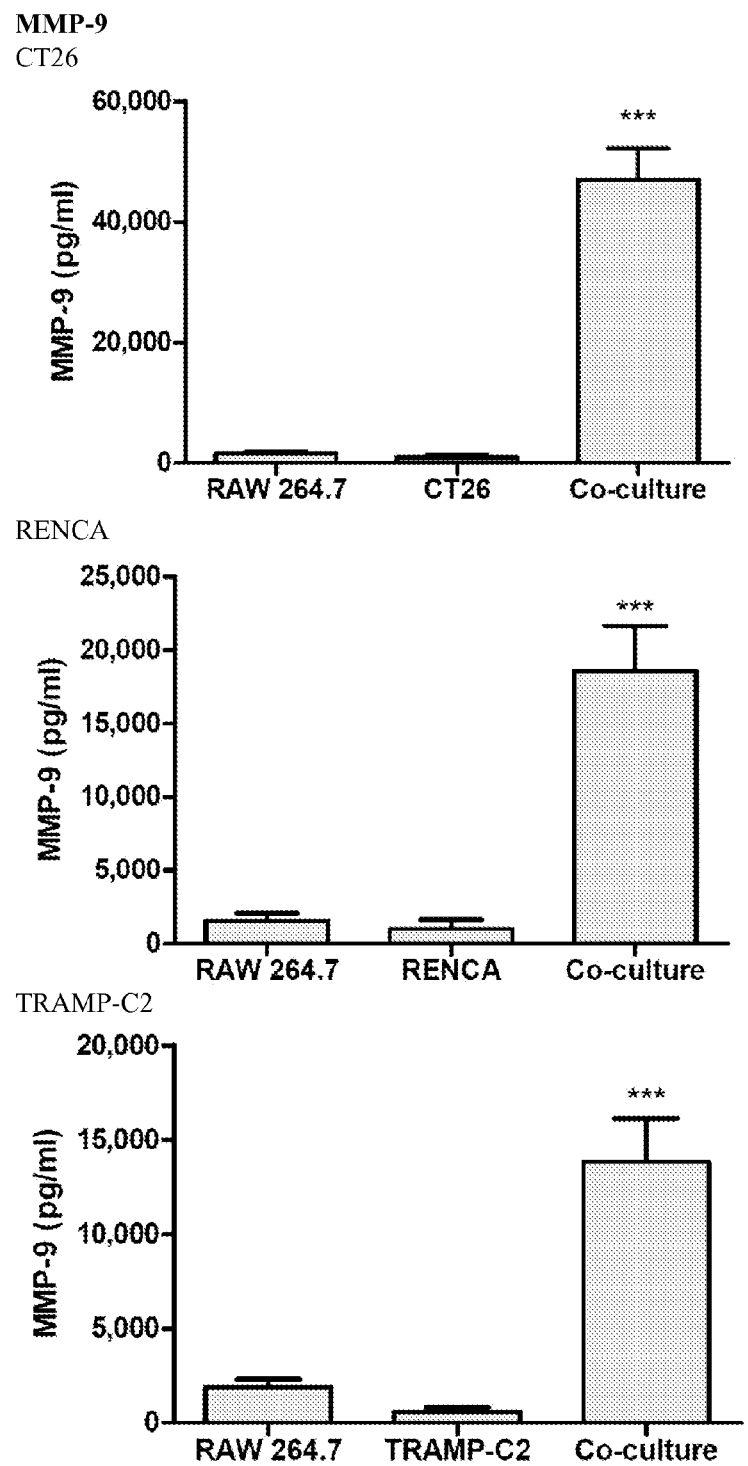
Figure 3C:
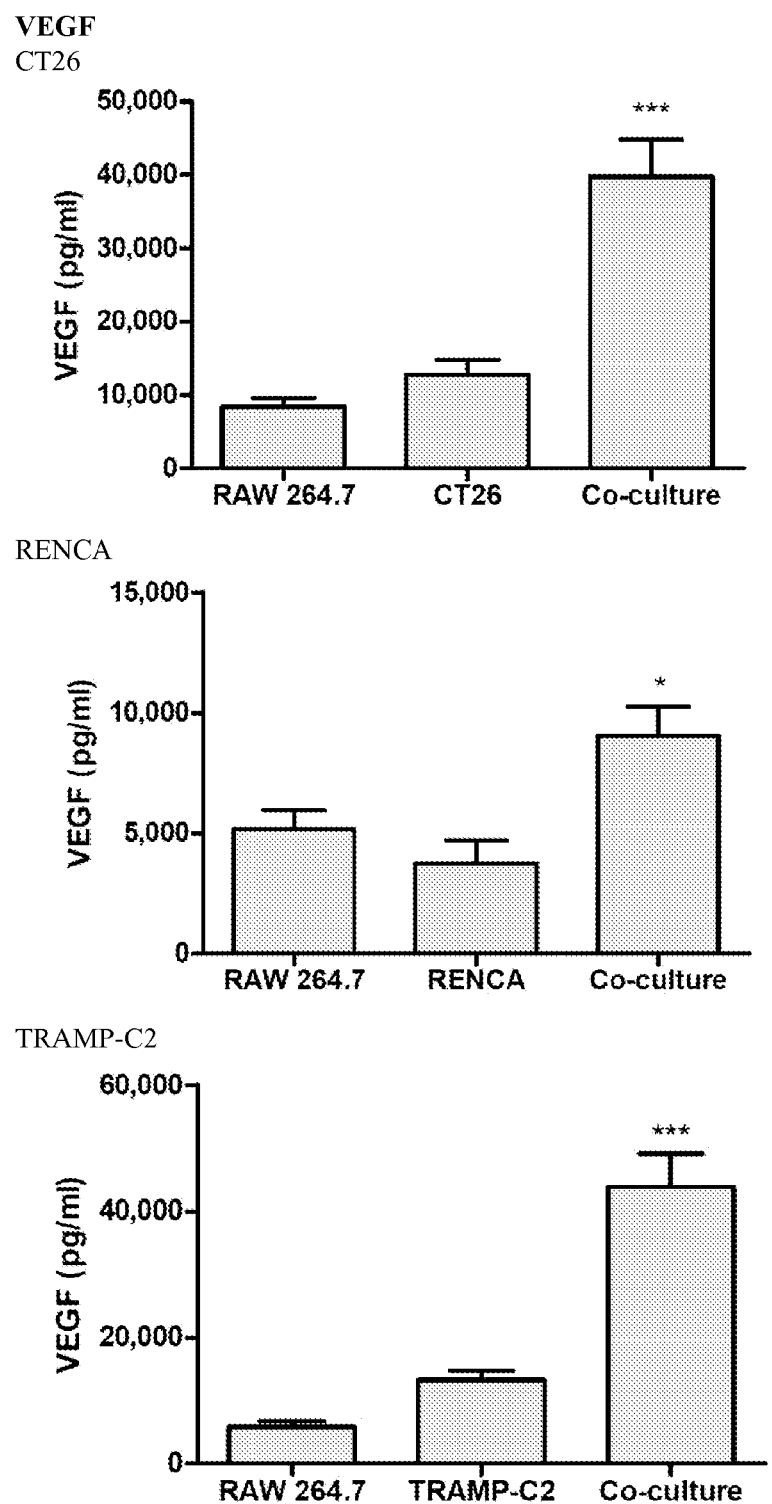
Figure 4A:
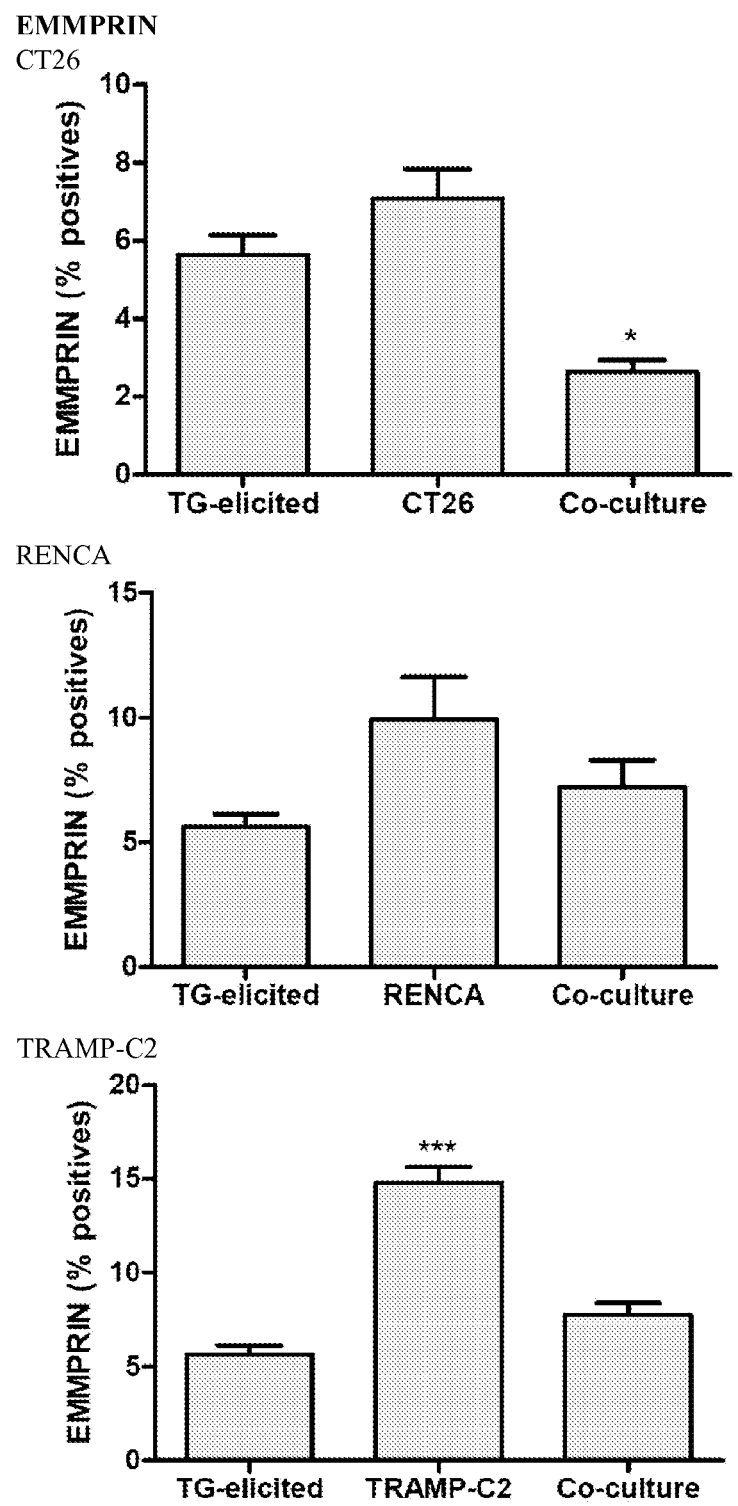
FIGS. 4A-4C Effect of co-culture of tumor cells and TG-elicited macrophages on the secretion of EMMPRIN (FIG. 4A), MMP-9 (FIG. 4B), and VEGF (FIG. 4C). Each of the tumor cell lines ($0.5 \times 10^6$ cells of RENCA, CT26, or TRAMP-C2) was incubated alone or in co-culture with $0.5 \times 10^6$ TG-elicited macrophages (n=4) for 48 h. Supernatants were collected and the concentrations of secreted MMP-9 and VEGF were determined by ELISA. Surface EMMPRIN expression was determined by flow cytometry. *, $p<0.05$, ***, $p<0.001$ relative to each of the single cultures.
Figure 4B:
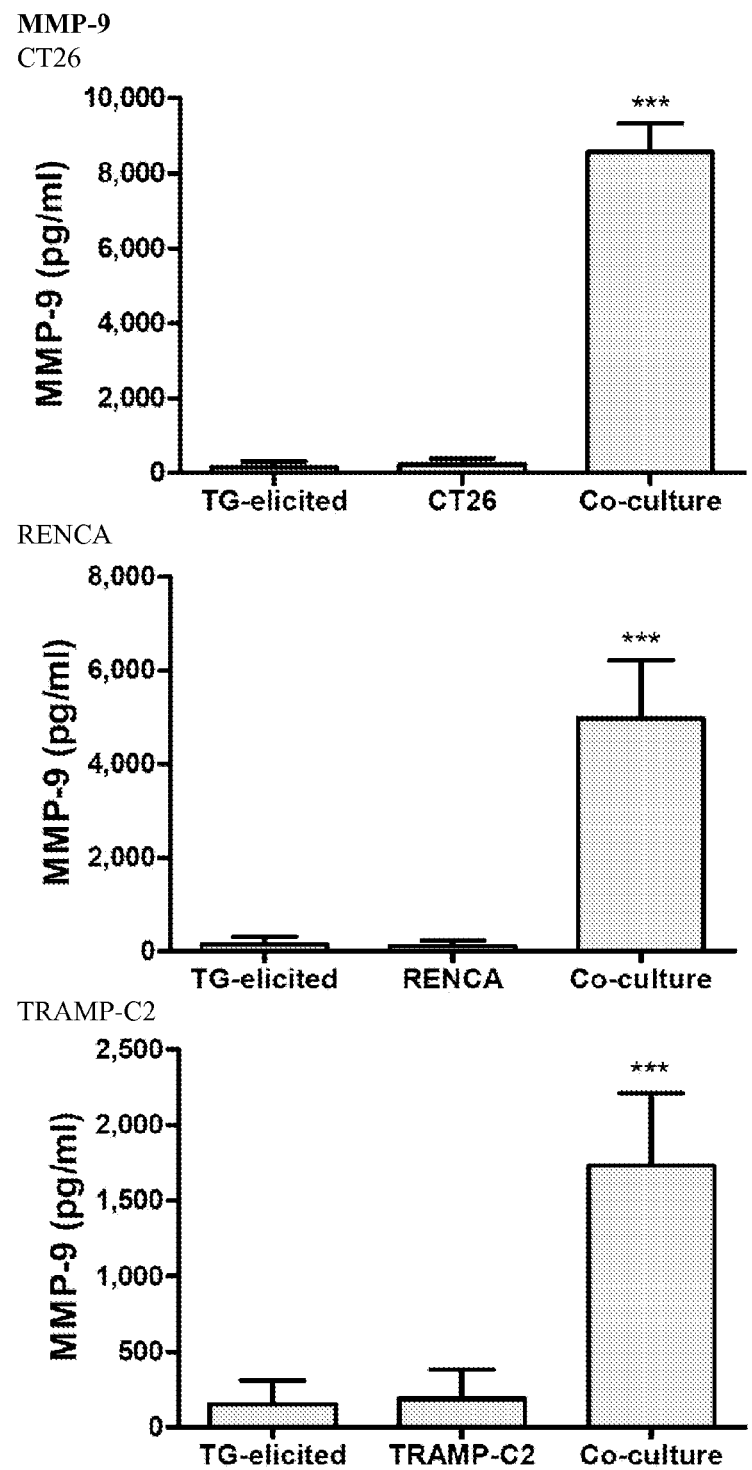
Figure 4C:
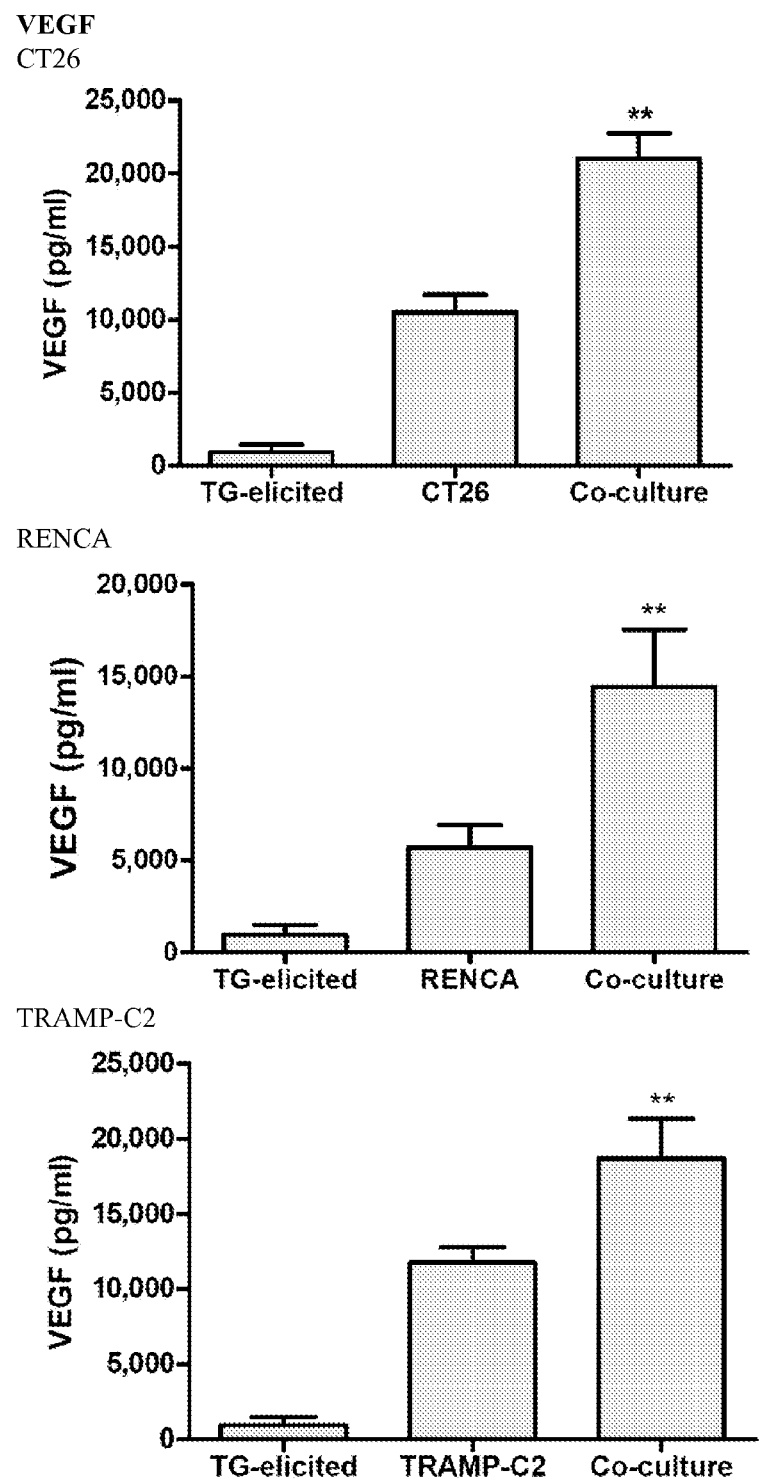

The effects of the co-culture on the secretion of MMP-9 and VEGF were also tested. FIGS. 3 and 4 show that all tumor cell lines incubated in single cultures secreted only minimal levels of MMP-9 (1,598±456 pg/ml for CT26, 1,232±684 pg/ml for RENCA, and 354±117 pg/ml for TRAMP C2). Similarly, TG-elicited macrophages or RAW 264.7 cells incubated in single cultures in normoxia also secreted only minimal amounts of MMP-9 (153±153 pg/ml for TG-elicited and 3,000±456 pg/ml for RAW 264.7). Incubation of each of the tumor cell lines with either the RAW 264.7 or the TG-elicited macrophages in co-cultures in normoxia synergistically and significantly increased the secretion of MMP-9 by 30-fold for CT26 cells ($p<0.001$), by 12- and 32-fold, respectively for RENCA ($p<0.001$), and by about 8-fold for TRAMP-C2 cells ($p<0.001$) relative to each of the macrophage single cultures, and by more relative to the single tumor cell cultures.

Unlike MMP-9, VEGF was constitutively expressed in all cell lines but not in the TG-elicited macrophages. VEGF expression in each of the tumor cells was moderate in normoxia (9,166±963 pg/ml for CT26, 3,122±614 pg/ml for RENCA, 9,894±998 pg/ml for TRAMP-C2, and 5,887±897 pg/ml for the RAW 264.7 macrophages), but in the TG-elicited macrophages the concentration of VEGF was relatively low (616±598 pg/ml). However, co-culture of each of the tumor cells with either RAW 264.7 or TG-elicited macrophages significantly elevated the accumulated amounts of the VEGF in the medium by 2-5 fold relative to each of the tumor cell and to the RAW 264.7 single cultures ($p<0.01$), and by 15-22 fold relative to the TG-elicited macrophage single cultures ($p<0.01$).

Example 3

Figure 5A:
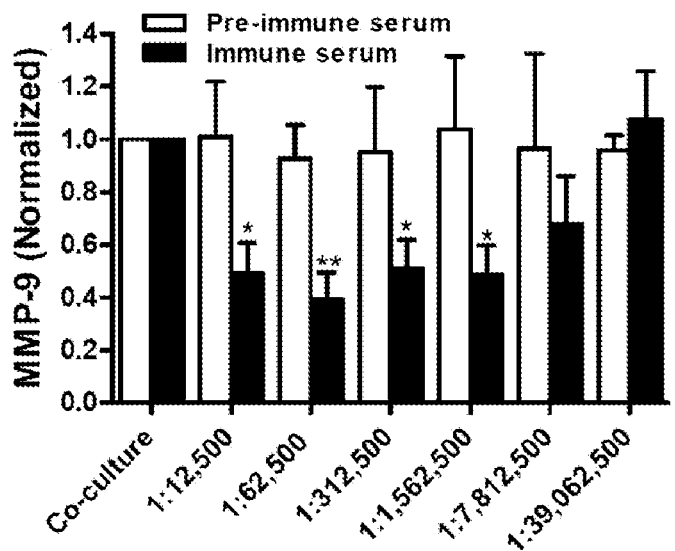
FIGS. 5A-5B Effect of antibody #161 immune and pre-immune sera on MMP-9 and VEGF secretion from co-cultures. RAW 264.7 and CT26 tumor cells ($0.5 \times 10^6$ each, n=6.
Figure 5A:
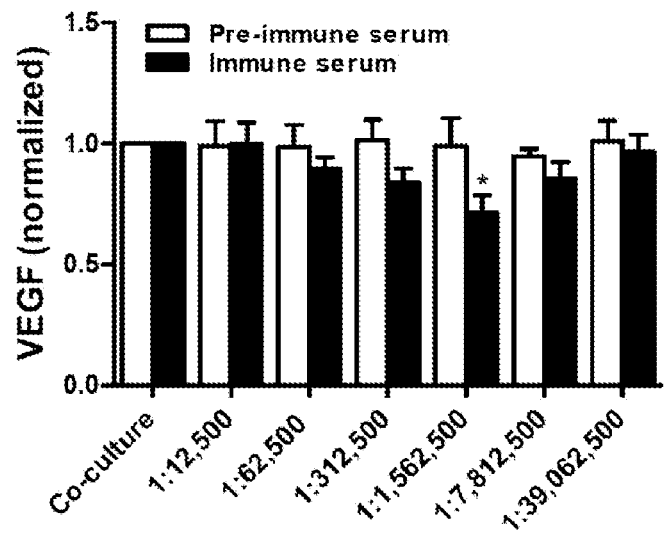
Figure 5B:
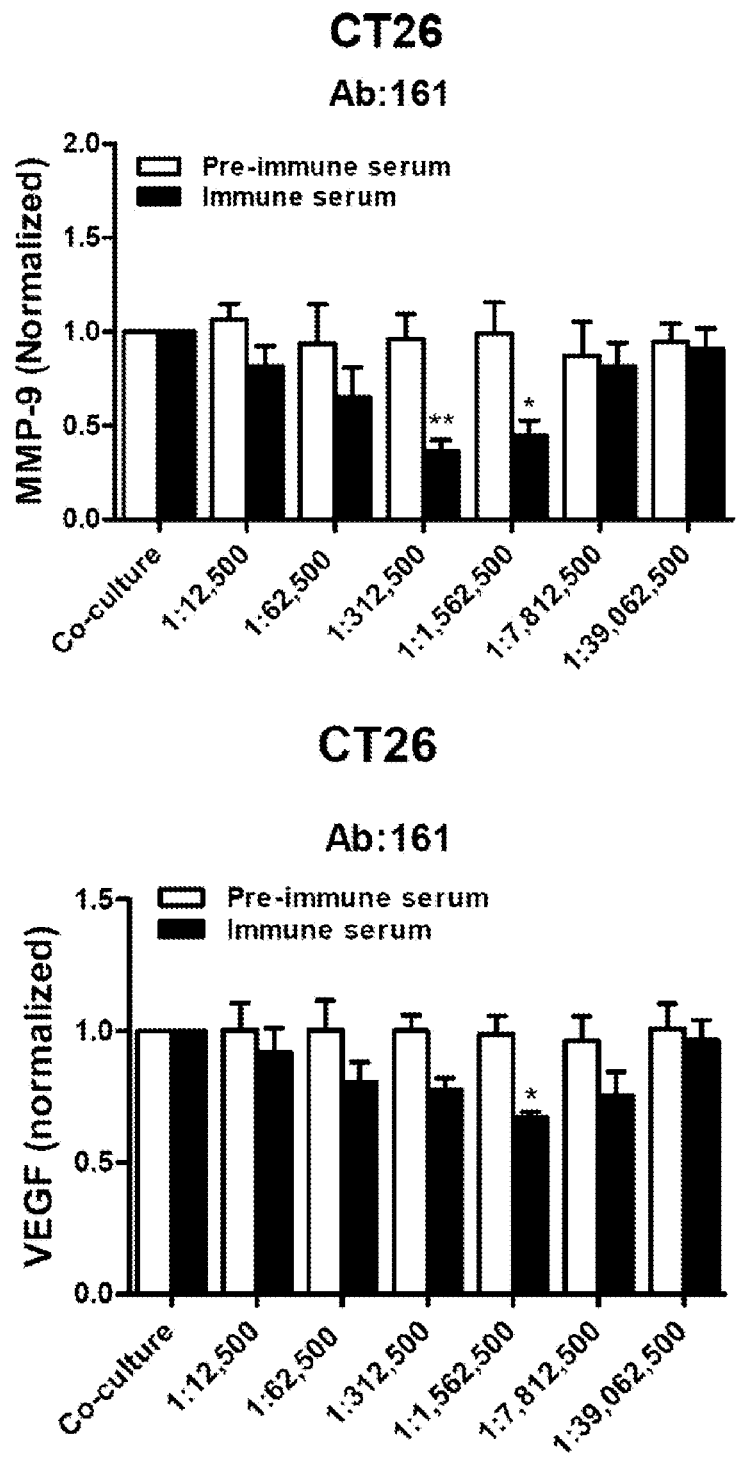

Screening of the Polyclonal Antibodies for Inhibitory Effects on MMP-9 and VEGF Using Mouse and Human In Vitro Co-culture Systems The co-culture setup previously described generated high amounts of secreted VEGF and MMP-9. Therefore, these conditions were used to screen for antibodies that can inhibit the EMMPRIN-mediated induction of VEGF and/or MMP-9. Immune and pre-immune sera of each of the eight antibodies were diluted (5-fold serial dilutions) and incubated together with co-cultures of CT26 or TRAMP-C2 tumor cells with RAW 264.7 macrophages for 48 h. Supernatants were collected, and concentrations of VEGF and MMP-9 were evaluated by ELISA. Seven of the eight antibodies mediated no significant change in the concentration of either MMP-9 or VEGF between the immune and pre-immune sera in the different dilutions, and also in comparison to the co-cultures alone (without the addition of the immune or pre-immune sera). Only polyclonal antibody #161 reduced the expression of VEGF and MMP-9 in some of the tested dilutions, in both the TRAMP-C2 and CT26 co-cultures (FIG. 5). In the macrophage-TRAMP-C2 and macrophage-CT26 co-cultures, the antibody reduced MMP-9 by up to 61% in dilution 1:62,500 ($p<0.01$), and by 64% in dilution 1:312,500 ($p<0.01$), respectively, relative to pre-immune serum. Similarly, VEGF concentrations in these co-cultures were reduced by 29% and 33%, respectively ($p<0.05$), in 1:1,565,500 dilution, relative to pre-immune serum.

Figure 6A:
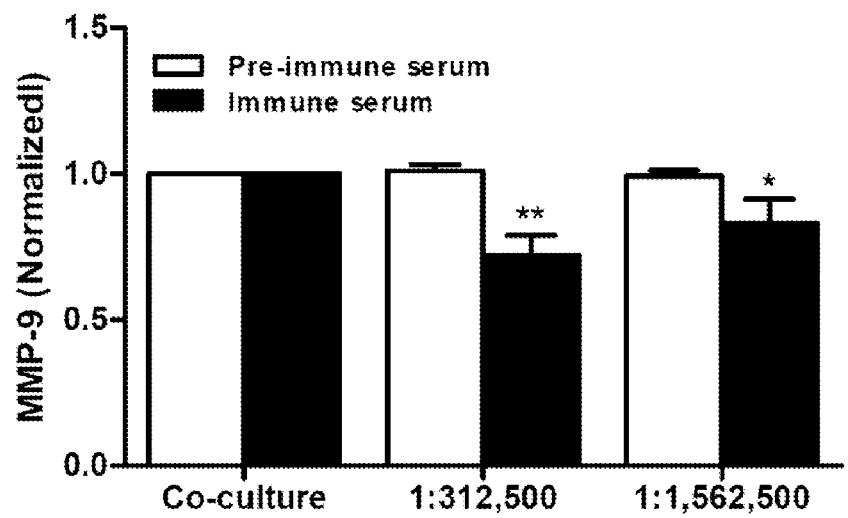
FIGS. 6A-6B Cross-reactivity of antibody #161 with human EMMPRIN. The human monocytic-like U937 cells ($0.5 \times 10^6$) were co-incubated with the $0.5 \times 10^6$ cells of the human renal cell carcinoma A498 tumor cell line (n=3) (FIG. 6A) or the breast carcinoma MCF-7 tumor cell line (n=3) (FIG. 6B) in a serum-free medium for 48 hours with selected dilutions of immune or pre-immune serum. VEGF and MMP-9 concentrations were determined in the supernatants by ELISA. *, $p<0.05$, , $p<0.01$, *, $p<0.001$ relative to co-culture without addition of sera.
Figure 6A:
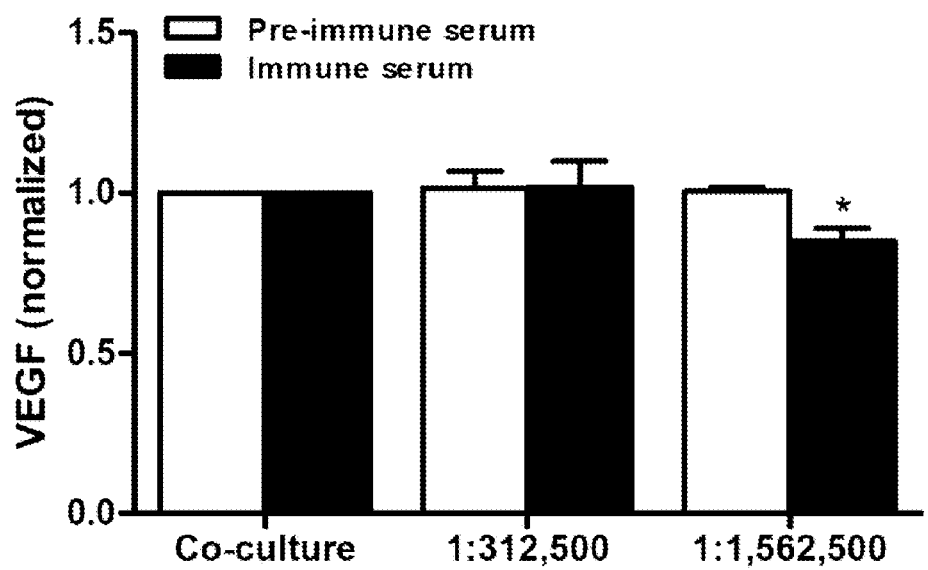
Figure 6B:
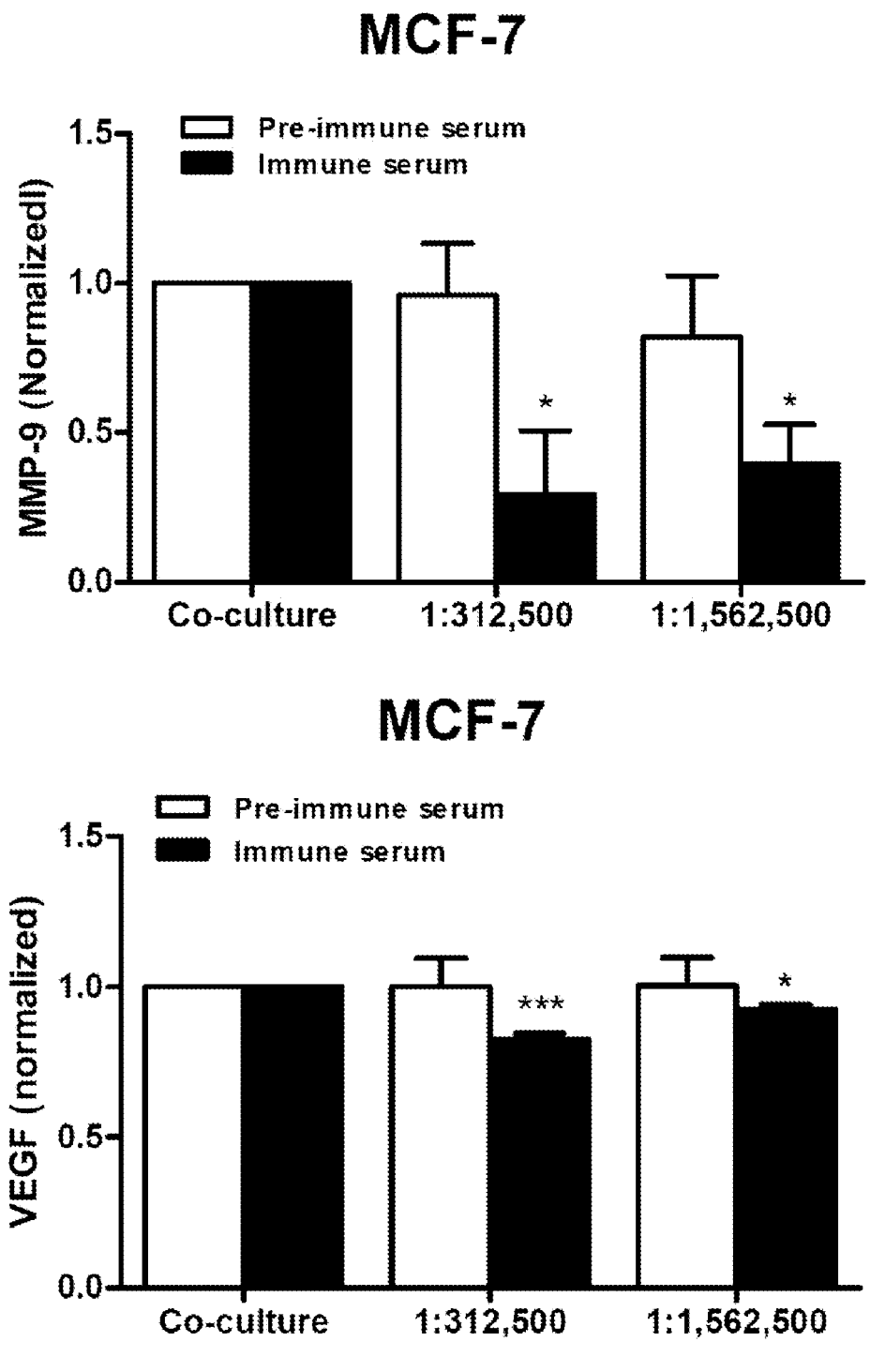

Antibody #161 was generated against a mouse peptide that has only 3 different amino acids compared to the human peptide, and thus could exhibit some cross-reactivity in binding and in effects in culture. To evaluate the ability of antibody #161 to cross-react with the human EMMPRIN, a similar human system was used with two tumor cell lines, the human renal cancer cell line (A498) and human breast cancer cell line (MCF-7) that were co-cultured with a human monocyte-like cell line (U937). The dilutions that previously worked in the mouse system (1:312,500 and 1:1,562,500), were used, and the co-cultures were incubated with these concentrations of antibody #161 (FIG. 6). Using these two dilutions relative to pre-immune serum, MMP-9 concentrations were reduced in both co-cultures after 48 hours of incubation with the immune serum by 28% ($p<0.01$) and by 21% ($p<0.05$) for the A498 co-cultures, and by 71% and by 61% ($p<0.05$) for the MCF-7 co-cultures. Similarly, VEGF concentrations after incubation with the immune serum were reduced in the higher dilution relative to pre-immune serum by 15% ($p<0.05$) in the A498 co-culture and by the two dilutions by 18% ($p<0.001$) and 8% ($p<0.05$), respectively, in the MCF-7 co-cultures.

Example 4

The Polyclonal Anti-EMMPRIN Antibody #161 Inhibits Tumor Growth in vivo

The ability of polyclonal antibody #161 to reduce tumor growth and progression was tested in two different cancer models. Many studies using passive immunization therapy in animal models routinely immunize mice before administration of the relevant tumor cells (Hu et al. Cancer Biol Ther. 2007; 6:1773-1779). Thus, antibodies existing in the circulation may combat tumors during very early stages, when the immune system is still not suppressed by the tumoral microenvironment (the elimination phase of the immunoediting process). In contrast, stimulation was tested in the human real-life scenario, by administrating the first antibody injection after the tumor was already palpable. In such later stages the tumor has already developed a microenvironment that suppresses an immune response and helps tumor cells to escape immune detection. Another study also used an anti-EMMPRIN mAb (with an unknown epitope) during later stages of tumor progression in SCID mice bearing human head and neck squamous cell carcinoma tumors, and in combination with radiotherapy in vivo and showed a significant delay in tumor progression (Dean et al. Clin Cancer Res. 2009; 15: 4058-4065.).

Figure 7B:
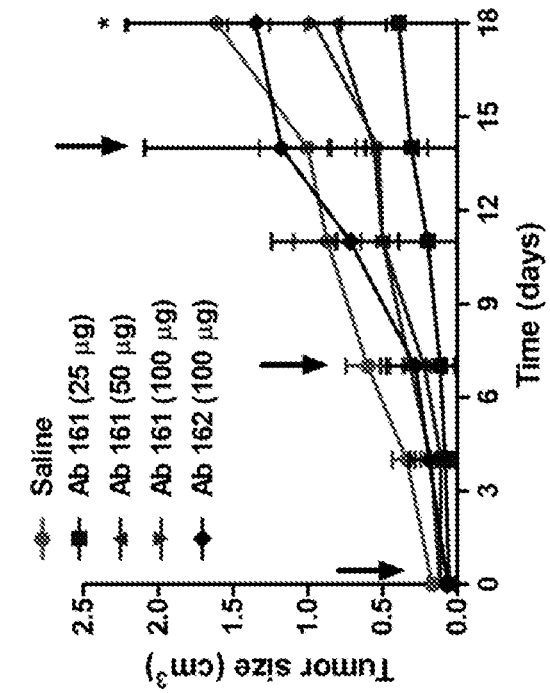
FIGS. 7A-7B Effect of passive immunization with anti-EMMPRIN (#161) on tumor growth rate in RENCA (FIG. 7A) and CT26 (FIG. 7B) tumor-bearing mice. $2 \times 10^6$ tumor cells were injected subcutaneously (s.c.) to BALB/c mice. Once the tumors became palpable (at day 13 or 15 for RENCA and CT26 tumors, respectively), mice were randomly assigned to the different groups, and were injected intraperitoneally (i.p.) with different concentrations of the #161 antibody (day 0), followed by additional two boost injections every 7 days (black arrows). *, $p<0.05$, the control saline and Ab 162 groups relative to the group receiving Ab 161 (25 µg) at the indicated time points.
Figure 7A:
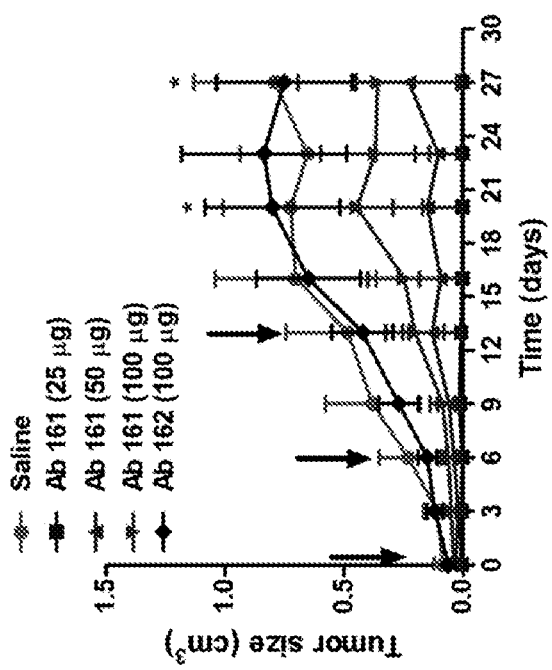

BALB/c mice were first injected with either the RENCA or CT26 cell lines, to generate small (about 2 mm×2 mm), but palpable subcutaneous tumors by day 13 (for RENCA) and day 15 (for CT26). At these time points the affinity purified antibody #161 was injected i.p. at different concentrations (25 µg/2 ml, 50 µg/2 ml and 100 µg/2 ml), with additional boosts every 7 days. Either saline without antibody or antibody #162 that did not inhibit MMP-9 or VEGF in the in vitro screening tests was injected as control. Tumor growth was monitored every 3-4 days, and volumes calculated. In both RENCA and CT26 injected mice, the antibody inhibited tumor growth more extensively at the lower dose of 25 µg. In RENCA tumors, growth was inhibited by 2.2-, 3.4- and 158-fold, respectively, and in the CT26 tumors by 1.7-, 2.0- and 4-fold, reaching statistical significance ($p<0.05$) in both tumor types for the low dose in comparison to the saline control group at the last day of the experiment (FIG. 7).

Example 5

Synthesis of the Peptide #161 as a Multimer (161-MAP)

The synthesis of an octa-branched MAP conjugate was accomplished manually by a stepwise solid-phase procedure on Fmoc-Beta-Ala-Wang resin in which 0.05 mmol of Beta-Ala is present in 0.5 g of resin. The synthesis of the first and every subsequent level of the carrier core was achieved using a 3-molar excess of Fmoc-Lys(Fmoc) (0.2, 0.4, 0.8, and 1.6 mmol consecutively) in dimethylformamide (DMF) (HCONMe2, 12 ml/g resin) followed by a second coupling via HBTU in DMF to give, after deprotection, the octa-branched MAP matrix containing eight functional amino groups. The protecting groups for the synthesis of the peptide antigens were Fmoc groups for the alpha-amino termini and tBu derivatives for most side-chain amino acids. The coupling reactions were monitored by a quantitative ninhydrin test. The deprotection process was initiated by removing the Fmoc protecting group with 20% piperidine in DMF for 15 min. The branched peptide oligo-lysine was removed from the crosslinked polystyrene resin support with the TFA method cleavage to yield the crude MAP (85-93% cleavage yield). The crude peptide was then washed with cold ether and lyophilized and purified batch-wise by high performance gel-permeation.

Example 6

Active Immunization with the Branched Peptide Inhibits Tumor Progression In Vivo and Triggers Immunological Memory A MAP conjugate of peptide #161 (denoted 161-MAP)) is an octa-branched peptide where eight copies of the peptide sequence are conjugated to a core matrix of 8 lysine residues. This construct is expected to have increased stability and immunogenicity, so that conjugation to a carrier protein is no longer needed (Pini et al., Curr Protein Pept Sci. 2008; 9:468-477). Furthermore, the new conformation of the MAP renders it a neo-antigen which is capable of breaking immune tolerance despite the self sequence (Renaudet et al. PLoS One. 2010; 5:e11216).

Figure 8A:
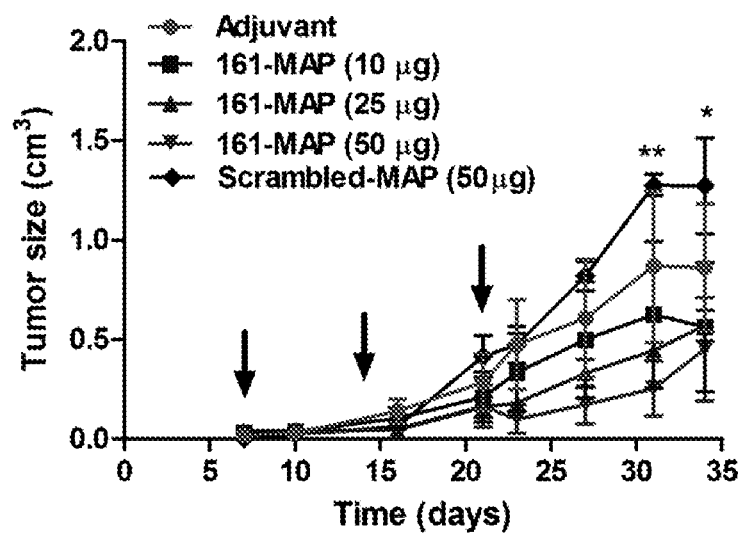
FIGS. 8A-8B Effect of active immunization with the branched #161-peptide (161-MAP) on tumor size in RENCA (FIG. 8A) and CT26 (FIG. 8B) tumor-bearing mice. Tumors were generated in BALB/c mice as before, and randomly assigned to the different groups. After 7 days the mice received the first injection of the adjuvant alone, the scrambled peptide (multiple antigenic peptide with the same composition of amino acids in a random order) control peptide (also in multiple antigenic peptide (MAP) format) or the 161-MAP branched peptide in different concentrations dissolved in complete Freund's adjuvant (CFA) directly into the footpad, followed by additional two boost injections, where the peptide was dissolved in incomplete Freund's adjuvant (IFA) every 7 days (black arrows). In the RENCA tumors—*, $p<0.05$, **, $p<0.01$ the scrambled group relative to the 25 µg and 50 µg groups; In the CT26 tumors—*, $p<0.05$, ***, $p<0.001$ scrambled group relative to all other groups at the indicated time points; $$, $p<0.01$ the adjuvant group relative to all other groups at the indicated time points.
Figure 8B:
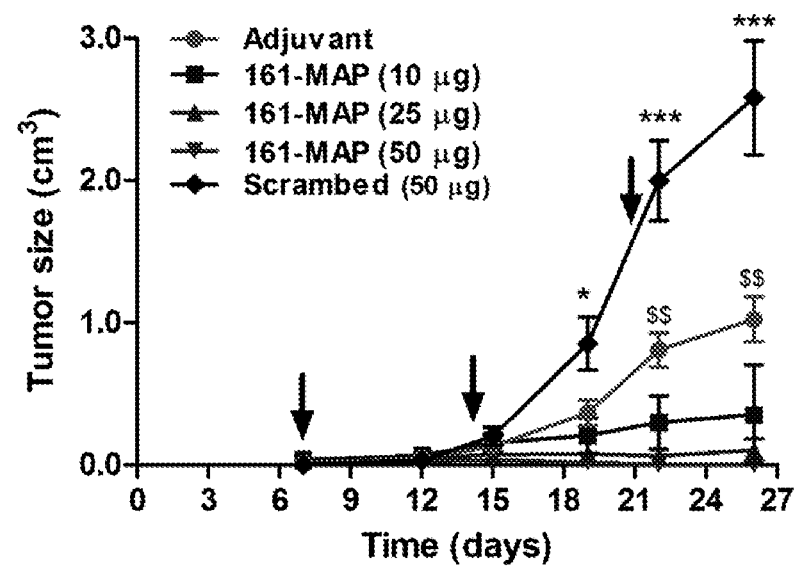
Figure 9:
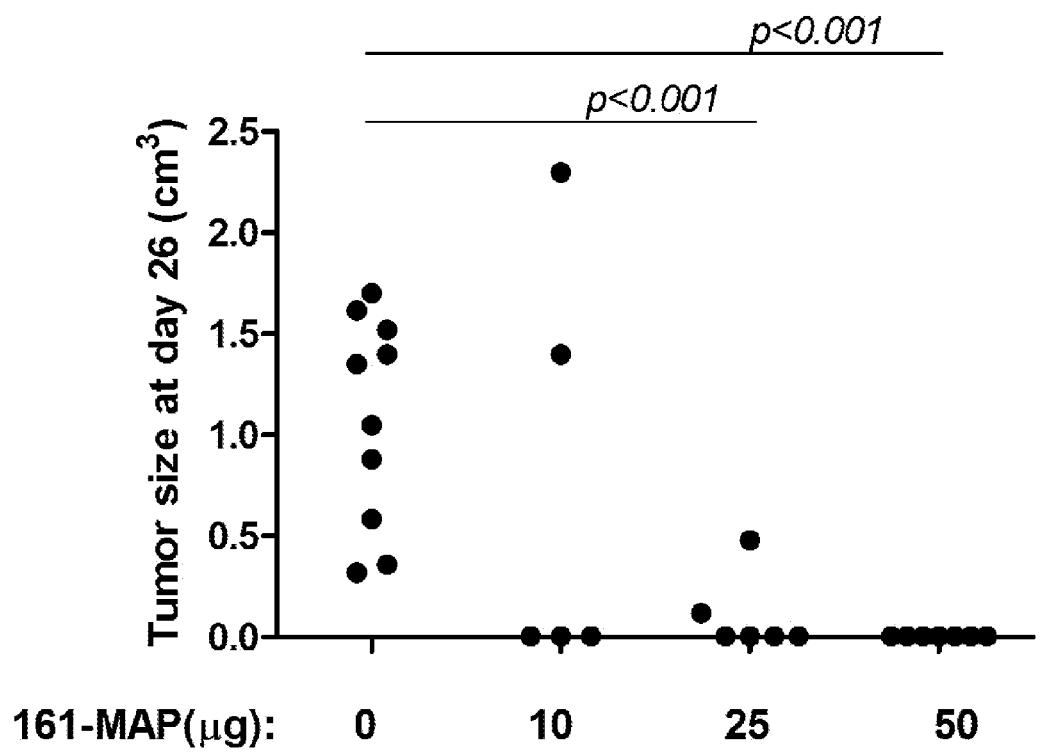
FIG. 9 CT26 tumor size at day 26 following 161-MAP or adjuvant injections as described in FIG. 8.

BALB/c mice were first injected with either the RENCA or CT26 cell lines, and after 7 days they received their first injection of the 161-MAP in CFA, followed by two booster injections in IFA every 7 days. The 161-MAP was injected in three concentrations (10 µg/30 µl, 25 µg/30 µl and 50 µg/30 µl) into the footpad. The control adjuvant group received injections with CFA and IFA without 161-MAP. Tumor growth was monitored every 3-4 days. In both RENCA and CT26 tumors, 161-MAP inhibited growth in a dose-dependent manner. In general, the response in CT26-injected mice was better. The dose-dependency reached statistical significance for the 25 and 50 µg groups only in mice injected with CT26 tumor cells ($p<0.001$ after 22 and 26 days relative to the adjuvant control group), and although the trend was similar with the RENCA tumors, it did not reach statistical significance (FIGS. 8B and A). In some of the mice injected with CT26 tumor cells (e.g., all of the mice in the group that received 50 µg of 161-MAP), the immunization caused full regression of the tumors that were already palpable (FIG. 9). The mice demonstrated temporary inflammation (swollen and red footpads) that passed after 3-4 weeks.

The 161-MAP acted in a dose dependent manner, and the higher peptide dose (50 µg) inhibited RENCA tumor growth by about 50%. In the CT26 tumor model the low peptide dose resulted in a 50% inhibition of tumor growth, whereas the high dose resulted in complete regression of tumors in all mice tested. However, some of the mice treated even with this low dose showed complete regression of the tumors (FIG. 9). Furthermore, all mice with regressed tumors, regardless of the branched peptide dose injected, were re-challenged with injection of tumor cells, but no tumors were detected (FIG. 10), compared to control mice in which tumors were detected.

Figure 10:
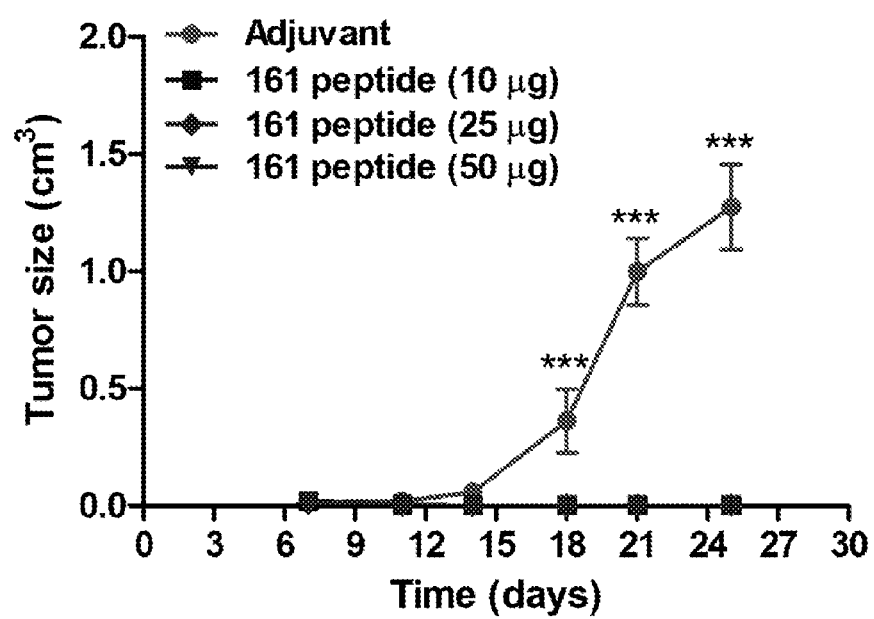

Unlike passive immunization that is already established for the treatment of cancer, active immunization has been tried infrequently as a strategy for cancer immune therapy, despite the inherent benefit of establishing immunological memory. To examine whether the process of immunizing mice against EMMPRIN with 161-MAP triggers immunological memory, the mice that survived and regressed their tumors were used. Three weeks after full regression, the mice continued to demonstrate good health with no side effects. The mice were then injected with $2\times10^6$ CT26 tumor cells for a second time. Although this procedure was sufficient to raise subcutaneous tumors in control mice after the first injection, tumors did not develop in any of the mice that survived after immunization with 161-MAP. In comparison, mice that received CFA and IFA injections to their footpad 3 times every 7 days before receiving the CT26 tumor cell injection (adjuvant), were used as control, and all of these control mice produced palpable tumors within 18 days (FIG. 10).

This finding strongly suggests that 161-MAP MAP succeeded in activating an immune response and generated immunological memory, implying that vaccinating tumor-bearing mice with the MAP sequence could prevent tumor recurrence.

This is further confirmed by detecting (by flow cytometry and immunohistochemistry using specific protein markers)) infiltrating neutrophils, specific macrophage subpopulations, NK cells, T cells and/or B cells in the tumors, by demonstrating active germinal centers in the spleens of immunized mice, and by demonstrating the presence of anti-EMMPRIN antibodies in their sera, using indirect ELISA.

Despite the multiple functions attributed to the EMMPRIN protein, no adverse physiological or change in the well-being of mice receiving the branched peptide were detected even after almost two months. Many of EMMPRIN functions are crucial during developmental stages, and it is possible that the adult functions of EMMPRIN are more crucial in the tumor context in comparison to normal tissue, suggesting why no adverse reactions were observed. In addition, epitopes different from that used for vaccination may be relevant for physiological and developmental functions of EMMPRIN Example 7

Re-challenging Model

Figure 11A:
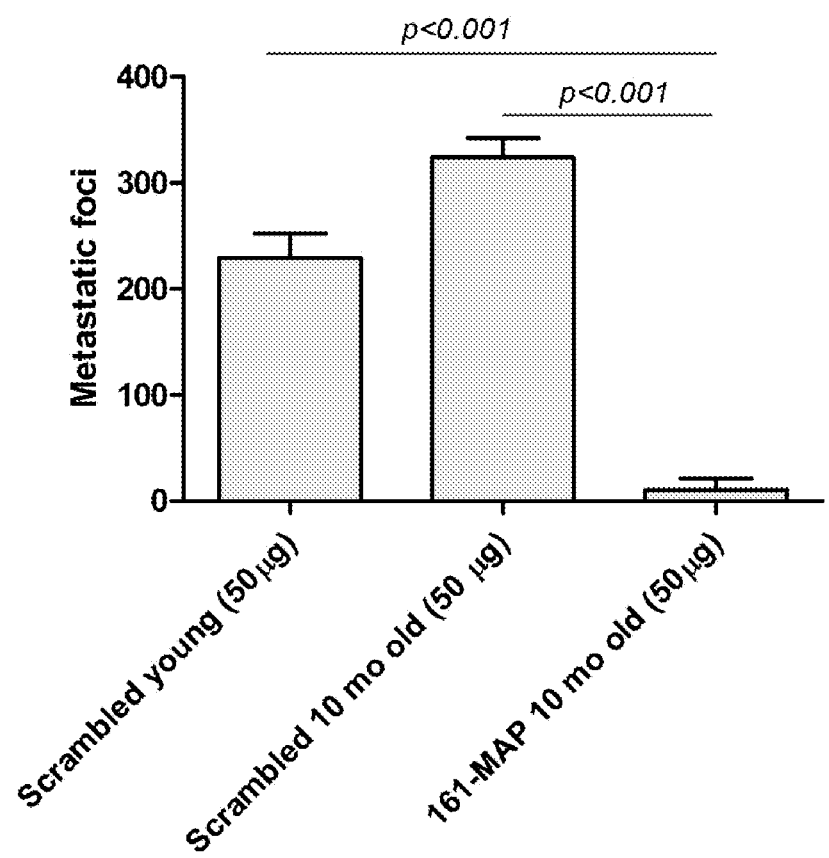
Figure 11B:
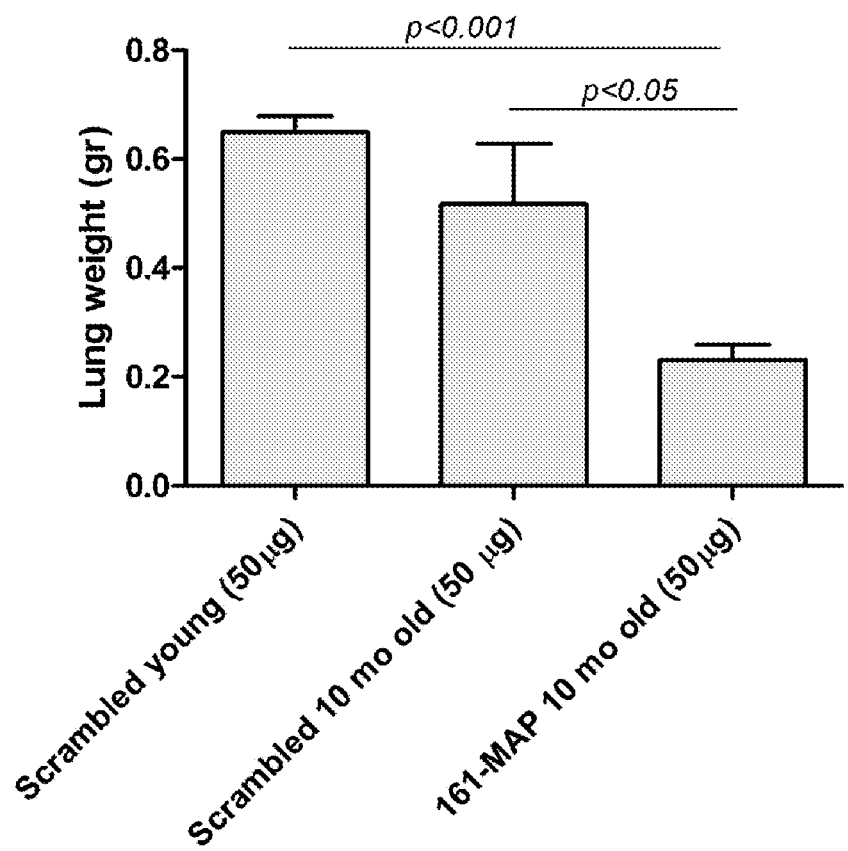

BALB/c female mice, 8 weeks old, were subcutaneously inoculated in the flank with $2\times10^6$ CT26 cells (at day 0), and 161-MAP at concentrations of 10 µg, 25 µg or 50 µg dissolved in 30 µl CFA (0.4, 1 and 2 mg/kg body weight) was injected at day 7 to the footpad, followed by additional two booster injections in IFA every 7 days. Mice that survived and showed complete regression of previously palpable tumors (FIG. 9) were inoculated to their flank with another challenge of $2\times10^6$ CT26 cells ($2^{nd}$ challenge), 6 weeks after the end of the first experiment ($1^{st}$ challenge). All 14 mice survived and none developed a tumor. One mouse died after 3.5 months, before receiving the $3^{rd}$ challenge, but no tumor was found in its flank or in its interior organs. The remaining 13 mice were subjected to a $3^{rd}$ challenge, repeating the exact protocol as for the $2^{nd}$ challenge, 6 months after the end of the first experiment ($1^{st}$ challenge). Again, all 13 mice that were injected with the $3^{rd}$ challenge survived and none developed a tumor (Table 3). As before, control mice received CFA and IFA injections to their footpad 3 times every 7 days before receiving the CT26 tumor cell injection (adjuvant).] Lastly, 4 of the 13 mice were randomly chosen post-challenge-3 and injected with $1\times10^6$ CT26 cells in the tail vein (i.v.) in order to generate metastases in the lung (Table 3). Three of the mice had no lung metastases, and only one developed 43 metastatic foci, in comparison to an average of 324 metastases developed in an 11-month-old mouse who received the scrambled peptide. Accordingly, as shown in FIG. 11, metastases increased lung weight (average of 0.572 gr in the control groups), and the lack of metastases in the 161-MAP-treated mice resulted in lung weight similar to those of healthy mice (average of 0.144 gr).

TABLE 3

161-MAP prevents tumor recurrence

| # challenge | Time of challenge | Route | Result | No. of mice |
| --- | --- | --- | --- | --- |
| $1^{st}$ inoculation | 0 | s.c. injection | Tumor regressed | 14 |
| $2^{nd}$ challenge | After 1.5 months | s.c. injection | No tumors | 14 |

TABLE 3-continued

161-MAP prevents tumor recurrence

| # challenge | Time of challenge | Route | Result | No. of mice |
|---|---|---|---|---|
| 3rd challenge | After 6 months | s.c. injection | No tumors | 13 |
| 4th challenge | After 11 months | i.v. injection | No metastases in 3 of 4 mice | 4 |

Example 8

Metastatic Models

The tumorigenic CT26 (colon) and RENCA (renal) cell lines do not spontaneously generate metastases from the primary tumor generated by s.c. injections to the flank. However, upon injections of the cells to the tail vein (i.v.) these cells migrate to the lungs and generate small tumors, which simulate lung metastases. This has become an accepted model for lung metastasis (Weng Y L, Mol Nutr Food Res. 2010 February; 54(2):259-67; Chang K H, et al, Am J Chin Med. 2004; 32(6):863-72; Lee Y J, et al, caner Res. 2010 70; 8357; Shanker A et al, JNCI J Natl Cancer Inst (2008) 100 (9): 649-662)).

Female BALB/c mice, 8 Week old were immunized by 3 boost injections every 7 days using increasing concentrations of either 161-MAP or the control scrambled-MAP. Seven days after the last boost injection, the mice received one injection into the tail vein of either CT26 cell or RENCA cells (1×10$^6$ in 200 µl of PBS). After 14-16 days (for the CT26 injected mice) or after 21-23 days (for the RENCA injected mice), the mice were sacrificed and the tumor nodules on the surface of the lungs were counted under a dissecting microscope. Lungs were removed, dried on a blotting paper and weighed (FIG. 12).

Figure 12A:
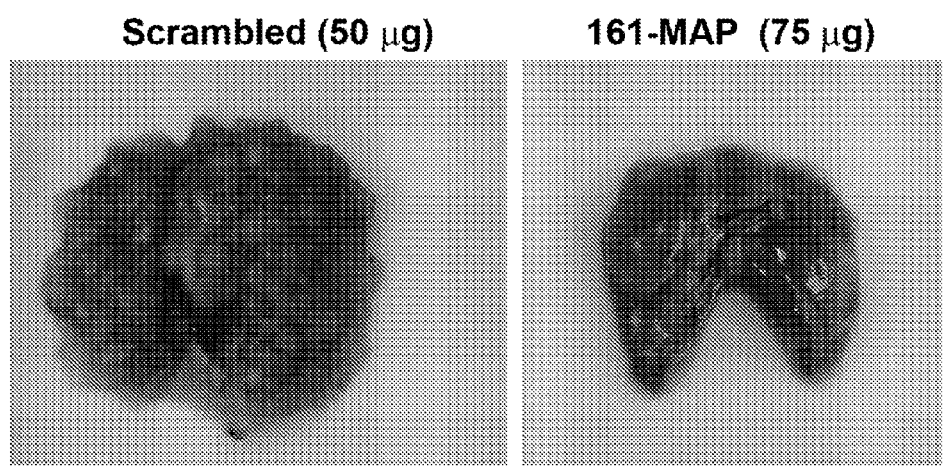
FIGS. 12A-12F The 161-MAP prevents formation of metastases. Mice were injected with three boost injections of 50 µg of the scrambled-MAP (control) or of increased amounts of 161-MAP in 30 µl of CFA and then IFA to their footpad every 7 days, and after an additional 7 days they received $10^6$ CT26 cells in 200 µl PBS injected to their tail vein. After 15 days (for CT26 injected mice) or 23 days (for RENCA injected mice), the mice were euthanized and their lungs were removed, weighed and the number of metastases were counted under a dissecting microscope.
Figure 12B:
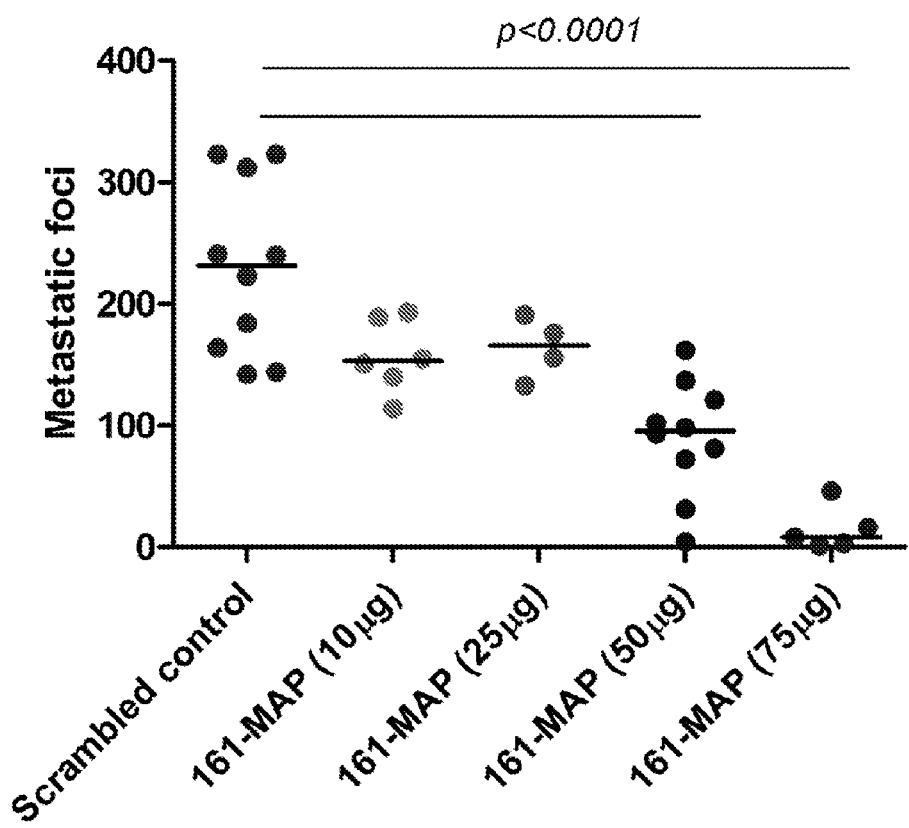
Figure 12C:
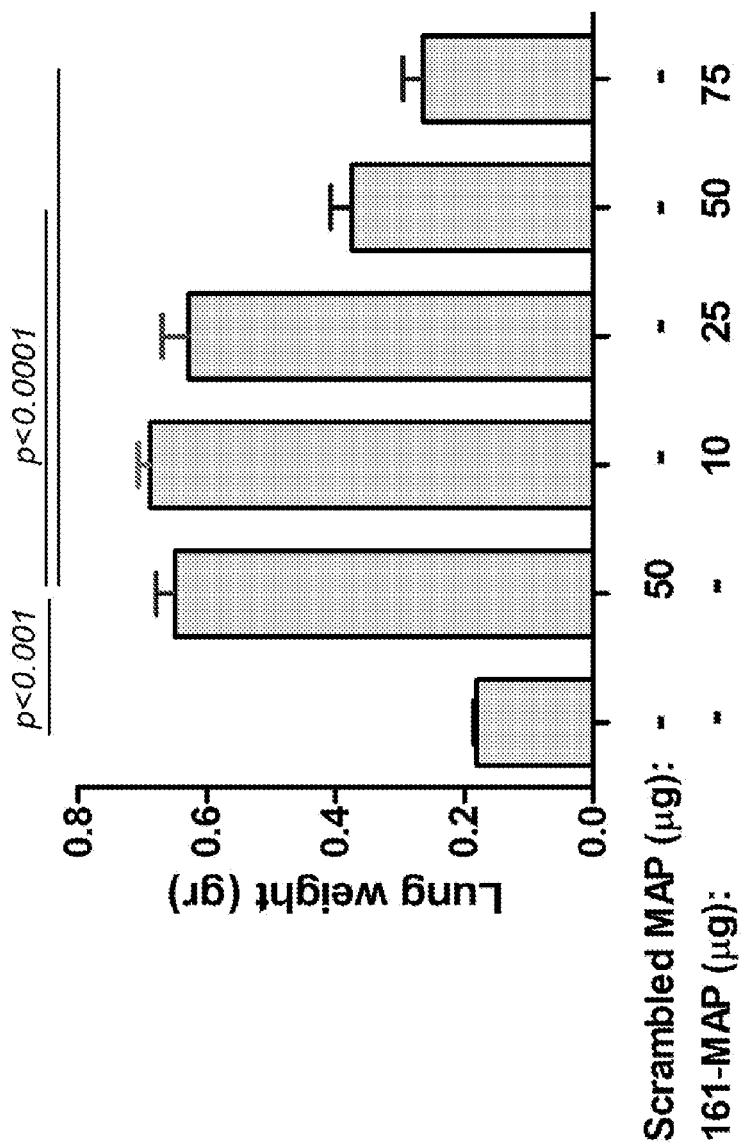
Figure 12D:
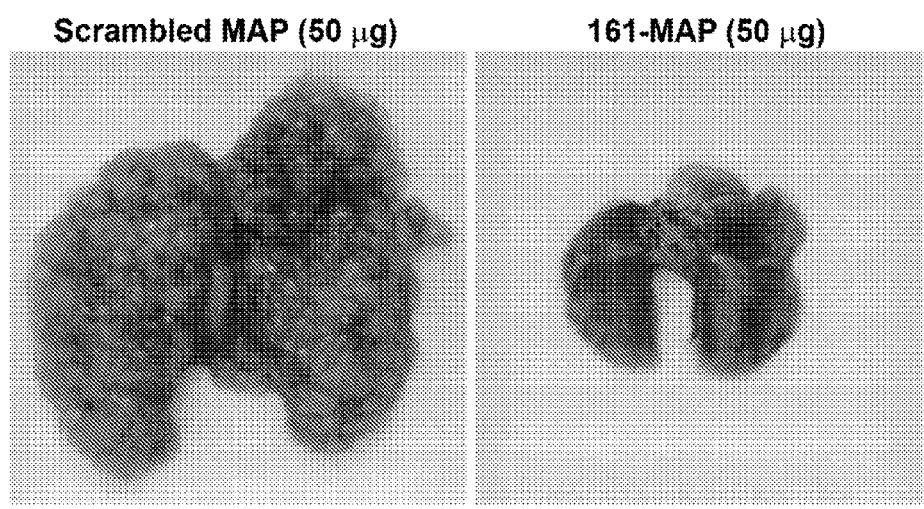
Figure 12E:
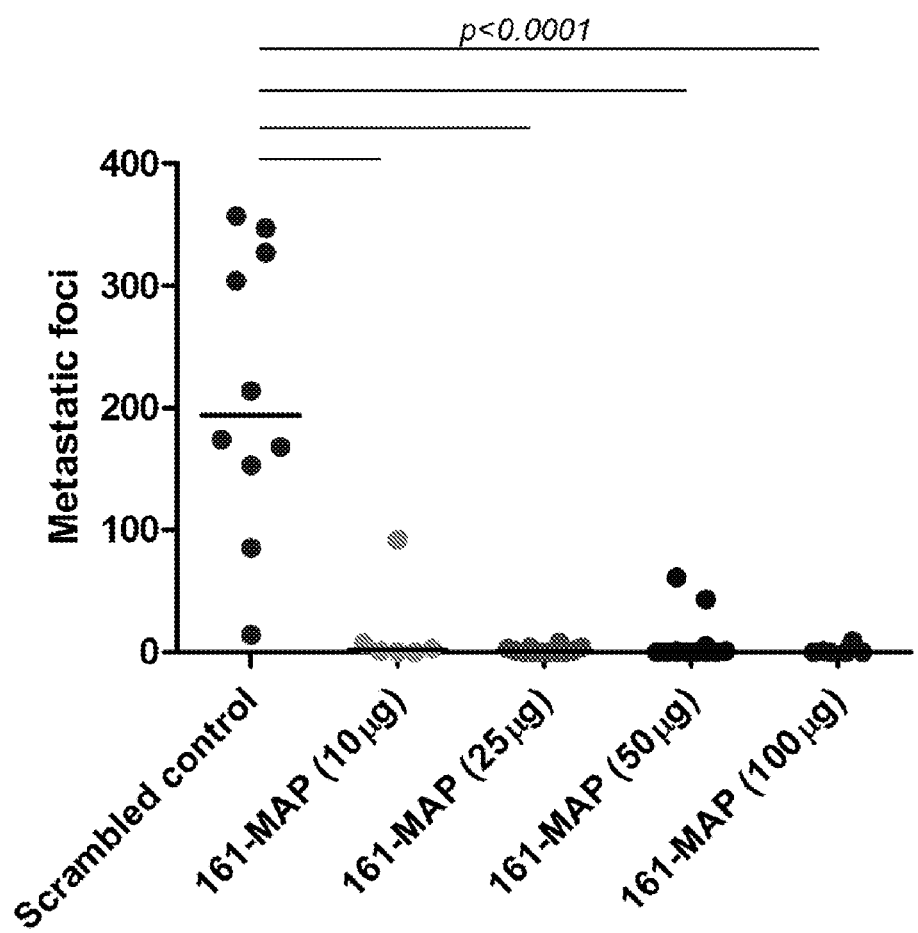
Figure 12F:
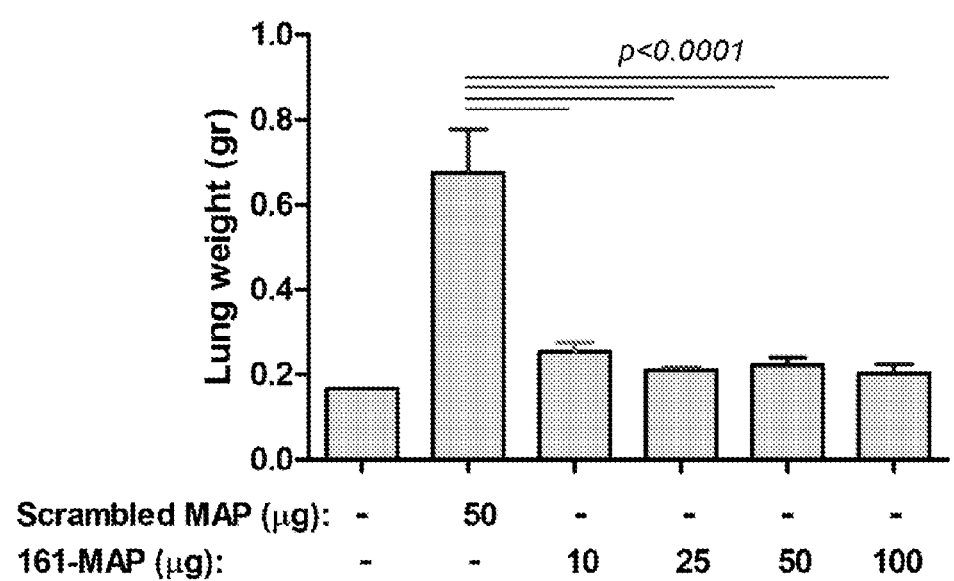

Results: Control mice receiving the scrambled-MAP developed lung metastases (on average: 230 metastases in CT26 mice, 214 metastases in RENCA mice) (FIGS. 12B and 12E), and accordingly their lung weight was increased by 3.5-4 folds relative to healthy mice with no cancer cell injections (0.675 gr in RENCA mice, 0.649 gr in CT26 mice) (FIGS. 12C and 12F). The 161-MAP succeeded almost completely in preventing lung metastases in RENCA mice in all doses used, whereas a clear dose-response was observed for the CT26 model. Similarly, the lung weight of mice receiving the 161-MAP was close to that of healthy mice in all doses used for the RENCA model, whereas the CT26 demonstrated a clear dose-response. Representative images of lungs from mice injected with CT26 or RENCA cells and receiving 50 µg of the scrambled MAP or 75 µg of 161-MAP are shown in FIGS. 12A and 12D.

The model wherein 161-MAP is administered prior to the metastatic cells actually mimics real-life scenario, where a primary tumor is treated by surgery or chemotherapy before the residual metastatic cells enter the circulation. Thus, the 161-MAP vaccination could successfully reduce and even dramatically prevent formation of lung metastases, and therefore could potentially be used as adjuvant therapy designed to prevent tumor recurrence in patients with conventionally treated primary tumors.

Example 9

Peptide Analogs of the 161 Peptide Sequence

Peptide analogs of the #161 sequence are synthesized and checked, alone, conjugated to carrier molecules and/or in MAP format, for activity and immunogenicity. A non-limiting list of such analogs includes the sequences in table 4. Antibodies raised against these sequences are also tested for activity in the in-vitro and in-vivo models described above.

TABLE 4

Peptide analogs of the #161 peptide

| | Mouse sequence | Human sequence |
|---|---|---|
| Original | GHRWMRGGKVLC (SEQ ID NO.: 1) | GHRWLKGGVVLC (SEQ ID NO.: 2) |
| Extended | TCSLNSSGVDIVGHRWMR GGKVLQ (SEQ ID NO.: 16) SGVDIVGHRWMRGGKVLQ (SEQ ID NO.: 18) | TCSLNDSATEVTGHRWLK GGVVLK (SEQ ID NO.: 17) SATEVTGHRWLKGGVVLK (SEQ ID NO.: 19) |
| Analogs | GHRFMRGGKVL (SEQ ID NO.: 20) GLRWMRGGKVL (SEQ ID NO.: 22) GHRWLRGGKVL (SEQ ID NO.: 24) GHRWMKGGKVL (SEQ ID NO.: 26) GHRWMRCGKVL (SEQ ID NO.: 28) GHRWMRGAKVL (SEQ ID NO.: 30) GHRWMRGGVVL (SEQ ID NO.: 32) | GHRFLKGGVVL (SEQ ID NO.: 21) GLRWLKGGVVL (SEQ ID NO.: 23) GHRWLRGGVVL (SEQ ID NO.: 25) GHRWMKGGVVL (SEQ ID NO.: 27) GHRWLKCGVVL (SEQ ID NO.: 29) GHRWLKGAVVL (SEQ ID NO.: 31) GHRWLKGGKVL (SEQ ID NO.: 33) |
| Fragments | GHRWMRG (SEQ ID NO.: 34) HRWMRGG (SEQ ID NO.: 36) RWMRGGK (SEQ ID NO.: 38) WMRGGKV (SEQ ID NO.: 40) | GHRWLKG (SEQ ID NO.: 35) HRWLKGG (SEQ ID NO.: 37) RWLKGGV (SEQ ID NO.: 39) WLKGGVV (SEQ ID NO.: 41) |

Computer System

A computer system is provided with which some embodiments of the invention are implemented. The computer system may includes a bus, a processor, a system memory, a read-only memory, a permanent storage device, one or more input devices, and one or more output devices.

In certain embodiments, the bus collectively represents all system, peripheral, and chipset buses that communicatively connect the numerous internal devices of the computer system. For instance, the bus may communicatively connect the processor with the read-only memory, the system memory, and the permanent storage device.

In certain embodiments, various memory units are parts of the computer system's computer readable medium from which the processor retrieves instructions to execute and data to process in order to execute the processes of the invention. The read-only-memory (ROM) stores static data and instructions that are needed by the processor and other modules of the computer system. The permanent storage device, on the other hand, is a read-and-write memory device. This device is a non-volatile memory unit that stores instructions and data even when the computer system is off. Some embodiments of the invention use a mass-storage device (such as a magnetic or optical disk and its corresponding disk drive) as the permanent storage device.

Other embodiments of the invention use a removable storage device (such as a floppy disk or USB flash disk) as the permanent storage device. Like the permanent storage device, the system memory is a read-and-write memory device. However, unlike storage device, the system memory is a volatile read-and-write memory, such a random access memory. The system memory stores some of the instructions and data that the processor needs at runtime. In some embodiments, the invention's processes are stored in the system memory, the permanent storage device, and/or the read-only memory.

In certain embodiments, the bus also connects to the input and output devices. The input devices enable the user to communicate information and select commands to the computer system. The input devices include alphanumeric keyboards and pointing devices. The output devices display images generated by the computer system. For instance, these devices display a graphical user interface. The output devices include printers and display devices, such as cathode ray tubes (CRT) or liquid crystal displays (LCD).

In certain embodiments, the bus also couples the computer to a network through a network adapter. In this manner, the computer can be a part of a network of computers (such as a local area network ("LAN"), a wide area network ("WAN"), or an Intranet, or a network of networks, such as the internet For example, the computer may be coupled to a web server (network) so that a web browser executing on the computer can interact with the web server as a user interacts with a graphical user interface that operates in the web browser.

In some embodiments, the server includes one or more computers having volatile memory, non-volatile memory, at least one processor, a wired or wireless network card, and at least one input/output device. In some embodiments, the server runs an operating system such as Microsoft Windows, UNIX, LINUX, or Mac OS. In sonic embodiments, the server receives patient data through a wired local area network (LAN) connection or a wireless LAN (WLAN) connection. In some embodiments, the server receives patient data through a connection to the Internet. In sonic embodiments, the server supplies data to an interface through LAN, WLAN, or the Internet.

In certain embodiments, any or all components of computer system may be used in conjunction with the invention. For instance, each of the computer readable memories of the computer system may function as one or more of the storages for some embodiments of the invention. One of ordinary skill in the art would appreciate that any other system configuration may also be used in conjunction with the present invention.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

---

The invention claimed is:

1. An isolated peptide of 11-25 amino acids, comprising the sequence

GHRWX₁X₂GGX₃VLC,  (SEQ ID NO.: 12)

wherein X₁ is selected from the group consisting of Met and Leu, X₂ is selected from the group consisting of Arg and Lys, and X₃ is selected from the group consisting of Lys and Val.

2. The isolated peptide of claim 1, consisting of a sequence selected from the group consisting of:

GHRWMRGGKVLC;  (SEQ ID NO.: 1)
and

GHRWLKGGVVLC.  (SEQ ID NO.: 2)

3. A fusion protein comprising at least one peptide according to claim 1.

4. A peptide multimer comprising a plurality of peptides according to claim 1, wherin said peptides are covalently linked.

5. The peptide multimer of claim 4, wherein said peptides are covalently linked through a linker comprising 3-12 Lysine residues.

6. The peptide multimer according to claim 5, wherein the peptide multimer is a molecule according to Formula II or III:

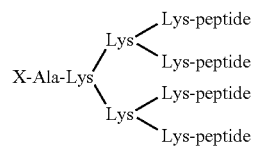

Formula II

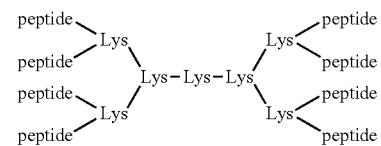

Formula III wherein X represents the peptide's C-terminal selected from carboxy acid, amide or alcohol group, "peptide" denotes a stretch of 11-25 amino acids, comprising the sequence GHRWX₁X₂GGX₃VLC (SEQ ID NO.: 12), wherein X₁ is selected from the group consisting of Met and Leu, X₂ is selected from the group consisting of Arg and Lys, and X₃ is selected from the group consisting of Lys and Val.

7. A pharmaceutical composition comprising at least one peptide or peptide analog according to claim 1, and a pharmaceutically acceptable carrier or diluent.

8. A pharmaceutical composition comprising at least one peptide multimer according to claim 4 and a pharmaceutically acceptable carrier or diluent.

* * * * *